(12) United States Patent
Roberts et al.

(10) Patent No.: US 8,105,578 B2
(45) Date of Patent: Jan. 31, 2012

(54) TREATMENT OF NEOPLASMS WITH VIRUSES

(75) Inventors: Michael S. Roberts, Walkersville, MD (US); Robert M. Lorence, Bethesda, MD (US); William S. Groene, New Market, MD (US); Harvey Rabin, Rockville, MD (US); Reid W. von Borstel, Potomac, MD (US)

(73) Assignee: Wellstat Biologics Corporation, Gaithersburg, MD (US)

( * ) Notice: Subject to any disclaimer, the term of this patent is extended or adjusted under 35 U.S.C. 154(b) by 516 days.

(21) Appl. No.: 11/698,947

(22) Filed: Jan. 29, 2007

(65) Prior Publication Data
US 2008/0057037 A1 Mar. 6, 2008

Related U.S. Application Data

(60) Division of application No. 10/044,955, filed on Jan. 15, 2002, now abandoned, which is a continuation of application No. 09/168,883, filed on Oct. 9, 1998, now abandoned, which is a continuation-in-part of application No. 08/948,244, filed on Oct. 9, 1997, now abandoned.

(51) Int. Cl.
*A01N 63/00* (2006.01)
*C12N 7/00* (2006.01)

(52) U.S. Cl. .................................... 424/93.6; 435/235.1

(58) Field of Classification Search ................. 435/320.1
See application file for complete search history.

(56) References Cited

U.S. PATENT DOCUMENTS

| | | | |
|---|---|---|---|
| 4,108,983 A | 8/1978 | Wallack |
| 5,124,148 A | 6/1992 | Csatary et al. |
| 5,198,336 A | 3/1993 | Knobeloch et al. |
| 5,215,745 A | 6/1993 | Csatary et al. |
| 5,273,745 A | 12/1993 | Schirrmacher |
| 5,274,137 A | 12/1993 | Nicolaou et al. |
| 5,585,096 A | 12/1996 | Martuza et al. |
| 5,602,023 A | 2/1997 | Csatary |
| 5,633,274 A | 5/1997 | Halperin et al. |
| 5,677,178 A | 10/1997 | McCormick |
| 5,688,773 A | 11/1997 | Chiocca et al. |
| 5,698,443 A | 12/1997 | Henderson et al. |
| 5,998,205 A | 12/1999 | Hallenbeck et al. |
| 6,110,461 A | 8/2000 | Lee et al. |
| 6,136,307 A | 10/2000 | Lee et al. |
| 6,261,555 B1 | 7/2001 | Lee et al. |
| 6,344,195 B1 | 2/2002 | Lee et al. |
| 6,551,587 B2 | 4/2003 | Hallenbeck et al. |
| 6,638,762 B1 | 10/2003 | Chang et al. |
| 7,122,182 B2 | 10/2006 | Groene et al. |
| 7,731,951 B2 | 6/2010 | Coffey et al. |

FOREIGN PATENT DOCUMENTS

| | | |
|---|---|---|
| DE | 39 22 444 C2 | 10/1991 |
| EP | 0 292 293 A2 | 11/1988 |
| EP | 0 292 293 A3 | 11/1988 |
| EP | 0 514 603 A | 11/1992 |
| EP | 0 564 121 A2 | 10/1993 |
| EP | 0 583 142 A2 | 2/1994 |
| EP | 0252741 B1 | 10/1997 |
| EP | 1 314 431 A2 | 5/2003 |
| GB | 1069144 | 5/1967 |
| JP | A 58-116422 | 7/1983 |
| JP | 10-5342 | 1/1998 |
| WO | WO 86/00529 | 1/1986 |
| WO | WO 86/00811 | 2/1986 |
| WO | WO 89/07445 | 8/1989 |
| WO | WO 93/18790 | 9/1993 |
| WO | WO 94/16716 | 8/1994 |
| WO | 94/19022 | 9/1994 |
| WO | WO 94/18992 | 9/1994 |
| WO | WO 94/19022 | 9/1994 |
| WO | 94/25627 | 11/1994 |
| WO | WO 94/25627 | 11/1994 |
| WO | WO 95/32706 | 12/1995 |
| WO | WO 96/00007 | 1/1996 |
| WO | WO 96/03997 | 2/1996 |
| WO | 96/16676 A1 | 6/1996 |
| WO | 96/17053 A1 | 6/1996 |
| WO | 96/26285 | 8/1996 |
| WO | WO 96/26285 | 8/1996 |
| WO | 96/34625 | 11/1996 |
| WO | WO 96/34625 | 11/1996 |
| WO | WO 97/01358 | 1/1997 |
| WO | WO 97/04805 | 2/1997 |
| WO | WO 97/26904 | 7/1997 |
| WO | 97/45550 A2 | 12/1997 |
| WO | WO 99/04026 | 1/1999 |
| WO | 99/08692 | 2/1999 |

(Continued)

OTHER PUBLICATIONS

Hormemann et al. J. Virol. 2003, vol. 77, No. 15, pp. 8394-8407.*
Symons et al. Cell, 1995, vol. 81, pp. 551-560.*
Kawakita et al. J. of the National Cancer Institute, Mar. 1997, vol. 89, No. 6, pp. 428-436.*
Eck, S.L., et al; "Gene-Based Therapy", *Goodman & Gilman's The Pharmacological Basis of Therapeutics*; 9th Edition, Chapter 5. pp. 77-101.
Faaberg, K.S., et al; "Strain Variation and Nuclear Association of Newcastle Disease Virus Matrix Protein"; *Journal of Virology*; vol. 62, No. 2; pp. 586-593 (1988).
Field, H.J., et al; "The Pathogenicity of Thymidine Kinase-Deficient Mutants of Herpes Simplex Virus in Mice"; *J. Hyg.Camb.*; vol. 81, pp. 267-277; (1978).
Foy, T.M., et al; "In Vivo CD40-gp39 Interactions are Essential for Thymus-Dependent Humoral Immunity. II. Prolonged Suppression of the Humoral Immune Response by an Antibody to the Ligand for CD40, gp39"; *J. Exp. Med.*; vol. 178, pp. 1567-1575 (1993).
Francoeur, A. M. et al; "The Isolation of Interferon-Inducing Mutants of Vesicular Stomatitis Virus with Altered Viral P Function for the Inhibition of Total Protein Synthesis"; *Virology*; vol. 160, pp. 236-245 (1987).

(Continued)

*Primary Examiner* — Zachariah Lucas
*Assistant Examiner* — Nicole Kinsey White
(74) *Attorney, Agent, or Firm* — Douglas A. Golightly

(57) ABSTRACT

The subject invention relates to viruses that are able to replicate and thereby kill neoplastic cells with a deficiency in the IFN-mediated antiviral response, and their use in treating neoplastic disease including cancer and large tumors. RNA and DNA viruses are useful in this regard. The invention also relates to methods for the selection, design, purification and use of such viruses for cancer therapy.

63 Claims, 5 Drawing Sheets

FOREIGN PATENT DOCUMENTS

| | | |
|---|---|---|
| WO | WO 99/08692 | 2/1999 |
| WO | 99/18799 | 4/1999 |
| WO | WO 99/18799 | 4/1999 |
| WO | WO 99/29343 | 6/1999 |
| WO | 99/45783 | 9/1999 |
| WO | WO 99/45783 | 9/1999 |
| WO | WO 99/55345 | 11/1999 |
| WO | WO 99/64068 A | 12/1999 |
| WO | WO 00/45853 | 8/2000 |
| WO | WO 00/54795 A | 9/2000 |
| WO | 00/62735 | 10/2000 |
| WO | WO 00/62735 | 10/2000 |

OTHER PUBLICATIONS

Ganly, et al; "Phase I Trial of Intratumoral Injection with an E1B-Attenuated Adenovirus, ONYX-015, in Patients with Recurrent p53(−) Head and Neck Cancer"; *Proceedings of ASCO*; vol. 16; p. 382a; Abstract 1362 (1997).

Gastl, G., et al; "Retroviral Vector-Mediated Lymphokine Gene Transfer into Human Renal Cancer Cells"; *Cancer Research*; vol. 52, pp. 6229-6236 (1992).

Goldstein, D.J., et al; "Factor(s) Present in Herpes Simplex Virus Type 1-Infected Cells Can Compensate for the Loss of the Large Subunit of the Viral Ribonucleotide Reductase: Characterization of an ICP6 Deletion Mutant"; *Virology*; vol. 166; pp. 41-51 (1988).

Gresser, I., "Exogenous Interferon and Inducers of Interferon in the Treatment of Balb/c Mice Inoculated with $RC_{19}$ Tumour Cells"; *Nature*; vol. 223; pp. 844-845 (1969).

Gresser, I.; "Inhibitory Effect of Interferon on Murine Sarcoma and Leukaemia Virus Infection in Vitro"; *Nature*; vol. 223; p. 845 (1969).

Gross, S.; "Measles and Leukemia"; *The Lancet*; pp. 397-398 (1971).

Haines, G.K., et al; "Correlation of the Expression of Double-Stranded RNA-Dependent Protein Kinase (p68) with Differentiation in Head and Neck Squamous Cell Carcinoma"; *Virchows Archiv. B Cell Pathol.*; vol. 63; pp. 289-295 (1993).

Hanson, R.P., et al; "Identification of Vaccine Strains of Newcastle Disease Virus"; *Science*; vol. 122, pp. 156-157 (1955).

Hashiro, G., et al; "The Preferential Cytotoxicity of Reovirus for Certain Transformed Cell Lines" *Archives of Virology*; vol. 54, pp. 307-315 (1977).

Heise, C., et al; "ONYX-015, an E1B Gene-Attenuated Adenovirus, Causes Tumor-Specific Cytolysis and Antitumoral Efficacy that can be Augmented by Standard Chemotherapeutic Agents"; *Nature Medicine*; vol. 3 No. 6, pp. 639-645 (1997).

Holzaepfel, J.H., et al; "The Use of $APC_3$ Virus as a Cancericidal Agent"; *Cancer*; vol. 10, pp. 577-580 (1957).

Horvath, J., et al; "Comparison of Oncolytic Newcastle Disease Virus Strains"; *Experimental Therapeutics*; #2619; (Cancer Institute, St. Joseph's Hospital, Tampa, FL).

Howard, B., et al; "Retrovirus-Mediated Gene Transfer of the Human γ-IFN Gene: A Therapy for Cancer"; *Annals New York Academy of Sciences*; pp. 167-187.

Hughes, S.J., et al; "Vaccinia Virus Encodes an Active Thymidylate Kinase That Complements a *cdc8* Mutant of *Saccharomyces cerevisiae*"; *The Journal of Biological Chemistry*; vol. 266, No. 30; pp. 20103-20109 (1991).

Ideo, G., et al; "Viruses in the Treatment of Cancer"; *The Lancet*; pp. 825-826 (1971).

Ikeda, H., et al; "Detection of Heterozygous Mutation in the Retinoblastoma Gene in a Human Pituitary Adenoma Using PCR-SSCP Analysis and Direct Sequencing"; *Endocrine Pathology*; vol. 6, No. 3; pp. 189-196 (1995).

Imani, F., et al; "Inhibitory Activity for the Interferon-Induced Protein Kinase is Associated with the Reovirus Serotype 1 σ3 Protein"; *Proc. Natl Acad. Sci.*; vol. 85, pp. 7887-7891 (1988).

E.I. Ugochukwu; "Caecal Coccidiosis in Chicks Following Intramuscular Vaccination Against Newcastle Disease"; Bull. Anim. Health Prod. Afr., (1982) vol. 30, No. 4, pp. 353-357; XP-002237257; (Abstract).

W. Leuthgen; "Detection of Antibodies in the Tracheal Exudate of Chicken After Infection with Newcastle Virus"; Immunologie (1972), 144(3), 273-80; XP-002237258 (Abstract).

Hanson et al; "Identification of Vaccine Strains of Newcastle Disease Virus"; Science, vol. 156, 1955, pp. 156-157; XP002237246.

Sinkovics et al, "New Developments in the Virus Therapy of Cancer: A Historical Review," Intervirology, vol. 36, pp. 193-214 (1993).

XP-002164069, Horvath et al, "Comparison of oncolytic Newcastle Disease Virus strains," Cancer Institute, St. Joseph's Hospital, Tampa, Florida).

Restifo et al, "A Nonimmunogenic Sarcoma Transduced with the cDNA . . . ," The Journal of Experimental Medicine, vol. 175, pp. 1423-1431 (1992).

Beattie et al, "Host-Range Restriction of Vaccinia Virus . . . ," Virus Genes, vol. 21, No. 1, pp. 89-94 (1996).

Arroyo et al, "Active specific immunotherapy with vaccinia colon . . . ," Cancer Immunol Immunother, vol. 31, pp. 305-311 (1990).

Yu et al, "Antiviral action of interferon-β on . . . ," Med Microbial Immunol, vol. 184, pp. 45-52 (1995).

Nickels et al, "Identification of an amino acid change that affects . . . ," Journal of General Virology, vol. 75, pp. 3591-3595 (1995).

Schubert et al, "Primary Structure of the Vesicular . . . ," Journal of Virology, Aug. 1984, pp. 505-514.

Balachandran et al,"Activation of the dsRNA-dependent protein . . . ," The EMBO Journal, vol. 17, No. 23, pp. 6888-6902 (1998).

Durbin et al, "Targeted Disruption of the Mouse *Stat1* Gene Results . . . ," Cell, vol. 84, pp. 443-450 (1996).

Stojdl et al, "Exploiting tumor-specific defects in the interferon pathway . . . ," Nature Medicine, vol. 6, No. 7, pp. 821-825 (2000).

Balachandran et al, "Vesicular Stomatitis Virus . . . ," Life, vol. 50, pp. 135-138 (2000).

Francoeur et al, "The Isolation of Interferon-Inducing Mutants of . . . ," Virology, vol. 160, pp. 236-245 (1987).

Database CAPLUS, on STN Columbus (OH): chemical abstract service, DN 116: 104333, CN 1054192 A, Zhang, B. "Attenuated new castle disease virus for induction of interferons to combat neoplasm or viral diseases." Abstract, Apr. 9, 1991.

Gresser et al. Exogenous Interferon and Inducers of Interferon in the Treatment of Balb/c Mice Inoculated with RC19 Tumor Cells. Nature. 223 Aug. 1969, vol. 223, pp. 844-845, see entire document.

Rosenbergova et al, "Purification of Newcastle Disease . . . ," Acta virol, vol. 25, pp. 31-35 (1981).

Maeda et al, "Isolation and Characterization of Defective Interfering . . . ," Microbiol. Immunol., vol. 22, No. 12, pp. 775-784 (1978).

Strube et al, "Sensitivity of ortho- and paramyxovirus replication to human interferon α," Molec. Biol. Rep., vol. 10, pp. 237-243 (1985).

Hashiro, G., et al, Archives of Virology 54, 307-315 (1977) "The Preferential Cytotoxicity of Reovirus for Certain Transformed Cell Lines".

Lorence, R.M., et al, Cancer Research, 54: 6017-6021, Dec. 1, 1994 "Complete Regression of Human Fibrosarcomaj Xenografts after Local Newcastle Disease Virus Therapy".

Database CAPLUS, on STN Columbus (OH):chemical abstract service, DN 116: 104333, CN 1054192 A. Zheng, B., "Attenuated new castle disease virus for induction of interferons to combat neoplasm or viral diseases," Abstract, Apr. 9, 1991.

Gresser, et al, "Exogenous Interferon and Inducers of Interferon in the Treatment of Balb/c Mice Inoculated with RC19 Tumor Cells," Nature, Aug. 23, 1969, vol. 223, pp. 844-845.

Csatary, L.K., et al, Orvosi Hetilap 131: 2585-2588, 1990, "Virus Vaccines for the Tratment of Cancer".

Eck et al, "Gene-Based Therapy," Goodman & Gilman's The Pharmacological Basis of Therapeutics, $9^{th}$ Edition, chapter 5.

Verma et al, "Gene-Based Therapy-Promises, Problems and Prospects," Nature, vol. 389, pp. 239-242.

Kirn, D.H., et al, *Molecular Medicine Today*, Dec. 1996, p. 519-527, "Replicating Viruses as Selective Cancer Therapeutics,".

Heise, C., et al, *Nature Medicine*, vol. 3, No. 6, Jun. 1997, p. 639-645 "ONYX-015, an E1B gene-attenuated adenovirus, causes tumor-specific cytolysis and antitumoral efficacy that can be augmente4d by standard chemotherapeutic agents".

Zhang, Jian-Feng, et al, *Proc. Natl. Acad. Sci*, vol. 93, pp. 4513-4518, Apr. 1996, "Treatment of a human breast cancer xenograft with an adenovirus vector containing an interferon gene results in rapid regression due to viral oncolysis and gene therapy".

Katze, Michael G., *Trends in Microbiology*, vol. 3, No. 2, Feb. 1995, pp. 75-78, "Regulation of the interferon-induced PKR:can viruses cope?"

Maheshwari, Rada K., et al, *Biochemical and Biophysical Research Communications*, vol. 117, No. 1, Nov. 30, 1983, pp. 161-168, "Low Infectivity of Vesicular Stomatitis Virus (VSV) Particles Released from Interferon-Treated Cells is Related to Glycoprotein Deficiency".

Chou, Joany, et al, *Proc. Natl. Acad. Sci. USA*, vol. 92, pp. 10516-10520, Nov. 1995, "Association of a Mr 90,000 phosphoprotein with protein kinase PKR in cells exhibiting enhanced phosphorylation of translation . . . herpes simplex virus 1".

Xu, Bo, et al, *Blood*, vol. 84, No. 6, Sep. 15, 1994, pp. 1942-1949, "Primary Leukemia Cells Resistant to ∀-Interferon in Vitro are Defective in the Activation of the DNA-Binding Factor . . . Factor 3".

Petricoin III, Emanuel, et al, *Molecular and Cellular Biology*, vol. 14, No. 2, Feb. 1994, pp. 1477-1486 "Human Cancer Cell Lines Express a Negative Transcriptional Regulator of the Interferon Regulatory Factor Family of DNA Binding Proteins".

Symons, Julian A., et al, *Cell*, vol. 81, pp. 551-560, May 19, 1995, "Vaccinia Virus Encodes a Soluble type I Interferon Receptor of Novel Structure and Broad Species Specificity".

Linge, Claire, et al, *Cancer Research 55*, pp. 4099-4104, Sep. 15, 1995, "Interferon System Defects in Human Malignant Melanoma".

Machida, Haruhiko, et al, *Microbiol. Immunol.*, vol. 23 (7), 643-650, 1979, "Effect of Nucleosides on Interferon Production and Development of Antiviral State Induced by Poly I ! Poly C".

Tanaka, Nobuyuki, et al, *Cell*, vol. 77, 829-839, Jun. 17, 1994, Cellular Commitment to Oncogene-Induced Transformation or Apoptosis is Dependent on the Transcription Factor IRF-1.

*Science*, vol. 274, Oct. 18, 1996, pp. 342-343, "Will a Twist of Viral Fate Lead to a New Cancer Cure?"

Bischoff, James R., et al, *Science*, vol. 274, Oct. 18, 1996, pp. 373-376, "An Adenovirus Mutant That Replicates Selectively in p53-Deficient Human Tumor Cells".

Andreansky, Samita S., et al, *Proc. Natl. Acad. Sci. USA*, vol. 93, pp. 11313-11318, Oct. 1996 Colloquium Paper, "The application of genetically engineered herpes simplex viruses to the treatment of experimental brain tumors".

Gastl, Guenther, et al, *Cancer Research 52*, pp. 6229-6236, Nov. 15, 1992, "Retroviral Vector-mediated Lymphokine Gene Transfer into Human Renal . . . Cells".

Buller, R. Mark L., et al, *Virology 164*, 182-192 (1988), "Cell Proliferative Response to Vaccinia Virus is Mediated by VGF".

Child, Stephanie J., et al, *Virology*, 174, 625-629 (1990), "Insertional Inactivation of the large Subunit of mutants of herpes simplex virus in mice".

Spriggs, Dale R., et al, Nature, vol. 297, May 6, 1982, pp. 68-70, "Attenuated reovirus type 3 strains generated by selection of haemagglutinin antigenic variants".

Goldstein, Dvid J., et al, Virology, 166, 41-51 (1988), Factor(s) present in Herpes Simplex Virus Type 1-Infected Cells Can Compensate for the Loss of the Large Subunit of thej Viral Ribonucleotide Reductase: Characterization of an ICP6 Deletion Mutant.

Perkus, Marion E., et al, Virology, 180, 406-410 (1991), "Deletion of 55 Open Reading Frames from the Termini of Vaccinia Virus".

Meignier, Bernard, et al, Journal of Infectious Diseasesb, 162: 313-321 (1990), In Vivo Behavior of Genetically Engineered Herpes Simplex Viruses R7017 and R7020. II. Studies in Immunocompetent and Immunosuppressed Owl Monkeys (*Aotus trivirgatus*).

Hughes, Stephen J., et al, Journal of Biological Chemistry, vol. 266, No. 30, Issue of Oct. 25, 1991, pp. 20103-20109, Vaccinia Virus Encodes an Active Thymidylate Kinase That Complements a *cdc8* Mutant of *Saccharomyces cerevisiae*.

Kerr, Shona M., et al, The EMBO Journal, vol. 10, No. 13, pp. 4343-4350, (1991), Vaccinia DNA ligase complements *Saccharomyces cerevisiae* cdc9, localizes in cytoplasmic factories and affects virulence and virus sensitivity to DNA damaging agents.

Clark, H. Fred, et al, Journal of Infectious Diseases, vol. 158, No. 3, Sep. 1988, p. 570-587, "Protective Effect of WC3 Vaccine Against Rotavirus Diarrhea in Infants During a predominantly Serotype 1 Rotavirus Season".

Takafuji, Ernest T., et al, Journal of Infectious Diseases, vol. 140, No. 1, Jul. 1979, pp. 48-53, "Simultaneous Administration of Live, Enteric-Coated Adenovirus Types 4, 7, and 21 Vaccines: Safety and Immunogenicity".

Taylor, M.W., et al, Journal of the National Cancer Institute, vol. 44, No. 3, Mar. 1970, pp. 515-519, "Virus-Induced Regression of Tumor Growth".

Beattie, Elizabeth, et al, Virus Genes, 12:1, 89-94, 1996, "Host-Range Restriction of Vaccinia Virus E3L-Specific Deletion Mutants".

Howard, Brad, et al, Annals New York Academy of Sciences, Duke University Medical Center, p. 167-187, "Retrovirus-Mediated Gene Transfer of the Human (-IFN Gene: A Therapy for Cancer".

Suskind, R.G., et al, US Dept. of Health, Education, & Welfare, N.I.H., National Institute of Allergy and Infectious Diseases, and National Cancer Inst., Bethesda, Md. Oncolytic Effect of Coxsackie Virus, pp. 309-318, "Viral Agents Oncolytic for Human Tumors in Heterologous Host. Oncolytic Effect of Coxsackie B. Viruses." (22932), Oct. 29, 1956.

Bluming, Avrum Z., et al, The Lancet, Jul. 10, 1971, p. 105-106 "Regression of Burkitt's Lymphoma . . . Association With measles Infection".

Pasquinucci, G., The Lancet, Jan. 16, 1971, i, 136 "Possible Effect of Measles on Leukaemia".

Gross, Samuel, The Lancet, Feb. 20, 1971, p. 397-398, "Measles and Leukaemia".

Shingu, M., Journal of General Virology (1991), 72, 2031-2034, "Therapeutic effects of bovine enterovirus infection on rabbits with experimentally induced adult T cell leukaemia".

Faaberg, Kay S., et al, Journal of Virology, vol. 62, No. 2, p. 586-593, Feb. 1988, "Strain Variation and Nuclear Association of Newcstle Disease Virus Matrix Protein".

Holzaepfel, John H., et al, Cancer, May-Jun. 1957, vol. 10, pp. 577-580, "The Use of APC3 Virus as a Cancericidal Agent".

Smith, Robert R., MD, et al, Cancer, Nov.-Dec. 1956, vol. 9, pp. 1211-1218, "Studies on the Use of Viruses in the Treatment of Carcinoma of the Cervix".

Rukavishnikova, G.E., et al, Acta Virol., 20:387-394, 1976, "Some Immunological Mechanisms of the Influenza Virus Antitumour Effect".

Kalvakolanu, D.V.R., et al, Proc. Natl. Acad. Sci. USA, vol. 90, pp. 3167-3171; Apr. 1993, "Differentiation-dependent activation of interferon-stimulated gene factors and transcription factor NF-kB in mouse embryonal carcinoma cells".

Foy, Teresa M., et al, J. Exp. Med. © The Rockefeller University Press—0022-1007/93/11/1567/09, vol. 178, Nov. 1993, pp. 1567-1575, "In Vivo CD40-gp39 Interactions are Essential for Thymus-dependent Humoral Immunity. II. Prolonged Suppression of the Humoral Immune jResponse by an Antibody to the Ligand for CD40, gp39".

Blaese, R.M., et al, European Journal of Cancer, vol. 30A, No. 8, pp. 1190-1193, 1994, "In situ Delivery of Suicide Genes for Cancer Treatment".

Zhang, Jian Feng, et al, Cancer Gene Therapy, vol. 3, No. 1, 1996, pp. 31-38, "Gene therapy with an adeno-associated virus carrying an interferon gene results in tumor growth suppression and regression".

Peplinski, Gary R., et al, Annals of Surgical Oncology, 3(2):15-23, "Prevention of Murine Breast Cancer by Vaccination with Tumor Cells Modified by Cytoline-Producing Recombinant Vaccinia Viruses".

Cotran, Ramzi S., M.D., et al, Robbins Pathologic Basis of Disease, 4th Edition, p. 251, "Kinetics of Tumor Cell Growth".

Schloer, G.M., et al, Journal of Virology, vol. 2, No. 1, Jan. 1968, pp. 40-47, "Relationship of Plaque Size and Virulence for Chickens of 14 Representative Newcastle Disease Virus Strains".

Tait, David L., et al, Clinical Cancer Research, vol. 3, pp. 1959-1968, Nov. 1997, "A Phase I Trial of Retroviral BRCA1sv Gene Therapy in Ovarian Cancer".

Martuza, Robert L., et al, Science, vol. 252, pp. 854-855, May 10, 1991, "Experimental Therapy of Human Glioma by Means of a Genetically Engineered Virus Mutant".

Hanson, R.P., et al, Science, vol. 122, pp. 156-157, Jul. 22, 1955, "Identification of Vaccine Strains of Newcastle Disease Virus".

Chambers, Renee, et al, Proc. Natl. Acad. Sci. USA, vol. 92, pp. 1411-1415, Feb. 1995, "Comparison of genetically engineered herpes simplex viruses for the treatment of brain tumors in a scid mouse model of human malignant glioma".

Asada, Teruo, MD, Cancer, vol. 34, pp. 1907-1928, Dec. 1974,"Treatment of Human Cancer with Mumps Virus".

Sreevalsan, Thazepadath, Biologic Therapy of Cancer: Principles and Practice, pp. 347-364, Chapter 14 Biologic Therapy with Interferon-∀ and Ǝ: Preclinical Studies.

Stoner, Gary D., et al, Nature, vol. 245, Oct. 12, 1973, pp. 319-320, "Effect of Neuraminidase pretreatment on the Susceptibility of Normal and Transformed Mammalian Cells to Bovine Enterovirus 261".

Joklik, W.K., Virology, Second Edition 1990, pp. 383-410, "Interferons".

Schnell, Matthias, J., et al, Cell, vol. 90, pp. 849-857, Sep. 5, 1997, "Construction of a Novel Virus that Targets HIV-1-Infected Cells and Controls HIV-1 Infection".

Lorence, Robert M., et al, Journal of the National Cancer Institute, vol. 86, No. 16, Aug. 17, 1994, pp. 1228-1233, Complete Regression of Human Neuroblastoma Xenografts in Athymic Mice After Local Newcastle Disease Virus Therapy.

Kirchner, H.H., et al, World J Urol. (1995) 13:171-173, "Adjuvant treatment of locally advanced renal cancer with autologous virus-modified tumor vaccines".

Murphy, Frederick A., et al, Virology, Second Edition, 1990, Chapter 2, pp. 9-35, "Virus Taxonomy".

Csatary, Laszlo K., The Lancet, Oct. 9, 1971, p. 825, "Viruses in the Treatment of Cancer".

Ahlert, T., et al, Cancer Res. 50 (1990), pp. 5962-5968, Isolation of a Human Melanoma Adapted.

Kubo, T.; Patent Application No. S49-147261; Public Patent Disclosure Bulletin No. JP S51-73117 dated Jun. 24, 1976; Title of Invention "A method for preparing a cancer therapy agent" (6 pgs).

Jia Fenglan et al; ACTA Academiae Medicinae Sinicae; vol. 7, No. 5; Oct. 1985 (4 pgs).

Reichard, K.W., et al; The Association for Academic Surgery; Twenty-Fifth Annual Meeting, Nov. 20-23, 1991, University of Colorado Health Sciences Center, Denver, Colorado (p. 152).

Huang et al ; ACTA Academiae Medicinae Sinicae, vol. 6, No. 3 (1984) (5 pgs).

Mastrangelo, Michael J., et al; "Poxvirus vectors: orphaned and underappreciated"; *The Journal of Clinical Investigation*; vol. 105; No. 8; pp. 1031-1034 (2000).

Lee, Sharon S., et al; "Intravesical Gene Therapy: In Vivo Gene Transfer Using Recombinant Vaccinia Virus Vectors"; *Cancer Research*, vol. 54; pp. 3325-3328 (1994).

Arakawa, Soichi, Jr., et al; "Clinical trial of attenuated vaccinia virus AS strain in the treatment of advanced adenocarcinoma"; *J. Cancer Res. Clin. Oncol.*; vol. 113; pp. 95-98 (1987).

Kawa, Akira, et al; "The Effect of Attenuated Vaccinia Virus AS Strain on Multiple Myeloma; A Case Report"; *Japan J. Exp. Med.*; vol. 57; pp. 79-81 (1987).

Lattime, Edmund C.; "In Situ Cytokine Gene Transfection Using Vaccinia Virus Vectors"; *Seminars in Oncology*; vol. 23, No. 1; pp. 88-100 (1996).

Carroll, Kathleen, et al; "Recombinant Vaccinia Virus K3L Gene Product Prevents Activation of Double-stranded RNA-dependent, Initiation Factor 2α-specific Protein Kinase"; *The Journal of Biological Chemistry*; vol. 268, No. 17; pp. 12837-12842 (1993).

Qin, Hx, et al; "Construction of recombinant vaccinia virus expressing GM-CSF and its use as tumor vaccine"; *Gene Therapy*; vol. 3; pp. 59-66 (1996).

Kaufman, H., et al; A Recombinant Vaccinia Virus Expressing Human Cardinoembryonic Antigen (CEA); *Int. J. Cancer*; vol. 48; pp. 900-907 (1991).

Ju, Dian Wen, et al; "Intratumoral injection of GM-CSF gene encoded recombinant vaccinia virus elicits potent antitumor response in a murine melanoma model"; *Cancer Gene Therapy*; vol. 4, No. 2; pp. 139-144 (1997).

Horvath, J., et al; "Comparison of Oncolytic Newcastle Disease Virus Strains"; *Proceedings of the American Association for Cancer Research Annual.*, vol. 36, p. 439 (1995).

Partial European Search Report; Application No./Patent No. 07016086.6-2107 dated Apr. 21, 2008.

Spradbrow, P.B., et al; "Oral Newcastle disease vaccination with V4 virus in chickens: Comparison with other routes"; *LIFESCI* (1991) XP-002237256 (Abstract).

Nema, S., et al; "Excipients and Their Use in Injectable Products"; *PDA Journal of Pharmaceutical Science and Technology*; vol. 51, No. 4 (1997) pp. 166-171, XP-009041329.

Schloer, G.M., et al; "Relationship of Plaque Size and Virulence for Chickens of 14 Representative Newcastle Disease Virus Strains"; *Journal of Virology*; vol. 2, No. 1 (1968) pp. 40-47, XP-002475731.

Sinkovics, J., et al; "New Developments in the Virus Therapy of Cancer: A Historical Review"; *Intervirology*, vol. 36, No. 4, (1993) pp. 193-214, XP-000982845.

Mer, David C., et al; "Immunological Studies of the Functions of Paramyxovirus Glycoproteins"; *Virology*, vol. 109, No. 1 (1981), pp. 94-105, XP-000647392.

Notice of Opposition to European Patent Application No./Patent No. 98949797.9-2107 / 1032269 dated Jun. 9, 2008 issued in corresponding Hong Kong Patent Application No. 00107775.6.

Reichard, Kirk W., et al; "Newcastle Disease Virus Selectively Kills Human Tumor Cells"; *Journal of Surgical Research*, vol. 32, No. 5 (1992), pp. 448-453, Appendix A (D3 dated May 29, 2008).

Daniel, M.D., et al; "Isolation and Characterization of Three Plaque-Type Clones of the Hickman Strain of Newcastle Disease Virus"; pp. 434-440, (1968) (D4 dated May 29, 2008).

Csatary, L.K., et al; "Annenuated Veterinary Virus Vaccine for the Treatment of Cancer"; *Cancer Detection and Prevention*; vol. 17, No. 6; pp. 619-627 (1993) (D5 dated May 29, 2008).

European Patent Application No. 98949797.9-2107, Response dated Jul. 14, 2005 (D7 dated May 29, 2008).

Kinderkrebsinfo.de (D8 dated May 29, 2008).

Foreign Patent DE3922444 (English Translation).

Notice of Opposition to European Patent Application No./Patent No. 98949797.9/1032269 dated Jun. 9, 2008. (English Translation).

Kinderkrebsinfo.de dated May 29, 2008. (English Translation).

Hanson Chapter 7, "Heterogeneity within strains of newcastle disease virus: key to survival"In Developments in Veterinary Virology, Newcastle Disease edited by D.J. Alexander (Kluwer Academic Publishers) 1998, pp. 113-130.

Spradrow "Epidemiology of Newcastle Disease and the economics of its control", In processing workshop of poverty eradication and promotion of gender equality Mar. 1999 pp. 171-173.

European Application No. 98949797.9, Response dated Jul. 14, 2005.

Proprietor's Reply to the Opposition against European Patent No. 1 032 269, Dec. 2008.

Minutes; Fact and Submissions; and Reason for the Decision in the opposition proceedings of European Patent No. 1032269, Apr. 2010.

Opposition Appeal Brief against European Patent No. 1 032 269, Aug. 2, 2010. (German Language).

Opposition Appeal Brief against European Patent No. 1 032 269, Aug. 2, 2010. (English Language).

Foreign Patent JP 10-5342 (English Language).

Beattie et al., "Vaccinia virus-encoded eIF-2 alpha homolog abrogates the antiviral effect of interferon", Virology, (1991) 183(1):419-22.

Foreign Patent DE3922444 (English Translation), (1991).

Chu, et al., "Hydroxylamine mutagenesis of HSV DNA and DNA fragments: introduction of mutations into selected regions of the viral genome", Virology, 98:168-81, 1979.

Coen, et al., "Thymidine kinase-negative herpes simplex virus mutants establish latency in mouse trigeminal ganglia but do not reactivate", Proc. Natl. Acad. Sci. USA, 86: 4736-4740, Jun. 1989.

Opposition against European Patent No. 1 032 269, Apr. 2009. (German Language).

Opposition against European Patent No. 1 032 269, Apr. 2009. (English Translation).

Preliminary non-binding opinion of opposition division for European Patent No. 1 032 269, Oct. 2009.

Lorence, et al., "Phase 1 clinical experience using intravenous administration of PV701, an oncolytic Newcastle disease virus", Curr Cancer Drug Targets,7:157-167, 2007.

Skeel, Chapter 1: Biologic and Pharmacologic Basis of Cancer Chemotherapy and Biotherapy, Handbook of Cancer Chemotherapy, 7th ed. Lippincott Williams & Wikins, 2007, pp. 1-31.

Mendel, et al., "Oral Administration of a Prodrug of the Influenza Virus Neuraminidase Inhibitor GS 4071 Protects Mice and Ferrets against Influenza Infection", Antimicrobial Agents and Chemotherapy, 42(3): 640-646, Mar. 1998.

Elkin, et al., "The effect of changes in tumor size on breast carcinoma survival in the U.S.: 1975-1999", Cancer,104(6): 1149-57, 2005.

Kiesslich, et al., "Colonoscopy, Tumors, and Inflammatory Bowel Disease—New Diagnostic Methods"; Endoscopy, 38: 5-10, 2006.

Wisnivesky, et al., "The Effect of Tumor size on Curability of Stage 1 Non-Small Cell Lung Cancers", Chest: 126: 761-765 (Sep. 2004). (Abstract and Introduction only).

CBS News; Healthwatch; "Cancer Survival Tied to Tumor Size"; Aug. 7, 2005, p. 1.

Lorence, et al., "Systemic Therapy of Human Tumor Xenografts using PV701, an Oncolytic Strain of Newcastle Disease Virus, in Combination with a Cytotoxic Drug Demonstrates at least Additive Antitumor Responses", Poster #5428, AACR Meeting, San Francisco, 2002.

Felzmann, et al., "Characterization of the antitumor immune response generated by treatment of murine tumors with recombinant adenoviruses expressing HSVtk, IL-2 , IL-6 or B7-1", Gene Therapy, Dec. 1997; 4(12):1322-9, 1 page. Abstract.

Topf, et al., "Regional 'pro-drug' gene therapy: intravenous administration of an adenoviral vector expressing the E. coli cytosine deaminase gene and systemic administration of 5-fluorocystosine suppresses growth of hepatic metastasis of colon carcinoma"; Gene Therapy, Apr. 1998, 5(4):507-13; 1 page. Abstract.

Knezic, et al., "Constitutive interferon expression from retroviral vector", Antiviral Res.; 1993, 22(2-3):215-21, 1 page. Abstract.

Garcia-Sanchez, et al., "Cytosine Deaminase Adenoviral Vector and 5-Fluorocytosine Selectively Reduce Breast Cancer Cells 1 Million-Fold when they Contaminate Hematopoietic Cells: A Potential Purging Method for Autologous Transplantation", Blood, 92(2): 672-682, Jul. 15, 1998.

Bradshaw, Jr., et al., "Human Thymidine Kinase Gene: Molecular Cloning and Nucleotide Sequence of a cDNA Expressible in Mammalian Cells", Molecular and Cellular Biology; 4(11): 2316-2320, Nov. 1984.

Goeddel, et al., "Synthesis of human fibroblast interferon by E. coli", Nucleic Acids Research, 8(18):4057-4074, 1980.

Fiola, et al., "Tumor selective replication of Newcastle Disease Virus: Association with defects of tumor cells in antiviral defence"; Int. J. Cancer, 119: 328-338, 2006.

Moriuchi, et al., "Double suicide gene therapy using a replication defective herpes simplex virus vector reveals reciprocal interference in a malignant glioma model", Gene Therapy, 9: 584-591, 2002.

Wise, et al., "Development of a Real-Time Reverse-Transcription PCR for Detection of Newcastle Disease Virus RNA in Clinical Samples", Journal of Clinical Microbiology; 42(1): 329-338, 2004.

Marino, et al., "Cellular and Humoral Response of in Ovo-Bursectomized Chickens to Experimental Challenge with Velogenic Newcastle Disease Virus", Avian Diseases, 31(2): 293-301, 1987.

Gelb, Jr., et al., "Detergent-Treated Newcastle Disease Virus as an Agar Gel Precipitin Test Antigen", Poult Sci., 66(5): 845-853,1987.

PPMK 107 is a clonal Virus; 1 page.

Seal, et al., "Phylogenetic Relationships among Highly Virulent Newcastle Disease Virus Isolates Obtained from Exotic Birds and Poultry from 1989 to 1996", J. of Clinical Microbiology, 36(4): 1141-1145, Apr. 1998.
Berinstein, et al., "Use of a Heteroduplex Mobility Assay to Detect Differences in the Fusion Protein Cleavage Site Coding Sequence among Newcastle Disease Virus Isolates", J. of Clinical Microbiology, 39(9): 3171-3178, 2001.
Al-Garib, et al., "Detection of Antibody-Forming Cells Directed against Newcastle Disease Virus and their Immunoglobulin Class by double Immunoenzyme Histochemistry", Avian Diseases, 47: 453-457, 2003.
Harfast, et al., "Interactions Between Human Lymphocytes and Paramyxovirus-Infected Cells: Adsorption and Cytotoxicity", The Journal of Immunology; 118(4): 1132-1137, Apr. 1977.
Ballagi-Pordany, et al., "Identification and grouping of Newcastle disease virus strains by restriction site analysis of a region from the F gene", Arch. Virol., 141: 243-261, Feb. 1996.
Schirrmacher, et al., "Newcastle Disease Virus Activates macrophages for anti-tumor activity", Int'l J. Oncology, 16: 363-375, 2000.
Sharkey, et al., "Experience in Surgical Pathology with Human Tumor Growth in the Nude Mouse", The Nude Mouse in Experimental and Clinical Research, Academic Press, Chapter 10: 187-214, 1978.
National Cancer Institute's complementary and alternative medicine (CAM) on NDV, pp. 1-47. 2004.
Orkin, et al., Report and Recommendations of the Panel to assess the NIH investment in Research on Gene Therapy, pp. 1-41, 1995.
Marshall, "Gene Therapy's Growing Pains", Science, 269: 1050-1055, 1995.
Balachandran, et al., "Oncolytic Activity of Vesicular Stomatitis Virus is Effective against Tumors Exhibiting Abberrant p53, Ras, or Myc Function and involves the Induction of Apoptosis", Journal of Virology, 75(7): 3474-3479, 2001.
Giedlin, et al., "Vesicular stomatitis virus: an exciting new therapeutic oncolytic virus candidate for cancer or just another chapter from Field's Virology?" Cancer Cell 4:241-243, 2003.
Rudd, et al., "Correlation between interferon sensitivity of reovirus isolates and ability to discriminate between normal and Ras-transformed cells"; J of Gen. Virol., 86:1489-1497, 2005.
Ishitsuka, et al., "A Simple and Efficient Microassay Method for Titration of Interferon". Microbiol Immunol., 21(10): 583-591, 1977.
Powell, et al., "Antibodies to Newcastle Disease Virus in Various Human Diseases", Int. Archs Allergy Appl. Immun., 76:331-335, 1985.
Haung, et al., "Nonspecific Innate Immunity Against *Escherichia coli* Infection in Chickens Induced by Vaccine Strains of Newcastle Disease Virus", Avian Disease, 44: 790-796, 2000.
Foreign Patent JP 10-5342 (English Language), (1998).
Beattie et al., "Vaccinia virus-encoded eIF-2 alpha homolog abrogates the antiviral effect of interferon", Virology, (1991) 183(1):419-22.
Stiehm, et al; "UCLA conference; Interferon: immunobiology and clinical significance"; *Ann Intern Med*.; (Jan. 1982).
Mullen, J.T.; The Oncologist, vol. 7; pp. 106-119, 109 (2002).
Sinkovics, J., et al; D1, "New Developments in the Virus therapy of Cancer: A Historical Review"; *Intervirology*; vol. 36; pp. 193-214 (1993).
D2, *Journal of Preventive Veterinary Medicine*; 3 (general No. 94); pp. 21-24 (1997); (English Language Translation).
Chou, J., et al; "Association of a $M_r$ 90,000 phosphoprotein with protein kinase PKR in cells exhibiting enhanced phosphorylation of translation initiation factor eIF-2$\alpha$ and premature shutoff of protein synthesis after infection with $_{\gamma1}34.5^-$ mutants of herpes simplex virus 1"; *Proc.Natl. Acad. Sci*; vol. 92; pp. 10516-10520 (1995).
Official Action dated Apr. 16, 2004 in co-pending U.S. Appl. No. 08/260,536, filed Jun. 16, 1994.
Colamonici, O.R. et al.; "Complementation of the Interferon $\alpha$ Response in Resistant Cells by Expression of the Cloned Subunit of the Interferon $\alpha$ Receptor"; *The Journal of Biological Chemistry*; vol. 269, No. 13, pp. 9598-9602 (1994).
Kolla, V, et al; "Modulation of Interferon (IFN)-inducible Gene Expression by Retinoic Acid"; *The Journal of Biological Chemistry*; vol. 271, No. 18, pp. 10508-10514 (1996).
Chen, H.-Y. et al; "Resistance to Interferon of a Human Adenocarcinoma Cell Line, HEC-1, and its Sensitivity to Natural Killer Cell Action"; *J. Gen. Virol*.; vol. 52, pp. 177-181 (1981).
Gomi, K., et al; "Analysis of Receptors, Cell Surface Antigens, and Proteins in Human Melanoma Cell Lines Resistant to Human Recombinant $\beta$- or $\gamma$-Interferon"; *Cancer Research*; vol. 46, pp. 6211-6216 (1986).

Improta, T., et al; "Interferon-γ Potentiates the Antiviral Activity and the Expression of Interferon-Stimulated Genes Induced by Interferon-α in U937 Cells"; *Journal of Interferon Research*; vol. 12, pp. 87-94 (1992).

James, C.D., et al; "Chromosome 9 Deletion Mapping Reveals Interferon α and Interferon β-1 Gene Deletions in Human Glial Tumors"; *Cancer Research*; vol. 51, pp. 1684-1688 (1991).

Linge, C., et al; "Interferon System Defects in Human Malignant Melanoma"; *Cancer Research*; vol. 55, pp. 4099-4104 (1995).

Meyskens, F.L., Jr.; "Relation of In Vitro Colony Survival to Clinical Response in a Prospective Trial of Single-Agent Chemotherapy for Metastatic Melanoma"; *Journal of Clinical Oncology*; vol. 2, No. 11, pp. 1223-1228 (1984).

Morikawa, K., et al; "Isolation of Human Colon Carcinoma Cells for Resistance to a Single Interferon Associated with Cross-Resistance to Multiple Recombinant Interferons: α, β, and γ"; *Journal of the National Cancer Institute*; vol. 82, No. 6, pp. 517-522 (1990).

Schiller, J.H., et al; "Antiproliferative Effects of Interferons on Human Melanoma Cells in the Human Tumor Colony-Forming Assay"; *Journal of Interferon Research*; vol. 6, pp. 615-625 (1986).

Sun, W.H., et al; "Interferon-α Resistance in a Cutaneous T-Cell Lymphoma Cell Line is Associated with Lack of STAT1 Expression"; *Blood*; vol. 91, No. 2, pp. 570-576 (1998).

Xu, B., et al; "Primary Leukemia Cells Resistant to α-Interferon In Vitro Are Defective in the Activation of the DNA-Binding Factor Interferon-Stimulated Gene Factor 3"; *Blood*; vol. 84, No. 6; pp. 1942-1949 (1994).

Ahlert, T., et al; "Isolation of a Human Melanoma Adapted Newcastle Disease Virus Mutant with Highly Selective Replication Patterns"; *Cancer Research*; vol. 50, pp. 5962-5968 (1990).

Andreansky, S.S., et al; "The Application of Genetically Engineered Herpes Simplex Viruses to the Treatment of Experimental Brain Tumors"; *Proc. Natl. Acad. Sci.*; Colloquium Paper; vol. 93, pp. 11313-11318 (1996).

Arroyo, P.J., et al; "Active Specific Immunotherapy with Vaccinia Colon Oncolysate Enhances the Immunomodulatory and Antitumor Effects of Interleukin-2 and Interferon α in a Murine Hepatic Metastasis Model"; *Cancer Immunol Immunother*; vol. 31, pp. 305-311 (1990).

Asada, T.; "Treatment of Human Cancer with Mumps Virus"; *Cancer*; vol. 34; pp. 1907-1928 (1974).

Balachandran, S., et al; "Activation of the dsRNA-Dependent Protein Kinase, PKR, Induces Apoptosis Through FADD-Mediated Death Signaling"; *The EMIBO Journal*; vol. 17, No. 23, pp. 6888-6902 (1998).

Balachandran, S., et al; "Vesicular Stomatitis Virus (VSV) Therapy of Tumors"; *Life*; vol. 50, pp. 135-138 (2000).

Barber, G.N., et al; "The 58-kilodalton Inhibitor of the Interferon-Induced Double-Stranded RNA-Activated Protein Kinase is a Tetratricopeptide Repeat Protein with Oncogenic Properties"; *Proc. Natl. Acad. Sci.*; vol. 91, pp. 4278-4282 (1994).

Bart, R.S., et al; "Role of Interferon in the Anti-Melanoma Effects of Poly (I).Poly (C) and Newcastle Disease Virus"; *Nature New Biology*; vol. 245; pp. 229-230 (1973).

Beattie, E., et al; "Host-Range Restriction of Vaccina Virus E3L-Specific Deletion Mutants"; *Virus Genes*; vol. vol. 12, No. 1, pp. 89-94 (1996).

Beverley, P.C.L., et al; "Immune Responses in Mice to Tumour Challenge After Immunization with Newcastle Disease Virus-Infected or X-Irradiated Tumor Cells or Cell Fractions"; *Int. J. Cancer*; vol. 11, pp. 212-223 (1973).

Bischoff, J.R., et al; "An Adenovirus Mutant That Replicates Selectively in p53-Deficient Human Tumor Cells"; *Science*; vol. 274; pp. 373-376 (1996).

Blaese, R.M., et al; "In situ Delivery of Suicide Genes for Cancer Treatment"; *European Journal of Cancer*; vol. 30A, No. 8; pp. 1193-1201 (1994).

Bluming, A.Z., et al; "Regression of Burkitt's Lymphoma in Association with Measles Infection"; *The Lancet*; pp. 105-106 (1971).

Bohle, W., et al; "Postoperative Active Specific Immunization in Colorectal Cancer Patients with Virus-Modified Autologous Tumor-Cell Vaccine"; *Cancer*; vol. 66, No. 7, pp. 1517-1523 (1990).

Buller, R.M.L., et al; "Cell Proliferative Response to Vaccinia Virus is Mediated by VGF"; *Virology*, vol. 164; pp. 182-192 (1988).

Buller, R.M.L., et al; "Decreased Virulence of Recombinant Vaccinia Virus Expression Vectors is Associated with a Thymidine Kinase-Negative Phenotype"; *Nature*, vol. 317, pp. 813-815 (1985).

Cassel, W.A., et al; "Newcastle Disease Virus as an Antineoplastic Agent"; *Cancer*; vol. 18; pp. 863-868 (1965).

Cassel, W.A., et al; "A Phase II Study on the Postsurgical Management of Stage II Malignant Melanoma with a Newcastle Disease Virus Oncolysate"; *Cancer*; vol. 52, pp. 856-860 (1983).

Cassel, W.A., et al; "A Ten-Year Follow-up on Stage II Malignant Melanoma Patients Treated Postsurgically with Newcastle Disease Virus Oncolysate"; *Med. Oncol. & Tumor Pharmacother.*; vol. 9, No. 4, pp. 169-171 (1992).

Chambers, R., et al; "Comparison of Genetically Engineered Herpes Simplex Viruses for the Treatment of Brain Tumors in a *scid* Mouse Model of Human Malignant Glioma"; *Proc. Natl. Acad. Sci.*; vol. 92; pp. 1411-1415 (1995).

Child, S.J., et al; "Insertional Inactivation of the Large Subunit of Ribonucleotide Reductase Encoded by Vaccinia Virus is Associated with Reduced Virulence in Vivo"; *Virology*; vol. 174, pp. 625-629 (1990).

Chou, J., et al; "Association of a $M_r$ 90,000 Phosphoprotein with Protein Kinase PKR in Cells Exhibiting Enhanced Phosphorylation of Translation Initiation Factor eIF-2α and Premature Shutoff of Protein Synthesis after Infection with $_{\gamma 1}34.5^-$ Mutants of Herpes Simplex Virus 1"; *Proc. Natl. Acad. Sci.*; vol. 92, pp. 10516-10520 (1995).

Clark, H.F., et al; "Protective Effect of WC3 Vaccine Against Rotavirus Diarrhea in Infants During a Predominantly Serotype 1 Rotavirus Season"; *The Journal of Infectious Diseases*; vol. 158, No. 3; pp. 570-587 (1988).

Cotran, R.S., et al; "Kinetics of Tumor Cell Growth"; *Robbins Pathologic Basis of Disease*, $4^{th}$ Edition; pp. 251-253 (1989).

Csatary, L.K., et al; "Attenuated Veterinary Virus Vaccine for the Treatment of Cancer"; *Cancer Detection and Prevention*; vol. 17, No. 6; pp. 617-627 (1993).

Csatary, L.K.; "Viruses in the Treatment of Cancer"; *The Lancet*; pp. 825-826 (1971).

Csatary, L.K. et al; "Virus Vaccines for the Treatment of Cancer"; *Orvosi Hetilap*; vol. 131; pp. 2585-2588 (1990).

Durbin, J.E., et al; "Targeted Disruption of the Mouse *Stat1* Gene Results in Compromised Innate Immunity to Viral Disease"; *Cell*; vol. 84, pp. 443-450 (1996).

Eaton, M.D., et al; "Contribution of Antiviral Immunity to Oncolysis by Newcastle Disease Virus in a Murine Lymphoma"; *Journal of the National Cancer Institute*; vol. 39, No. 6, pp. 1089-1097 (1967).

Eaton, M.D., et al; "Autoimmunity Induced by Injection of Virus-Modified Cell Membrane Antigens in Syngeneic Mice"; vol. 15, No. 1; pp. 322-329 (1977).

Izbicka, et al; "Effects of ONYX Adenovirus Preparations on Human Tumor Colony Forming Units"; *Proceedings of ASCO*; vol. 16; p. 433a; Abstract 1554 (1997).

James, C.D., et al; "Chromosome 9 Deletion Mapping Reveals Interferon α and Interferon β-1 Gene Deletions in Human Glial Tumors"; *Cancer Research*; vol. 51, pp. 1684-1688 (1991).

Joklik, W.K.; "Interferons"; *Virology*; pp. 383-410 (1990).

Kalvakolanu, D.V.R., et al; "Differentiation-Dependent Activation of Interferon-Stimulated Gene Factors and Transcription Factor NF-κB in Mouse Embryonal Carcinoma Cells"; *Proc. Natl. Adac. Sci.*; vol. 90, pp. 3167-3171 (1993).

Katze, M.G.; "Regulation of the Interferon-Induced PKR: Can Viruses Cope?"; *Trends in Microbiology*; vol. 3, No. 2; pp. 75-78 (1995).

Kenney, S., et al.; "Viruses as Oncolytic Agents: a New Age for "Therapeutic" Viruses?"; *Journal of the National Cancer Institute*; vol. 86, No. 16, Editorial Issue; pp. 1185-1186 (1994).

Kerr, S.M., et al; "Vaccinia DNA Ligase Complements *Saccharomyces cerevisiae cdc9*, Localizes in Cytoplasmic Factories and Affects Virulence and Virus Sensitivity to DNA Damaging Agents"; *The EMBO Journal*; vol. 10, No. 13; pp. 4343-4350 (1991).

Kirchner, H.H., et al; "Adjuvant Treatment of Locally Advanced Renal Cancer with Autologous Virus-Modified Tumor Vaccines"; *World J Urol*; vol. 13; pp. 171-173 (1995).

Kirn, D.H., et al; "Replicating Viruses as Selective Cancer Therapeutics"; *Molecular Medicine Today*; PH:S1357-4310(96)10050-2; pp. 519-527 (1996).

Kirn, et al; "ONYX-015, A Selectively Replicating Adenovirus, Has Antitumoral Activity Following IV Administration Alone and in Combination with Chemotherapy"; *Proceedings of ASCO*; vol. 16, p. 437a; Abstract 1564 (1997).

Kirn, et al; "ONYX-015 Selectively Replicates in and Lyses Cells Lacking Functional Small p53"; *Proceedings for the American Association for Cancer Research*; vol. 37; p. 352; Abstract 2400 (1996).

Korth, M.J., et al; "Cloning, Expression, and Cellular Localization of the Oncogenic 58-kDa Inhibitor of the RNA-Activated Human and Mouse Protein Kinase"; *Gene*; vol. 170, pp. 181-188 (1996).

Linge, C., et al; "Interferon System Defects in Human Malignant Melanoma"; *Cancer Research*; vol. 55, pp. 4099-4104 (1995).

Lorence, R.M., et al; "Complete Regression of Human Fibrosarcoma Xenografts after Local Newcastle Disease Virus Therapy"; *Cancer Research*; vol. 54; pp. 6017-6021 (1994).

Lorence, R.M., et al; "Newcastle Disease Virus as an Antineoplastic Agent: Induction of Tumor Necrosis Factor-α and Augmentation of Its Cytotoxicity"; *Journal of the National Cancer Institute*; vol. 80, No. 16, pp. 1305-1313 (1988).

Lorence, R.M., et al; "Complete Regression of Human Neuroblastoma Xenografts in Athymic Mice After Local Newcastle Disease Virus Therapy"; *Journal of the National Cancer Institute*; vol. 86, No. 16; pp. 1228-1233 (1994).

Machida, H., et al; "Effect of Nucleosides on Interferon Production and Development of Antiviral State Induced by Poly I Poly C"; *Microbiol. Immunol.*; vol. 23, No. 7; pp. 643-650 (1979).

Maeda, A., et al; "Isolation and Characterization of Defective Interfering Particle of Newcastle Disease Virus"; *Microbiol. Immunol.*; vol. 22, No. 12, pp. 775-784 (1978).

Maheshwari, R.K., et al; "Low Infectivity of Vesicular Stomatitis Virus (VSV) Particles Released from Interferon-Treated Cells is Related to Glycoprotein Deficiency"; *Biochemical and Biophysical Research Communications*; vol. 117, No. 1, pp. 161-168; (1983).

Martuza, R.; "Novel Treatment Approach for Malignant Brain Tumors Developed at Georgetown"; *Examiner; Georgetown University Medical Center*; pp. 1-8 (1995).

Martuza, R.L., et al; "Experimental Therapy of Human Glioma by Means of a Genetically Engineered Virus Mutant"; *Science*; vol. 252; pp. 853-856 (1991).

Mathews, M.B., et al; "Adenovirus Virus-Associated RNA and Translation Control"; *Journal of Virology*; vol. 65, No. 11; pp. 5657-5662 (1991).

Meignier, B., et al; In Vivo Behavior of Genetically Engineered Herpes Simplex Viruses R7017 and R7020. II. Studies in Immunocompetent and Immunosuppressed Owl Monkeys (*Aotus trivirgatus*); *The Journal of Infectious Diseases*; vol. 162; pp. 313-321 (1990).

Mineta, T., et al; "Attenuated Multi-Mutated Herpes Simplex Virus-1 for the Treatment of Malignant Gliomas"; *Nature Medicine*; vol. 1, No. 9; pp. 938-943 (1995).

Murray, D.R., et al; "Viral Oncolysate in the Management of Malignant Melanoma"; *Cancer*; vol. 40, No. 2, pp. 680-686 (1977).

Murphy, F.A., et al; "Virus Taxonomy"; *Virology*; Second Edition; vol. 1; Chapter 2; pp. 9-35 (1990).

Nickels, M.S., et al; "Identification of an Amino Acid Change that Affects N Protein Function in Vesicular Stomatitis Virus"; *Journal of General Virology*; vol. 75, pp. 3591-3595 (1994).

Pasquinucci, G.; "Possible Effect of Measles on Leukemia"; *The Lancet*; p. 136 (1971).

Pennisi, E.; "Will a Twist of Viral Fate Lead to a New Cancer Treatment?"; *Science*; vol. 274, pp. 342-343 (1996).

Peplinski, G.R., et al; "Prevention of Murine Breast Cancer by Vaccination with Tumor Cells Modified by Cytoline—Producing Recombinant Vaccinia Viruses"; *Annals of Surgical Oncology*; vol. 3, No. 1; pp. 15-23 (1996).

Perkus, M.E., et al; "Deletion of 55 Open Reading Frames from the Termini of Vaccinia Virus"; *Virology* vol. 180; pp. 406-410 (1991).

Petricoin III, E., et al; "Human Cancer Cell Lines Express a Negative Transcriptional Regulator of the Interferon Regulatory Factor Family of DNA Binding Proteins"; *Molecular and Cellular Biology*; vol. 14, No. 2, pp. 1477-1486 (1994).

Reichard, K.W., et al; "Newcastle Disease Virus Selectively Kills Human Tumor Cells"; *Journal of Surgical Research*; vol. 52, pp. 448-453 (1992).

Restifo, N.P., et al; "A Nonimmunogenic Sarcoma Transduced with the cDNA for Interferon γ Elicits CD8+ T Cells against the Wild-type Tumor: Correlation with Antigen Presentation Capability"; *The Journal of Experimental Medicine*; vol. 175, pp. 1423-1431 (1992).

Rodriguez, R., et al; "Prostate Attenuated Replication Competent Adenovirus (ARCA) CN706: A Selective Cytotoxic for Prostate-Specific Antigen-Posititve Prostate Cancer Cells"; *Cancer Research*; vol. 57; pp. 2559-2563 (1997).

Rosenbergová, M., et al; "Purification of Newcastle Disease Virus by Chromatography on Controlled-Pore Glass Bead Column"; *Acta Virol.*; vol. 25, pp. 31-35 (1981).

Rukavishnikova, G.E., et al; "Some Immunological Mechanisms of the Influenza Virus Antitumour Effect"; *Acta Virol.*; vol. 20, pp. 387-394 (1976).

Schirrmacher, V., et al; "Successful Application of Non-Oncogenic Viruses for Antimetastatic Cancer Immunotherapy"; *Institut for Immunologic Und Genetik AM Deutschen Krebsforschungszentrum*, 6900 Heidelberg, Germany; pp. 19-49 (1986).

Schloer, G.M., et al; "Relationship of Plaque Size and Virulence for Chickens of 14 Representative Newcastle Disease Virus Strains"; *Journal of Virology*; vol. 2, No. 1; pp. 40-47 (1968).

Schnell, M.J., et al; "Construction of a Novel Virus that Targets HIV-1-Infected Cells and Controls HIV-1 Infection"; *Cell*; vol. 90; pp. 849-857 (1997).

Schubert, M., et al; "Primary Structure of the Vesicular Stomatitis Virus Polymerase (L) Gene: Evidence for a High Frequency of Mutations"; *Journal of Virology*; vol. 51, No. 2, pp. 505-514 (1984).

Shoham, J., et al; "Augmentation of Tumor Cell Immunogenicity by Viruses—An Approach to Specific Immunotherapy of Cancer"; *Nat Immun. Cell Growth Regul.*; vol. 9; pp. 165-172 (1990).

Shingu, M, et al; "Therapeutic Effects of Bovine Enterovirus Infection on Rabbits with Experimentally Induced Adult T Cell Leukaemia"; *Journal of General Virology*; vol. 72, pp. 2031-2034 (1991).

Sinkovics, J., et al; "New Developments in the Virus Therapy of Cancer: A Historical Review"; *Intervirology*; vol. 36; pp. 193-214 (1993).

Smith, R.R., et al; "Studies on the Use of Viruses in the Treatment of Carcignoma of the Cervix"; *Cancer*; vol. 9, pp. 1211-1218 (1956).

Spriggs, D.R., et al; "Attenuated Reovirus Type 3 Strains Generated by Selection of Haemagglutinin Antigenic Variants"; *Nature*; vol. 297; pp. 68-70 (1982).

Sreevalsan, T.; "Chapter 14 Biologic Therapy with Interferon-α and β: Preclinical Studies"; *Biologic Therapy of Cancer: Principles and Practice*; pp. 347-364.

Stojdl et al, Exploiting Tumor-Specific Defects in the Interferon Pathway with a Previously Unknown Oncolytic Virus; *Nature Medicine*, vol. 6, No. 7, pp. 821-825 (2000).

Stoner, G.D., et al; "Effect of Neuraminidase Pretreatment on the Susceptibility of Normal and Transformed Mammalian Cells to Bovine Enterovirus 261"; *Nature*; vol. 245; pp. 319-320 (1973).

Strube, M., et al; "Sensitivity of Ortho- and Paramyxovirus Replication to Human Interferon α"; *Molec. Biol. Rep.*; vol. 10, pp. 237-243 (1985).

Suskind, R.G., et al; "Viral Agents Oncolytic for Human Tumors in Heterologous Host. Oncolytic Effect of Coxsackie B. Viruses"; *Oncolytic Effect of Coxsackie Virus*; U.S Dept. of Health, Education & Welfare, N.I.H. Natl Institute of Allergy and Infectious Diseases, and Natl Cancer Inst., Bethesda, MD.; pp. 309-319; (22931) (1956).

Symons, J.A., et al; "Vaccinia Virus Encodes a Soluble Type I Interferon Receptor of Novel Structure and Broad Species Specificity"; *Cell*, vol. 81, pp. 551-560 (1995).

Tait, D.L., et al; "A Phase I Trial of Retroviral BRCA1sv Gene Therapy in Ovarian Cancer"; *Clinical Cancer Research*; vol. 3; pp. 1959-1968 (1997).

Takafuji, E.T., et al; "Simultaneous Administration of Live, Enteric-Coated Adenovirus Types 4, 7, and 21 Vaccines: Safety and Immunogenicity"; *Journal of Infectious Diseases*; vol. 140, No. 1; pp. 48-53 (1979).

Tanaka, N., et al; "Cellular Commitment to Oncogene-Induced Transformation or Apoptosis is Dependent on the Transcription Factor IRF-1"; *Cell*; vol. 77, pp. 829-839 (1994).

Tanaka, N., et al; "Immunotherapy of a Vaccinia Colon Oncolysate Prepared with Interleukin-2 Gene-Encoded Vaccinia Virus and Interferon-α Increases the Survival of Mice Bearing Syngeneic Colon Adenocarcinoma"; *Journal of Immunotherapy*; vol. 16, No. 4; pp. 283-293 (1994).

Taylor, M.W., et al; "Virus-Induced Regression of Tumor Growth"; *Journal of the National Cancer Institute*; vol. 44, No. 3; pp. 515-519 (1970).

Verma, I.M., et al; "Gene Therapy—Promises, Problems and Prospects"; *Nature*; vol. 389, pp. 238-242 (1997).

Wheelock, E.F., et al; "Observations on the Repeated Administration of Viruses to a Patient with Acute Leukemia"; *The New England Journal of Medicine*; vol. 271, No. 13; (1964).

Xu, B., et al; "Primary Leukemia Cells Resistant to α-Interferon in Vitro are Defective in the Activation of the DNA-Binding Factor Interferon-Stimulated Gene Factor 3"; *Blood*, vol. 84, No. 6, pp. 1942-1949 (1994).

Yu, et al; "Antiviral Action of Interferon-β on Newcastle Disease Virus: Selectivity to the Hemagglutinin-Neuraminidase Gene Expression"; *Med. Microbiol Immunol*; vol. 184, pp. 45-52 (1995).

Zhang, B.; "Process for Preparing Inducing Interferon of Human Body"; *Abstract (D4)*; *Espacenet Database-12*; Patent No. CN1054192 (1991).

Zhang, B.; "Attenuated Newcastle Disease Virus for Induction of Interferons to Combat Neoplasm or Viral Diseases"; (1991); Abstract 09; Database CAPLUS, on STN Columbus, OH: Chemical Abstract Service, DN 116: 104333, CN 1054192 A.

Zhang, J.F., et al; "Treatment of a Human Breast Cancer Xenograft with an Adenovirus Vector Containing an Interferon Gene Results in Rapid Regression Due to Viral Oncolysis and Gene Therapy"; *Proc. Natl. Acad. Sci.*; vol. 93, pp. 4513-4518 (1996).

Zhang, J.F., et al; "Gene Therapy with an Adeno-Associated Virus Carrying an Interferon Gene Results in Tumor Growth Suppression and Regression"; *Cancer Gene Therapy*, vol. 3, No. 1; pp. 31-38 (1996).

Zhang, W.W., et al; "High-Efficiency Gene Transfer and High-Level Expression of Wild-Type *p53* in Human Lung Cancer Cells Mediated by Recombinant Adenovirus"; *Cancer Gene Therapy*; vol. 1, No. 1, pp. 5-13 (1994).

Zhenxiang, H., et al; "Studies on Viral Immunotherapy of Ascitic Tumors in Mice—I. Results of Treatment on Viruses of Ehrlich and S180 Ascitic Tumor Cells"; vol. 6, No. 3; pp. 213-216 (1984).

Leonard, J.P. et al; "Effects of Single-Dose Interleukin-12 Exposure on Interleukin-12-Associated Toxicity and Interferon-γ Production"; *Blood*; vol. 90, No. 7, Oct. 1, 1997, pp. 2541-2548.

Stiehm, E.R., et al; "Interferon: Immunobiology and Clinical Significance"; *Annals of Internal Medicine*; 96, pp. 80-93 (1982).

Proceedings of the American Association for Cancer Research Annual. vol. 36; p. 439 (1995).

Okuno, Y. et al; "Studies on the use of mumps virus for treatment of human cancer"; Biken J., 1978, vol. 21, No. 2, pp. 37-49.

Ikeda, H., et al; "Detection of Heterozygous Mutation in the Retinoblastoma Gene in a Human Pituitary Adenoma Using PCR-SSCP Analysis and Direct Sequencing"; Endocr Pathol. 1995, vol. 66, pp. 189-196.

Zhang Bingtuan; "Process for Preparing Inducing Interferon of Human Body"; Sep. 1991; Abstract; (D4).

Gresser et al; "Inhibitory Effect of Interferon on Murine Sarcoma and Leukaemia Virus Infection in Vitro"; Nature, Nature, vol. 223, pp. 844-845; Aug. 1969.

Zhang, B.; "Attenuated newcastle disease virus for induction of interferons to combat neoplasm or viral diseases"; (1992); Chemical Abstracts 116:104333.

Pecora, et al, J. Clin. Oncol. (2002) 20(9): 2251-2266.

G.S. Reddy et al; "Use of BHK Cell Culture-Adapted Newcastle Disease Virus for Immunization of Chicks"; 1992; XP-002237247 (Abstract).

G.S. Reddy et al; "Comparison of Two Experimental Binary Ethylenimine Bei Inactivated Newcastle Disease Oil-Emulsion Vaccines"; 1991; XP-002237248 (Abstract).

J. Gelg Jr. et al; "Pathogenicity and Cross-Protection of Pigeon Paramyxovirus 1 and Newcastle Disease Virus in Young Chickens"; (1987); XP-002237249 (Abstract).

M.A. Shuaib et al; "Studies on the Development of Pelleted Newcastle Disease Virus Vaccine"; (1985); XP-002237250 (Abstract).

M.A. Al Imadi et al; "The Susceptibility of Domestic Waterfowl to Newcastle Disease Virus and Their Role in its Spread"; (1982) (Rec'd 1983); XP-002237251 (Abstract).

B. Rivetz et al; "Enzymatic Changes in Serum and Tissues in Fowl Infected with a Neurotropic Mesogenic Strain of Newcastle Disease Virus"; (1982); XP-002237252 (Abstract).

B. Lomniczi; "Properties of Nonneurovirulent Plaque Forming Mutants of Newcastle Disease Virus"; (1976); XP-002237253 (Abstract).

D.Y. Perey et al; "Host Resistance Mechanisms to Newcastle Disease Virus in Immunodeficient Chickens" (38540); (1975); XP-002237254 (Abstract).

I. Szeri, et al; "Effect of Microbial Immunomodulants on the Course of LCMV Infection in Old Mice with Thymus Involutin"; (1992); XP-002237255 (Abstract).

P.B. Spradbrow et al; "Oral Newcastle Disease Vaccination with V4 Virus in Chickens"; Aust. Vet. J., (1991) vol. 68, No. 3, pp. 114-115; XP-002237256; (Abstract).

Restifo, Nicholas P., et al, *The Journal of Experimental Medicine*, vol. 175, Jun. 1992, pp. 1423-1431, "A Nonimmunogenic Sarcoma Transduced with the cDNA for Interferon ( Elicits CD8+ T Cells against the Wild-type Tumor . . . Presentation Capability".

Buller, R.M.L., et al, *Nature*, vol. 317, Oct. 31, 1985, pp. 813-815, "Decreased virulence of recombinant vaccinia virus expression vectors is associated with a thymidine kinase-negative phenotype".

Haines, G.K., et al, *Virchows Archiv B Cell Pathol*, (1993) 63:289-295, "Correlation of the expression of double-stranded RNA-dependent protein kinase (p68) with differentiation in head and neck squamous cell carcinoma".

James, C. David, et al, *Cancer Research*, 51, pp. 1684-1688, Mar. 15, 1991, "Chromosome 9 Deletion Mapping Reveals Interferon ∀ and Interferon ∃-1 Gene Deletions in Human Glial Tumors".

Arroyo, Pedro J., et al, *Cancer Immunol Immunother*, (1990) 31:305-311, "Active specific immunotherapy with vaccinia colon oncolysate enhances the immunomodulatory and antitumor effects of interleukin-2 and inteferon ∀ in a murine hepatic metastasis model".

Zhang, Wei-Wei, et al, *Cancer Gene Therapy*, vol. 1, No. 1, 1994: pp. 5-13 "High-efficiency gene transfer and high-level expression of wild-type p53 in human lung cancer cells mediated by recombinant adenovirus".

Korth, Marcus, J., et al, *Gene*, 170 (1996) 181-188, "Cloning, expression, and cellular localization of the oncogenic 58-kDa inhibitor of the RNA-activated human and mouse protein kinase".

Barber, Glen N., et al, *Proc. Natl. Acad. Sci. USA*, vol. 91, pp. 4278-4282, May 1994 Biochemistry, "The 58-kilodalton inhibitor of the interferon-induced double-stranded RNA-activated protein kinase is a tetratricopeptide repeat protein with oncogenic properties".

Mathews, Michael B., et al, *Journal of Virology*, vol. 65, No. 11, Nov. 1991, p. 5657-5662, "Adenovirus Virus-Associated RNA and Translation Control".

Imani, Farhad, et al, *Proc. Natl. Acad. Sci. USA*, vol. 85, pp. 7887-7891, Nov. 1988 Biochemistry, "Inhibitory activity for the interferon-induced protein kinase is associated with the reovirus serotype . . . protein".

Tanaka, Nobuyuki, et al, *Journal of Immunotherapy*, vol. 16, No. 4 (1994) pp. 283-293, "Immunotherapy of a Vaccinia Colon Oncolysate Prepared with Interleukin-2 Gene-Encoded Vaccinia Virus and Interferon-∀ Increases the Survival of Mice Bearing Syngeneic Colon Adenocarcinoma".

Csatary M.D., Laszlo K., et al, *Cancer Detection and Prevention*, 17(6):619-627 (1993), "Attenuated Veterinary Virus Vaccine for the Treatment of Cancer".

Agent Cassel Ph.D, William A., et al, *Cancer*, vol. 18, No. 7, pp. 863-868, Jul. 1965, "Newcastle Disease Virus As an Antineoplastic".

Schirmacher, V., et al, *Institut For Immunologic Und Genetik Am Deutschen Krebsforchungszentrum*, 6900 Heidelberg, Germany, pp. 19-49, Mar. 13, 1986, "Successful application of non-oncogenic viruses for antimetastatic cancer immunotherapy".

Lorence, Robert M., et al, *Journal of the National Cancer Institute*, vol. 80, No. 16, Oct. 19, 1988, pp. 1305-1312, "Newcastle Disease Virus as an Antineoplastic Agent: Induction of Tumor Necrosis Factor-∀ and Augmented of Its Cytotoxicity".

Reichard, Kirk W., et al, *Journal of Surgical Research*, 52, 448-453 (1992), "Newcastle Disease Virus Selectively Kills Human Tumor Cells".

Eaton, Monroe D., et al, *Journal of the National Cancer Institute*, vol. 39, No. 6, Dec. 1967, pp. 1089-1097, "Contribution of Antiviral Immunity to Oncolysis by Newcastle Disease Virus in a Murine Lymphoma".

Beverley, P.C., et al, *Int. J. Cancer*, 11, 212-223 (1973), "Immune Responses in Mice to tumour Challenge After Immunization With NewCastle Disease Virus-Infected or X-Irradiated Tumour Cells or Cell Fractions".

Shoham, Jacob, et al, *Nat. Immun. Cell Growth Regul.*, 1990; 9:165-172, "Augmentation of Tumor Cell Immunogenicity by Viruses—An Approach to Specific Immunotherapy of Cancer".

Bart, Robert S., et al, *Nature New Biology*, vol. 245, No. 147, Oct. 24, 1973, pp. 229-230, "Role of Interferon in the Anti-Melanoma Effects of Poly(I).Poly (C) and Newcastle Disease Virus".

Sinkovics, Joseph, et al, *Intervirology*, 1993, 36:193-214, "New Developments in the Virus Therapy of Cancer: A Historical Review".

Murray, Douglas R., et al, *Cancer*, Aug. 1977, vol. 40, No. 2, pp. 680-686, "Viral Oncolysate in the Management of Malignant Melanoma".

Cassel, William A., *Cancer*, 52:856-860, Sep. 1, 1983, "A Phase II Study on the Postsurgical Management of Stag Malignant Melanoma With a Newcastle Disease Virus Oncolysate".

Cassel, William A., *Med. Oncol. & Tumor Pharmacother.*, vol. 9, No. 4, pp. 169-171, 1992, "A Ten-Year Follow-up on Stage II Magignant Melanoma Patients Treated Postsurgically with New Castle Disease Virus Oncolysate".

Bohle, MD, Wolfran, et al, *Cancer*, vol. 66, No. 7, pp. 1517-1523, Oct. 1, 1990 "Postoperative Active Specific Immunization in Colorectal Cancer Patients With Virus-Modified Autologous Tumor-Cell Vaccine".

Eaton, Monroe D., et al, *Infection and Immunity*, vol. 15, No. 1, Jan. 1977, pp. 322-328, "Autoimmunity Induced by Injection of Virus-Modified Cell Membrane Antigens in Syngeneic Mice".

Wheelock, M.D., E. Frederick, et al, *The New England Journal of Medicine*, vol. 271, No. 13, Sep. 24, 1964, pp. 645-651, "Observations on the Repeated Administration of Viruses to a Patient with Acute Leukemia".

*The Lancet*, Oct. 9, 1971, p. 825, "Viruses in the Treatment of Cancer".

Kenney, Shannon, et al, *JNCL Editorial* Issue 16, Jun. 20, 1997, pp. 1-3, "Viruses as Oncolytic Agents: A New Age for 'Therapeutic' Viruses?"

Rodriguez, Ron, et al, *Cancer Research*, 57, 2559-2563, Jul. 1, 1997, "Prostate Attenuated Replication Competent Adenovirus (ARCA) CN706: A Selective3 Cytotoxic for Prostate-specific Antigen-positive Prostate Cancer Cells".

Martuza, MD, Robert, *Examiner*, Oct. 1995, Georgetown University Medical Center, pp. 1-8, "Novel Treatment Approach for Malignant Brain Tumors Developed at Georgetown".

Mineta, Toshihiro, et al, *Nature Medicine*, vol. 1, No. 9, Sep. 1995, 938-943, "Attenuated Multi-Mutated Herpes Simplex Virus-1 for the Treatment of Malignant Gliomas".

Zhenxiang, Huang, et al, *ACTA Academiae Medicine Sinicae*, vol. 6, No. 3, Jun. 1984, "Studies on Viral Immunotherapy of Ascitic Tumors in Mice.—I. Results of Treatment on Viruses of Ehrlich and S180 Ascitic Tumor Cells" p. 213-216.

*Abstract*,1362, Ganly, et al, *Proceedings of ASCO*, vol. 16 (1997), p. 433a "Phase I Trial of Intratumoral Injection with an E1B-Attenuated Adenovirus, ONYX-015, in Patients with Recurrent p53(−) Head and Neck Cancer".

*Abstract*, 1564, Kirn, et al, *Proceedings of ASCO*, vol. 16 (1997), p. 433a "ONYX-015, A Selectively Replicating Adenovirus, Has Antitumoral Activity Following IV Administration Alone and in Combination with Chemotherapy".

*Abstract*,1554, Izbicka, et al, *Proceedings of ASCO*, vol. 16 (1997), p. 433a "Effects of ONYX Adenovirus Preparations on Human Tumor Colony Forming Units".

*Abstract*, 2400, Kirn, et al, *Proceedings for the American Association for Cancer Research*, vol. 37, Mar. 1996, p. 352 "ONYX-015 Selectively Replicates in and Lyses Cells Lacking Functional Small p53."

Field, H.J., et al, J. Hyg., Camb., 81, 267-277, (1978) "The pathogenicity of thymidine kinase-deficient mutants of herpes simplex virus in mice".

Ahlert, T., et al, Cancer Res. 50 (1990), pp. 5962-5968, "Isolation of a Human Melanoma Adapted Newcastle Disease Virus Mutant with Highly Selective Replication Patterns".

Malaczewska, et al, "Effect of KLP-602 on virus replication in cell cultures", Polish Journal of Veterinary Sciences, 7(2): 103-108, 2004.

Bergmann, et al., "A Genetically engineered Influenza A Virus with ras-Dependent Oncolytic Properties", Cancer Research, 61: 8188-8193, 2001.

Cascallo, et al., "Ras-dependent Oncolysis with an Adenovirus VAI Mutant", Cancer Research, 63: 5544-5550, 2003.

Lawson, et al., "Recombinant vesicular stomatitis viruses from DNA", Proc Natl Acad. Sci, 92: 4477-4481, 1995.

Povlsen, et al., "Status of Chemotherapy, Radiotherapy, Endocrine Therapy, and Immunotherapy Studies of Human Cancer in the Nude Mouse", The Nude Mouse in Experimental and Clinical Research, Academic Press, Chapter 19, pp. 437-456, 1978.

Thome, et al., "Future directions for the field of oncolytic virotherapy: a perspective on the use of vaccinia virus"; Expert Opin Biol Ther, 4(8): 1307-1321, 2004.

Masters, et al., "Mechanism of Interferon Action: Inhibition of Vesicular Stomatitis Virus Replication in Human Amnion U Cells by Cloned Human Leukocyte Interferon", The Journal of Biological Chemistry, 258(19): 12019-12025, 1983.

Samuel, et al., "Mechanism of Interferon Action", The Journal of Biligical Chemistry, 257(19): 11796-11801, 1982.

Hotte, et al., "Slow intravenous Infusion of PV701, an Oncolytic Virus: Final Results of a Phase 1 Study", Am. Soc. Clin. Oncol., 2004, 1 page.

Balachandran, et al., "Vesicular Stomatitis Virus (VSV) Therapy of Tumors", Life, 50:135-138, 2000.

Connor, et al., "Replication and Cytopathic Effect of Oncolytic Vesicular Stomatitis Virus in Hypoxic Tumor Cells in Vitro and in vivo", Journal of Virology, 78(17): 8960-8970, 2004.

Wollmann, et al., "Targeting Human Glioblastoma Cells: Comparison of Nine Viruses with Oncolytic Potential" Journal of Virology, 79(10): 6005-6022, 2005.

Ebert, et al., "Oncolytic Vesicular Stomatitis Virus for Treatment of Orthotopic Hepatocellular Carcinoma in Immune-competent Rats", Cancer Research, 63: 3605-3611, 2003.

Shinozaki, et al., "Oncolysis of Multifocal Hepatocellular Carcinoma in the Rat Liver by Hepatic Artery Infusion of Vesicular Stomatitis Virus", Molecular Therapy, 9(3): 368-376, 2004.

Li, et al., "Induction of Apoptosis and Tumor Regression by Vesicular Stomatitis Virus in the Presence of Gemcitabine in Lung Cancer", Int. J. Cancer, 112: 143-149, 2004.

Huang, et al., "Oncolysis of Hepatic Metastasis of Colorectal Cancer by Recombinant Vesicular Stomatitis Virus in Immune-Competent Mice", Molecular Therapy, 8(3): 434-440, 2003.

Shinozaki, et al., "Eradication of Advanced Heptocellular Carcinoma in Rats via Repeated Hepatic Arterial Infusions of Recombinant VSV", Hepatology, 41(1): 196-203, 2005.

Shinozaki, et al., "Treatment of multi-focal colorectal carcinoma metastatic to the liver of immune-competent and syngeneic rats by hepatic artery infusion of oncolytic vesicular stomatitis virus", Int. J. Cancer, 114: 659-664, 2005.

Fernandez, et al., "Genetically engineered Vesicular Stomatitis Virus in Gene Therapy: Application for Treatment of Malignant Disease", Journal of Virology, 76(2): 895-904, 2002.

Scanlon, et al., "Pathotyping isolates of Newcastle disease virus using antipeptide antibodies to pathotype-specific regions of the fusion and hemagglutinin-neuraminidase proteins", Arch. Virol, 144:55-72, 1999.

Porosnicu, et al., "The Oncolytic Effect of Recombinant Vesicular Stomatitis Virus is Enhanced by Expression of the Fusion Cytosine Deaminase/Uracil Phosphoribosyltransferase Suicide Gene", Cancer Research, 63: 8366-8376, 2003.

Obuchi, et al., "Development of Recombinant Vesicular Stomatitis Viruses that Exploit Defects in Host Defense to Augment Specific Oncolytic Activity", Journal of Virology, 77(16): 8843-8856, 2003.

Stodjl, et al., VSV strains with defects in their ability to shutdown innate immunity are potent systemic anti cancer agents, Cancer Cell, 4: 263-275, 2003.

Ahmed, et al., Sensitivity of prostate tumors to wild type and M protein mutant vesicular stomatitis viruses; Virology, 330: 34-49, 2004.

Ebert, et al., Systemic therapy of experimental breast cancer metastases by mutant vesicular stomatitis virus in immune-competent mice, Cancer Gene Therapy, 12: 350-358, 2005.

Stojdl, et al., "Exploiting tumor-specific defects in the interferon pathway with a previously unknown oncolytic virus", Nature Medicine, 6(7): 821-825, 2000.

Bennett, et al., "The production of fever by influenzal viruses", J Exp. Med., 90:335-347, 1949.

Proprietor's Reply of Jan. 2010 in the Opposition proceedings of European Patent No. 1 032 269.

Garcia-Sastre, et al., "Genetic manipulation of negative-strand RNA virus genomes", Annu. Rev. Microbiol., 47:765-90, 1993.

Sambrook, et al., Molecular Cloning, A Laboratory manual, 2nd Ed. Cold Spring Harbor Laboratory Press, 1989, pp. 2.60-2.66.

Opponent's Reply of Jan. 2010 in the opposition proceedings of European Patent No. 1 032 269. (German Language).

Opponent's Reply of Jan. 2010 in the opposition proceedings of European Patent No. 1 032 269. (English Translation).

\* cited by examiner

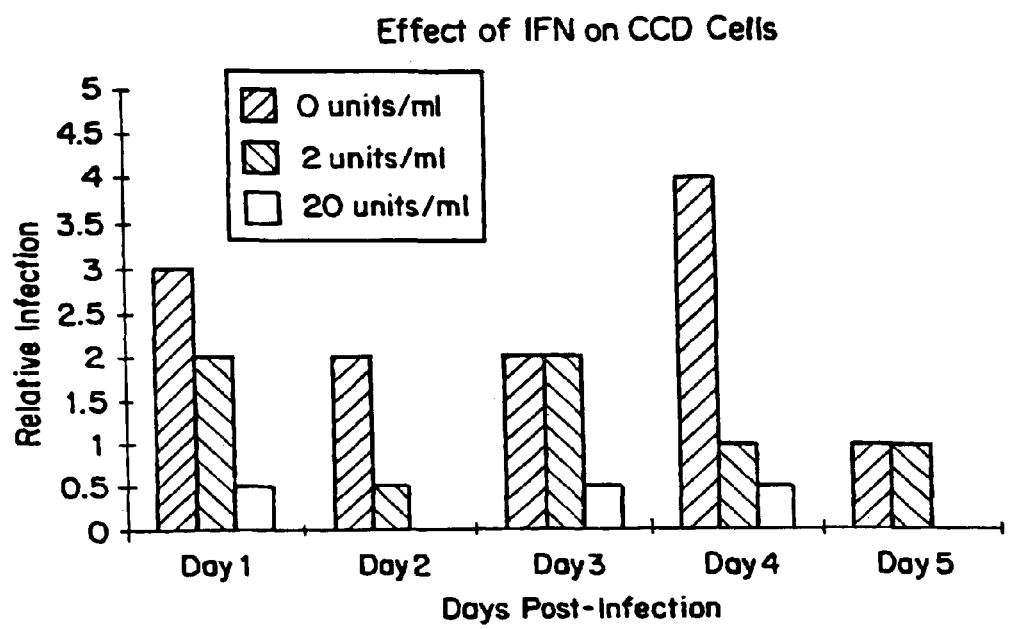
FIG. 3A Effect of IFN on CCD Cells
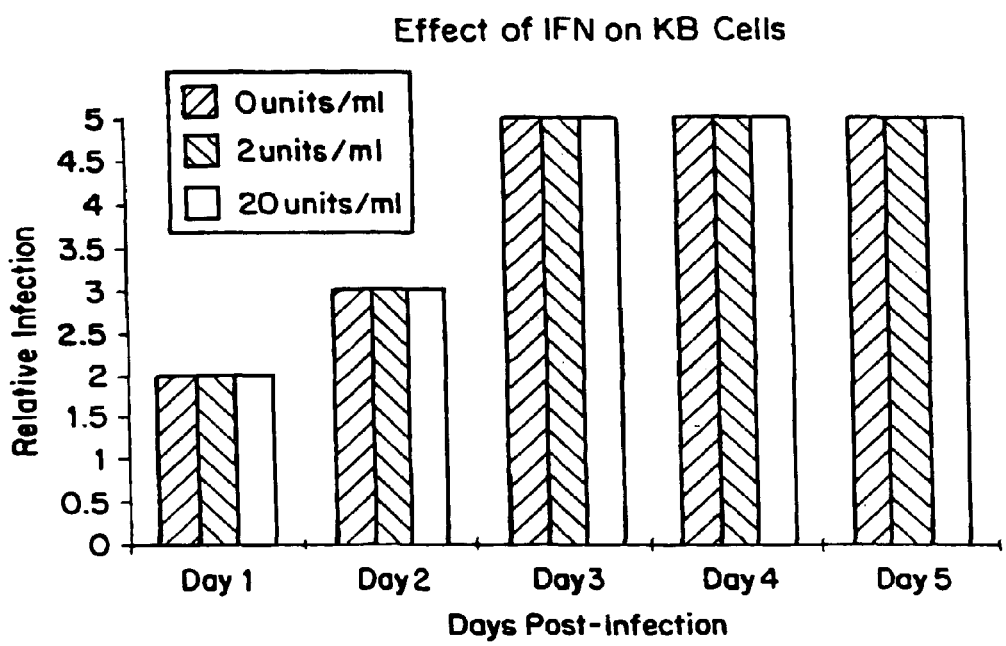
FIG. 3B Effect of IFN on KB Cells

TREATMENT OF NEOPLASMS WITH VIRUSES

This application is a divisional of application Ser. No. 10/044,955, filed Jan. 15, 2002 now abandoned, which is a continuation of application Ser. No. 09/168,883, Oct. 9, 1998 now abandoned, which is a CIP of 08/948,244 filed Oct. 9, 1997 now abandoned, the entire content of which is hereby incorporated by reference in this application.

FIELD OF THE INVENTION

The subject invention relates to viruses that are able to replicate in and cause the death of neoplastic cells with a deficiency in the interferon (IFN)-mediated antiviral response. RNA and DNA viruses are useful in this regard. The invention also relates to the use of these viruses for the treatment of neoplastic diseases including cancer and large tumors.

BACKGROUND OF THE INVENTION

Neoplastic disease which includes cancer is one of the leading causes of death among human beings. There are over 1.3 million new cases of cancer diagnosed in the United States each year and 550,000 deaths. Detecting cancer early, before it has spread to secondary sites in the body, greatly increases a host's chances of survival. However, early detection of cancer is not always possible, and even when it is, treatments are unsatisfactory, especially in cases of highly malignant cancers. Cancer treatments, including chemotherapy and radiation, are much less effective in latter stages, especially when neoplastic growths are large and/or constitute a high tumor burden. (See Hillard Stanley, Cancer Treat. Reports, Vol. 61, No. 1, January/February 1977, p. 29-36, Tannock, Cancer Research, 42, 4921-4926, December 1982).

Tumor regression associated with exposure to various viruses has been reported. Most of the viruses described are pathogenic in humans, and include mumps and measles. The effect of other specific viruses on particular types of cancer cells has also been described. Smith et al, (1956) *Cancer*, 9, 1211 (effect of adenovirus on cervix carcinoma); Holzaepfel et al, (1957) *Cancer*, 10, 557 (effect of adenovirus on epithelial tumor); Taylor et al, (1970) *J. Natl. Cancer Inst.*, 44, 515 (effect of bovine enterovirus-1 on sarcoma-1); Shingu et al, (1991) *J. General Virology*, 72, 2031 (effect of bovine enterovirus MZ-468 on F-647a leukemia cells); Suskind et al, (1957) *PSEBM*, 94, 309 (effect of coxsackie B3 virus on HeLa tumor cells); Rukavishnikova et al, (1976) *Acta Virol.*, 20, 387 (effect of influenza A strain on ascites tumor).

The earliest references described partial tumor regression in patients treated with live attenuated viral vaccine with the aim to vaccinate them against smallpox or rabies. See DePace, N. G. (1912) *Ginecologia*, 9, 82-88; Salmon, P. & Baix (1922) *Compt. Rend. Soc. Biol.*, 86, 819-820. Partial regression of tumors and regression of leukemias have also been noted during naturally occurring measles infections. See Pasquinucci, G. (1971) *Lancet*, 1, 136; Gross, S. (1971) *Lancet*, 1, 397-398; Bluming, A. Z. and Ziegler, J. L. (1971) *Lancet*, 2, 105-106. In one study of 90 cancer patients intentionally infected with live mumps virus, partial tumor regression was noted in 79 cases. See Asada (1994) *Cancer*, 34, 1907-1928. While the side effects of these viruses were temporary, serious sequela of infection with these human pathogens is of major concern.

Viruses are categorized as follows [see Murphy A and Kingsbury D W, 1990, In: Virology, $2^{nd}$ Edition (Ed. Fields, B. N.), Raven Press, New York, pp 9-35]:

| Dividing Characteristics | Virus Family Names |
| --- | --- |
| RNA viruses | |
| ss RNA, positive-sense, nonsegmented, nonenveloped, | Picornaviridae, Caliciviridae |
| ssRNA, positive-sense, nonsegmented, enveloped, | Togaviridae, Flaviviridae, Coronaviridae |
| ssRNA, negative-sense, nonsegmented, enveloped, | Rhabodoviridae, Filoviridae, Paramyxoviridae |
| ssRNA, negative-sense, segmented, enveloped | Orthomyxoviridae |
| ssRNA, ambisense, segmented, enveloped | Bunyaviridae, Arenaviridae |
| dsRNA, positive-sense segmented, nonenveloped | Reoviridae, Birnaviridae |
| ssRNA, DNA step in replication, positive-sense, nonsegmented, enveloped | Retroviridae |
| DNA viruses | |
| ss/dsDNA, nonenveloped | Hepadnaviridae |
| ssDNA, nonenveloped | Parvoviridae |
| dsDNA, nonenveloped | Papovaviridae, Adenoviridae |
| dsDNA, enveloped | Herpesviridae, Poxviridae, Iridoviridae |

Included among the family Herpesviridae (or Herpesviruses), are the subfamilies Alphaherpesvirus (including Genus *Varicellavirus* and Genus *Simpexvirus*), Betaherpesvirus, and Gammaherpesvirus.

Newcastle disease virus ("NDV") is a member of the Paramyxoviridae (or Paramyxoviruses). The natural hosts for NDV are chickens and other birds. NDV typically binds to certain molecules on the surface of animal host cells, fuses with the cell surface, and injects its genetic material into the host. NDV is a cytocidal virus. Once inside the cell, the viral genes direct the host cell to make copies of the virus leading to death of the host cell, releasing the copies of NDV which infect other cells. Unlike some viruses, NDV is not known to cause any serious human disease. Unlike other kinds of viruses (e.g., HTLV-1, Hepatitis B), Paramyxoviruses are not known to be carcinogenic.

Temporary regression of tumors has been reported in a small number of patients exposed to NDV, See, Csatary, L. K. (1971) *Lancet*, 2, 825. Csatary noted the regression of a gastrointestinal cancer in a chicken farmer during an epidemic of Newcastle disease in his chickens. In a similar anecdotal report, Cassel, W. A. and Garrett, R. E. (1965) *Cancer*, 18, 863-868, noted regression of primary cervical cancer, which had spread to the lymph nodes, in a patient following injection of NDV into the cervical tumor. Since the mechanism of tumoricidal activity was thought to be immunologic, no work was carried out to address direct tumor cytotoxicity of the virus. Instead, efforts focused upon the immuno-modulating effects of NDV. See, for example, Murray, D. R., Cassel, W. A., Torbin, A H., Olkowski, Z. L., & Moore, M. E. (1977) *Cancer*, 40, 680; Cassel, W. A., Murray, D. R., & Phillips, H. S. (1983) *Cancer*, 52, 856; Bohle, W., Schlag, P J., Liebrich, W., Hohenberger, P., Manasterski, M., M^ller, P., and Schirrmacher, V. (1990) *Cancer*, 66, 1517-1523.

The selection of a specific virus for tumor regression was based on serendipity or trial and error in the above citations. Only recently, have rational, mechanism-based approaches for virus use in cancer treatment been developed using DNA viruses. Examples of this type of approach are found in the development of recombinant adenoviral vectors that replicate only in tumors of specific tissue origin (Rodriguez, R. et al, 1997 *Cancer Res.*, 57:2559-2563), or those that lack certain key regulatory proteins (Bischoff, J R, et al, 1996 *Science*, 274:373-376). Another recent approach has been the use of a replication-incompetent recombinant adenoviral vector to restore a critical protein function lost in some tumor cells (Zhang, W W, et al, 1994 *Cancer gene therapy* 1:5-13). Finally, herpes simplex virus has also been engineered to replicate preferentially in the rapidly dividing cells that characterize tumors (Mineta, T., et al, 1994 *Cancer Res.*, 54:3963-3966).

U.S. application Ser. No. 08/260,536, hereby incorporated by reference in its entirety, discloses the use of NDV or other Paramyxovirus in the treatment of cancer.

Viral IFN Transgene Expression

One common approach to the treatment of cancer with viral therapeutics has been the use of virus vectors for the delivery of certain genes to the tumor mass.

Recombinant adenovirus, adeno-associated virus, vaccinia virus and retroviruses have all been modified to express an interferon gene alone or in combination with other cytokine genes.

In Zhang et al. ((1996) *Proc. Natl. Acad. Sci., USA* 93:4513-4518), a recombinant adenovirus expressing a human interferon consensus (i.e., synthetic) gene was used to treat human breast cancer (and other) xenografts in nude mice. The authors concluded ". . . a combination of viral oncolysis with a virus of low pathogenicity, itself resistant to the effects of IFN and IFN gene therapy, might be a fruitful approach to the treatment of a variety of different tumors, in particular breast cancer." In contrast to subject invention which relates to interferon-sensitive viruses, Zhang et al. (1996) teach the use of an interferon-resistant adenovirus in the treatment of tumors.

In Zhang et al. ((1996) *Cancer Gene Ther.*, 3:31-38), adeno-associated virus (AAV) expressing consensus IFN was used to transduce human tumor cells in vitro followed by injection into nude mice. The transduced tumors either did not form tumors or grew slower than the non-transduced controls. Also, injection of one transduced human tumor cell into the tumor mass of another, non-transduced tumor resulted in a small decrease in size.

In Peplinski et al. ((1996) *Ann. Surg. Oncol.*, 3:15-23), IFN gamma (and other cytokines, expressed either alone, or in combination) were tested in a mouse breast cancer model. Mice were immunized with tumor cells virally modified with recombinant vaccinia virus. When re-challenged with tumor cells, the mice immunized with virally modified cells had statistical improvement in the disease-free survival time.

Gastl, et al. ((1992) *Cancer Res.*, 52:6229-6236), used IFN gamma-expressing retroviral vectors to transduce renal carcinoma cells in vitro. These cells were shown to produce higher amounts of a number of proteins important for the function of the immune system.

Restifo et al. ((1992) *J. Exp. Med.*, 175:1423-1431), used IFN gamma-expressing retroviral vector to transduce a murine sarcoma cell line allowing the tumor cell line to more efficiently present viral antigens to CD8+ T cells.

Howard, et al. ((1994) *Ann. NY Acad. Sci.*, 716:167-187), used IFN gamma-expressing retroviral vector to transduce murine and human melanoma tumor cells. These cells were observed to increase the expression of proteins important to immune function. These cells were also less tumorigenic in mice as compared to the non-transduced parent line, and resulted in activation of a tumor-specific CTL response in vivo.

Use of Therapeutic Doses of Interferon as an Adjuvant to Viral Cancer Therapy

Because of the known immune-enhancing properties of IFN, several studies have examined the use of IFN protein in combination with other viral cancer vaccine therapies.

In Kirchner et al. ((1995) *World J. Urol.*, 13:171-173), 208 patients were immunized with autologous, NDV-modified, and lethally irradiated renal-cell carcinoma tumor cells, and were co-treated with low dose IL-2 or IFN alpha. The authors stated that this treatment regime results in an improvement over the natural course in patients with locally-advanced renal-cell carcinoma. The dose was approximately $3.3 \times 10^3$ to $2.2 \times 10^5$ PFU/kg. This was a local therapy, as opposed to a systemic approach, with the goal of inducing an anti-tumor immune response.

Tanaka et al. ((1994) *J. Immunother. Emphasis Tumor Immunol.*, 16:283-293), co-administered IFN alpha with a recombinant vaccinia virus as a cancer vaccine therapy model in mice. This study showed a statistical improvement in survivability in mice receiving IFN as compared to those that did not. The authors attributed efficacy of IFN to the induction of CD8-positive T cells in those animals.

Arroyo et al. ((1990) *Cancer Immunol. Immunother.*, 31:305-311) used a mouse model of colon cancer to test the effect of IFN alpha and/or IL-2 co-therapy on the efficacy of a vaccinia virus colon oncolysate (VCO) cancer treatment. They found that the triple treatment of VCO+IL-2+IFN was most efficacious in this murine model. This approach relies on immunization as the mechanism of anti-tumor activity IFN was used in these studies to augment the ability of the cancer cells to be recognized by the immune system.

OBJECTS OF THE INVENTION

It is an object of the invention to provide viruses for the treatment of diseases including cancer.

It is a further object of the invention to provide viruses for the treatment of neoplastic diseases including cancer.

It is a further object of the invention to provide a means by which candidate viruses are selected and/or screened for use in the therapy of neoplastic diseases.

It is a further object of the invention to provide guidance in the genetic engineering of viruses in order to enhance their therapeutic utility in the treatment of neoplastic diseases.

It is a further object of this invention to provide a means with which to screen potential target cells for viral therapy with the goal of assessing the sensitivity of the candidate target cells to viral killing.

It is a still further object of this invention to provide guidance in the management of viral therapy.

It is an object of the invention to provide a method for treating large tumors.

It is a further object of the invention to provide purified virus and methods for obtaining same.

SUMMARY OF THE INVENTION

This invention relates to a method of infecting a neoplasm in a mammal with a virus comprising administering an interferon-sensitive, replication-competent clonal virus, selected from the group consisting of RNA viruses and the DNA virus families of Adenovirus, Parvovirus, Papovavirus, Iridovirus, and Herpesvirus, to the mammal.

This invention also relates to a method of infecting a neoplasm in a mammal with a virus comprising systemically administering an interferon-sensitive, replication-competent clonal virus to the mammal.

This invention also relates to a method of treating a neoplasm including cancer in a mammal comprising administering to the mammal a therapeutically effective amount of an interferon-sensitive, replication-competent, clonal virus selected from the group consisting of RNA viruses, and the DNA virus families of Adenovirus, Parvovirus, Papovavirus, Iridovirus, and Herpesvirus.

This invention also relates to a method of infecting a neoplasm in a mammal with a virus comprising administering an interferon-sensitive, replication-competent clonal vaccinia virus, having one or more mutations in one or more viral genes involved with blocking interferon's antiviral activity selected from the group of genes consisting of K3L, E3L and B18R, to the mammal.

The invention also relates to a method of treating a neoplasm including cancer in a mammal administering to the mammal a therapeutically effective amount of an interferon-sensitive, replication-competent vaccinia virus having one or more mutations in one or more viral genes involved with blocking interferon's antiviral activity selected from the group of genes consisting of K3L, E3L and B18R.

The invention also relates to a method of infecting a neoplasm at least 1 cm in size with a virus in a mammal comprising administering a clonal virus, selected from the group consisting of (1) RNA viruses; (2) Hepadenavirus; (3) Parvovirus; (4) Papovavirus; (5) Herpesvirus; (6) Poxvirus; and (7) Iridovirus, to the mammal.

The invention also relates to a method of treating a neoplasm in a mammal, comprising administering to the mammal a therapeutically effective amount of a clonal virus, selected from the group consisting of (1) RNA viruses; (2) Hepadenavirus; (3) Parvovirus; (4) Papovavirus; (5) Herpesvirus; (6) Poxvirus; and (7) Iridovirus, wherein the neoplasm is at least 1 centimeter in size.

The invention also relates to a method of treating a tumor in a mammal, comprising administering to the mammal a therapeutically effective amount of an RNA virus cytocidal to the tumor, wherein the mammal has a tumor burden comprising at least 1.5% of the total body weight The invention also relates to a method of screening tumor cells or tissue freshly removed from the patient to determine the sensitivity of the cells or tissue to killing by a virus comprising subjecting the cells or tissue to a differential cytotoxicity assay using an interferon-sensitive virus.

The invention also relates to a method for identifying a virus with antineoplastic activity in a mammal comprising a) using the test virus to infect i) cells deficient in IFN-mediated antiviral activity, and ii) cells competent in IFN-mediated antiviral activity, and b) determining whether the test virus kills the cells deficient in IFN-mediated antiviral activity preferentially to the cells competent in interferon-mediated antiviral activity.

The invention also relates to a method of making viruses for use in antineoplastic therapy comprising: a) modifying an existing virus by diminishing or ablating a viral mechanism for the inactivation of the antiviral effects of IFN, and optionally b) creating an attenuating mutation that results in lower virulence than said existing virus.

The invention also relates to a method of controlling viral replication in a mammal treated with a virus selected from the group consisting of RNA viruses, Adenoviruses, Poxviruses, Iridoviruses, Parvoviruses, Hepadnaviruses, Varicellaviruses, Betaherpesviruses, and Gammaherpesviruses comprising administering an antiviral compound.

This invention also relates to a method of treating or infecting a neoplasm in a mammal comprising subjecting a sample (e.g., serum, tumor cells, tumor tissue, tumor section) from the mammal to an immunoassay to detect the amount of virus receptor present to determine if the neoplasm will allow the virus to bind and cause cytolysis, and if the receptor is present, administering an interferon-sensitive, replication competent clonal virus, which binds the receptor, to the mammal.

The invention also relates to a method of infecting a neoplasm in a mammal with a virus comprising systemically administering a desensitizing dose of an interferon-sensitive, replication-competent clonal virus to the mammal.

The invention also relates to a method of infecting a neoplasm in a mammal with a virus comprising administering an interferon-sensitive, replication-competent clonal virus to the mammal over a course of at least 4 minutes.

This invention also relates to a method of infecting a neoplasm in a mammal with a virus comprising administering a replication-competent clonal virus selected from the group consisting of the Newcastle disease virus strain MK107, Newcastle disease virus strain NJ Roakin, Sindbis virus, and Vesicular stomatitis virus.

Included in the invention are:
i) a Paramyxovirus purified by ultracentrifugation without pelleting;
ii) a Paramyxovirus purified to a level of at least $2 \times 10^9$ PFU per mg of protein;
iii) a Paramyxovirus purified to a level of at least $1 \times 10^{10}$ PFU per mg of protein;
iv) a Paramyxovirus purified to a level of at least $6 \times 10^{10}$ PFU per mg of protein;
v) an RNA virus purified to a level of at least $2 \times 10^9$ PFU per mg of protein;
vi) an RNA virus purified to a level of at least $1 \times 10^{10}$ PFU per mg of protein;
vii) an RNA virus purified to a level of at least $6 \times 10^{10}$ PFU per mg of protein;
viii) a cytocidal DNA virus which is interferon-sensitive and purified to a level of at least $2 \times 10^9$ PFU/mg protein;
ix) a replication-competent vaccinia virus having a) one or more mutations in one or more of the K3L, E3L and B18R genes, and b) an attenuating mutation in one or more of the genes encoding thymidine kinase, ribonucleotide reductase, vaccinia growth factor, thymidylate kinase, DNA ligase, dUTPase;
x) a replication-competent vaccinia virus having one or more mutations in two or more genes selected from the group consisting of K3L, E3L, and B18R;
xi) a Herpesvirus having a modification in the expression of the (2'-5')A analog causing the Herpesvirus to have increased interferon sensitivity; and
xii) a Reovirus having an attenuating mutation at omega 3 causing said virus to become interferon-sensitive.

Also included in the invention are the following methods:
i) a method of purifying an RNA virus comprising the steps of a) generating a clonal virus; and b) purifying said clonal virus by ultracentrifugation without pelleting; or c) purifying said clonal virus by tangential flow filtration with or without subsequent gel permeation chromotagraphy, and
ii) a method of purifying a Paramyxovirus comprising purifying the virus by ultracentrifugation without pelleting, or by tangential flow filtration with or without subsequent gel permeation chromatagraphy.

The invention also relates to a method of treating a disease in a mammal, in which the diseased cells have defects in an interferon-mediated antiviral response, comprising administering to the mammal a therapeutically effective amount of an interferon-sensitive, replication-competent, clonal virus.

BRIEF DESCRIPTION OF THE DRAWINGS

FIG. 3A shows the effect of interferon on viral antigen expression in CCD922-sk cells, and FIG. 3B shows the effect of interferon on viral antigen expression in KB cells.

DETAILED DESCRIPTION OF THE INVENTION

Figure 1:
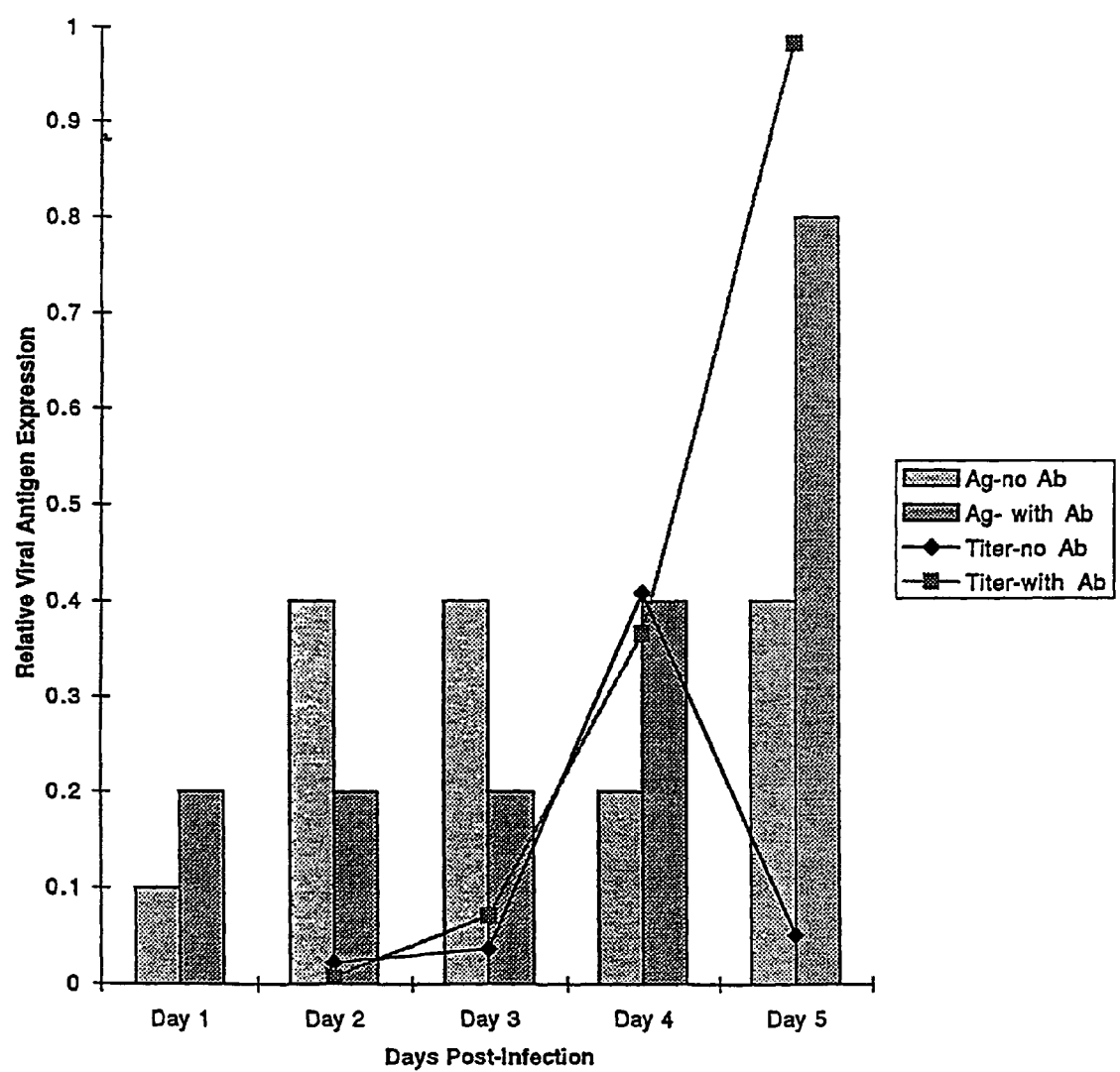
FIG. 1 shows the effect of anti-interferon-beta antibody on viral antigen expression and infectious titer in NHEK (normal human epithelial keratinocytes) cells.
Figure 2:
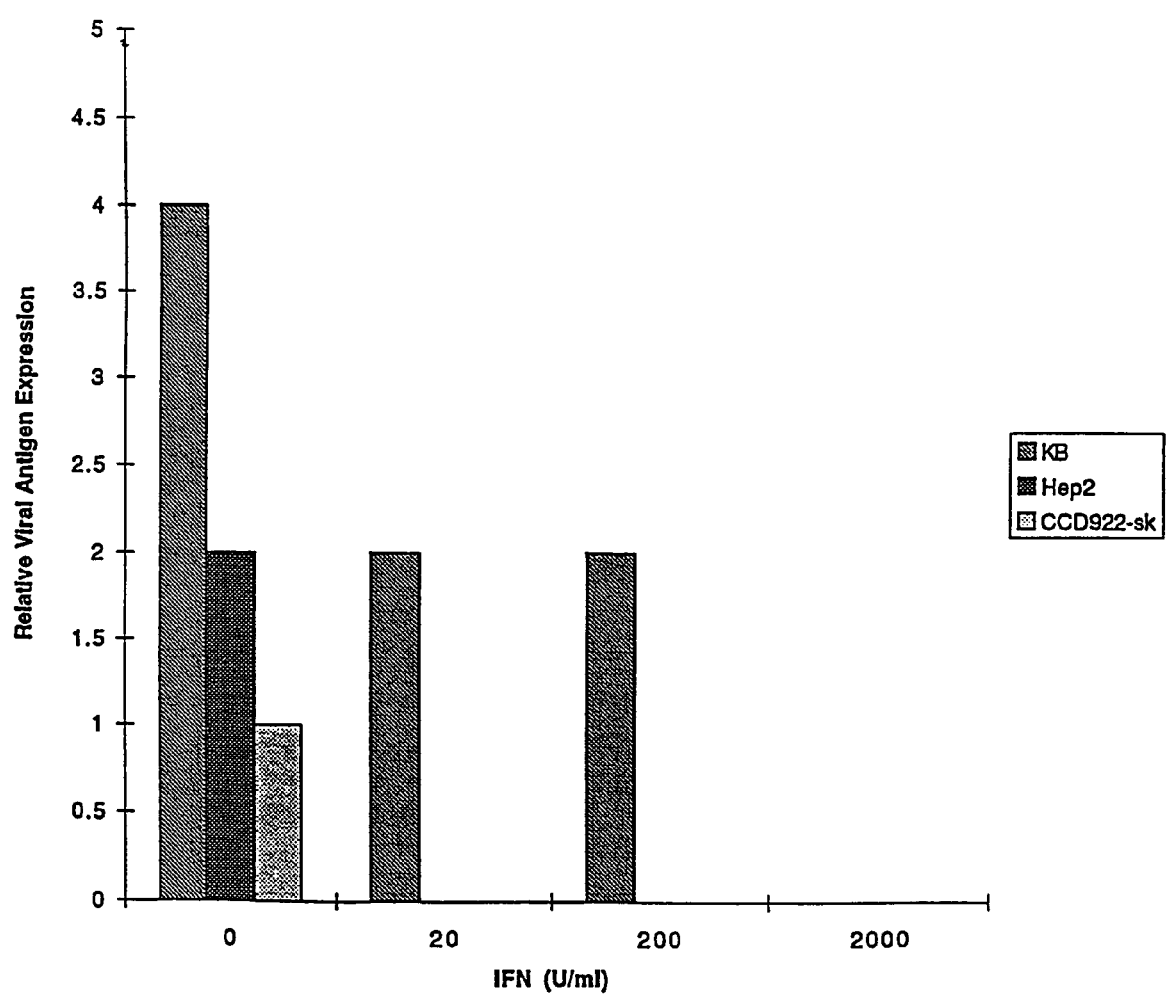
FIG. 2 shows the effect of interferon-beta on viral antigen expression in different cells (normal human skin fibroblasts CCD922-sk and two types of head and neck carcinoma cells (KB and Hep2 cells).
Figure 4:
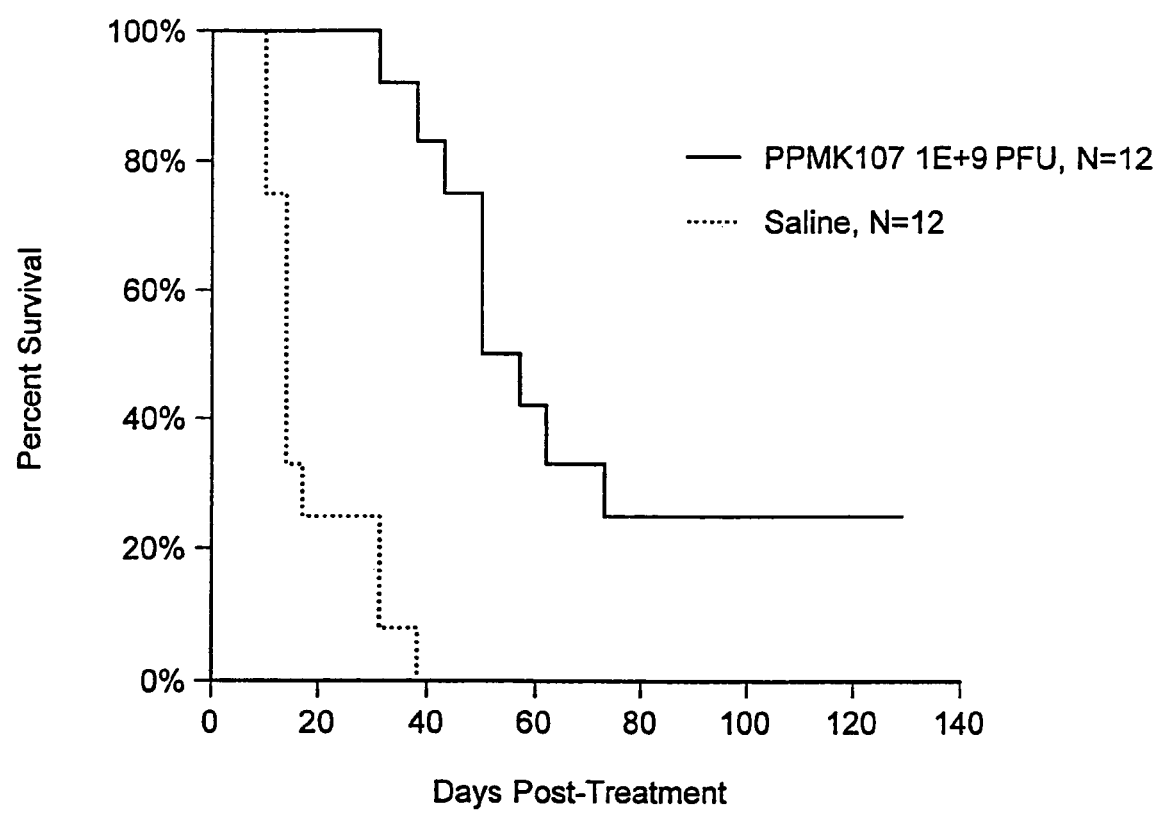
FIG. 4 shows the survival curves for athymic mice bearing human ES-2 ovarian carcinoma cells and treated with either saline or NDV strain PPMK107.
Figure 5:
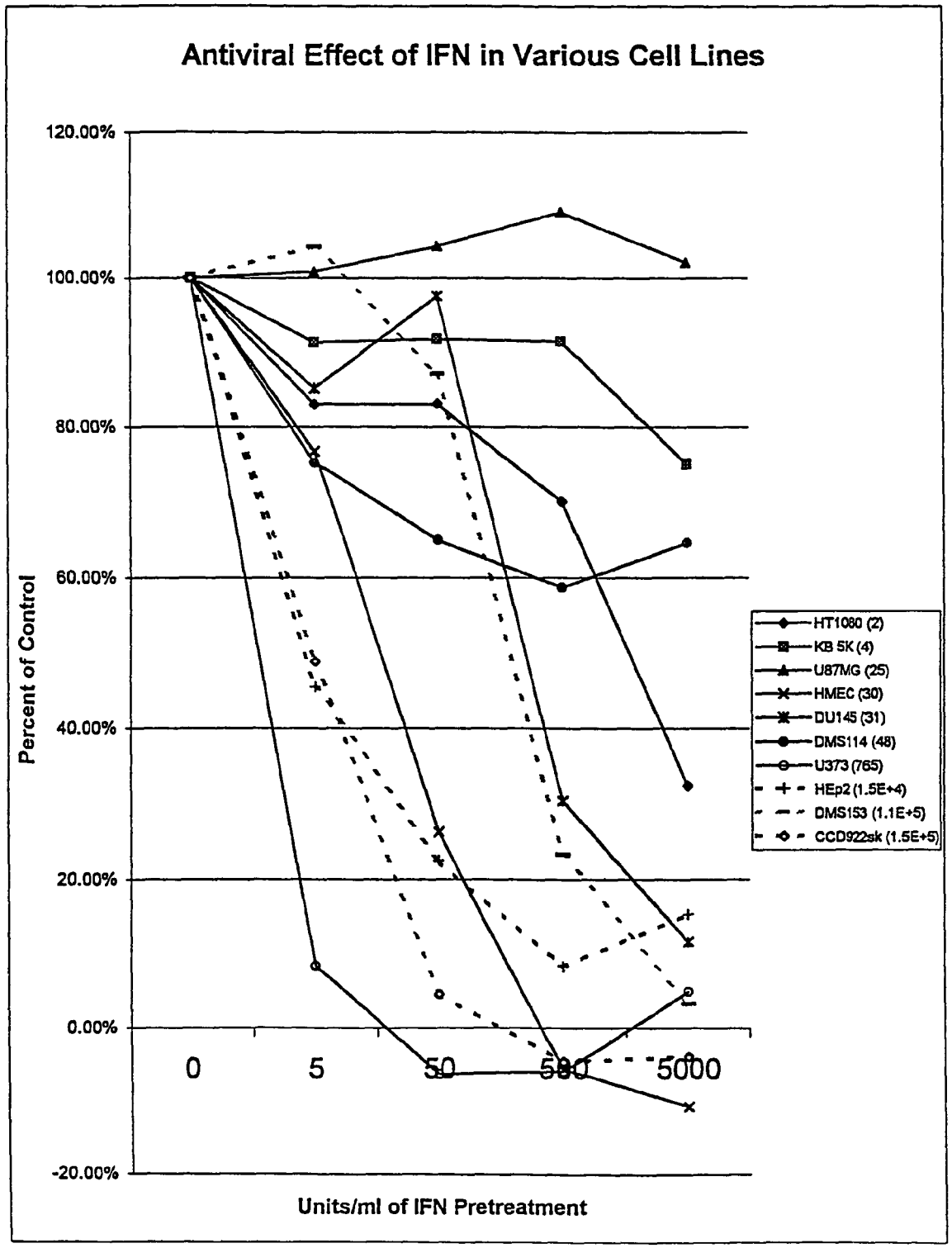
FIG. 5 shows the interferon responsiveness of a number of human tumor and normal cell lines.

The present invention relates to the discovery of a novel mechanism by which viral replication selectively kills neoplastic cells deficient in an interferon (IFN)-mediated anti-viral response. This invention also provides methods for selection, design, purification, and use of viruses for the treatment of neoplastic diseases including cancer and large tumors. The viruses of the invention selectively replicate in and kill neoplastic cells based on the selective deficiency in these cells of an IFN-mediated anti-viral response. Administration of the appropriate dosage of virus results in neoplastic cell death, whereas normal cells, which possess an intact IFN-mediated anti-viral response, limit the replication of the virus and are not killed.

Included in the subject of the invention is the use of paramyxoviruses such as NDV, and other viruses, for use in the treatment of diseases including neoplastic disease such as cancer. The invention also teaches screening and engineering of other viruses suitable for use as therapeutics of neoplastic diseases. Another embodiment of the invention involves a method of identifying tumor tissues that are candidates for viral therapy. Finally, the invention also describes the preparation of highly purified virus.

Rationale for the Use of Interferon-Sensitive Viruses Including NDV to Treat Neoplastic Disease NDV demonstrates selective killing of tumor cells.

Newcastle disease virus causes selective cytotoxic effects against many human tumor cells with markedly less effects on most normal human cells. In a differential cytotoxicity assay, human cancer cells derived from sarcomas, melanomas, breast carcinomas, ovarian carcinomas, bladder carcinomas, colon carcinoma, prostate carcinoma, small cell and non-small cell lung carcinomas, and glioblastomas were discovered o be approximately 3 to 4 orders of magnitude more sensitive to NDV than many normal human cells [renal epithelial cells, fibroblasts, keratinocytes, melanocytes, and endothelial cells (see Example 1)]. The differential cytotoxicity assay can also be applied to fresh isolates from the patient's cells or tumor tissue.

An in vitro assay is used to define the tumoricidal activity of NDV as described in Example 1. The assay measures the amount of virus required to kill 50% of the tested cell culture in a five day time period. Examples 2 and 3 show the results of in vivo experiments in which virus was administered to athymic mice bearing human tumor xenografts by either the intratumoral (Example 2) or intravenous (Example 3) route. These results demonstrate that NDV can cause regression of a variety of human tumor types in a standard animal model for the testing of potential chemotherapeutic agents.

Evidence that NDV is specifically replicating within the tumor was demonstrated by immunohistochemical staining for virus antigen (Example 2). Within 30 minutes of intratumoral virus injection, the tumor tissue was negative for viral antigen. However, by day 2 post treatment, intense immunostaining for viral antigen was seen within the tumor, indicating virus replication within the tumor. Importantly, virus replication was specific for the tumor tissue since the neighboring connective tissue and skin was negative for viral antigen.

Importantly, efficient replication of NDV is crucial for the ability of the virus to kill infected cells, as demonstrated in studies using UV-inactivated non-clonal virus (Lorence, R., et al, 1994 *J Natl Cancer Inst*, 86:1228-1233).

NDV can also cause regression of large tumors after intratumoral and intravenous administration (Examples 4 through 9). Intratumoral NDV treatment of large intradermal A375 human melanoma xenografts ($\geq$10 mm in maximal dimension; tumor volume of $\geq$300 mm$^3$) in athymic mice lead to high rates of tumor regression (Examples 4 through 8). Intravenous NDV treatment of large subcutaneous HT1080 human fibrosarcoma xenografts ($\geq$10 mm in maximal dimension) in athymic mice lead to complete or partial tumor regression in five out of six mice (Example 9).

The class I interferon family of cytokines are important negative modulators of viral infection.

The class I interferons consist of the IFNα, found primarily in cells of hematopoietic origin, and IFNβ found primarily in fibroblasts and epithelial cells. [Joklik W. K. 1990. Interferons. pp 383-410. *Virology*, second edition, edited by B. N. Fields, D. M. Knipe et al, Raven Press Ld., New York; and Sreevalsan, T. 1995. Biological Therapy with Interferon-α and β: Preclinical Studies. pp 347-364. *Biologic Therapy of Cancer*, second edition, edited by V. T. DeVita, Jr., S. Hellman, and S. A Rosenberg, J. B. Lippincott Company, Philadelphia.] Both types of IFN function through an apparently common mechanism of action that includes the degradation of double-stranded RNA intermediates of viral replication, and the inhibition of cellular translation through the activity of a protein kinase activated by double-stranded RNA (Joklik, W. K. 1990. Interferons. pp 383-410. *Virology*. Second Edition, edited by B. N. Fields, D. M. Knipe et al., Raven Press Ltd., New York; and references therein). Several viruses (influenza, EBV, SV40, adenovirus, vaccinia) have evolved mechanisms by which one or more pathways of the IFN system are inactivated, thus allowing the efficient replication of the virus (Katze, M. G. 1995. Trends in Microbiol. 3:75-78).

A wide variety of tumor cells are deficient in the ability to limit viral infection through an IFN-dependent mechanism.

Human cervical carcinoma cells (HeLa) were over three-hundred-fold less sensitive to the inhibition of vesicular stomatitis virus replication following pre-treatment with IFN than a non-transformed fibroblast control cell line (Maheshwari R. K., 1983. Biochem, Biophys. Res. Comm. 17:161-168). The subject inventors have discovered that infection of a co-culture of tumorigenic human head and neck carcinoma cells (KB) and normal human skin fibroblast cells (CCD922-sk) results in viral replication initially in both cell types, followed by a limiting of the infection in the normal cells versus continued replication and killing of the tumor cells (Example 10). Moreover, although IFN was being secreted by the normal cells into the culture medium, the tumor cells were unable to respond to the IFN at the concentrations being produced to establish an antiviral state. Further evidence for the role of IFN in the differential sensitivity of tumor cells versus normal cells to killing by NDV was obtained in two separate experiments in which normal fibroblast cells (CCD922-sk) or normal epithelial keratinocyte cells (NHEK) were shown to become more sensitive to infection with NDV in the presence of neutralizing antibody to IFN (Examples 11 and 12). Finally, parallel infection of normal fibroblasts (CCD922-sk) and human tumor cells (KB) in the presence of IFN revealed that the normal cells were at least 100-fold more sensitive to the antiviral effects of added IFN than were the tumor cells (Examples 13 and 14). Similar testing of variety tumor cell lines (total of 9) revealed a clear correlation in the relative sensitivity of a cell line to killing by NDV and an inability of the cell line to manifest an interferon-mediated antiviral response (Example 26).

Interferon and Cell Growth

There are several species of interferon (IFN) including natural and recombinant forms of $\alpha$-IFN, $\beta$-IFN, $\omega$-IFN, and $\gamma$-IFN as well as synthetic consensus forms (e.g., as described in Zhang et al. (1996) Cancer Gene Therapy, 3:31-38). In addition to the anti-viral activities that lead to its discovery, IFN is now known to play an important role in the normal regulation of cell growth and differentiation. IFN is viewed as a negative growth regulator and several key proteins involved in the function and regulation of IFN activity have been shown to act as tumor-suppresser proteins in normal cells (Tanaka et al, 1994 *Cell* 77:829-839). Moreover, several other proteins known to antagonize the anti-viral activity of IFN have been shown to have oncogenic potential when expressed inappropriately (see below, Barber, G N, 1994, *Proc. Natl. Acad. Sci. USA* 91:4278-4282). Cells derived from a number of human cancers have been shown to be deleted in the genes encoding IFN (James, C D, et al, 1991, *Cancer Res.,* 51:1684-1688), and partial or complete loss of IFN function has been observed in human cervical carcinoma (Petricoin, E, et al, 1994 *Mol. Cell. Bio.,* 14:1477-1486), chronic lymphocytic leukemia (Xu, B., et al, 1994, *Blood,* 84:1942-1949), and malignant melanoma cells, (Linge, C., et al, 1995, *Cancer Res.,* 55:4099-4104).

The IFN-inducible protein kinase (p68) has been shown to be an important regulator of cellular and viral protein synthesis. A correlation has emerged that links the expression or activity of the p68 kinase to the cellular state of differentiation. Thus, poorly differentiated cells, such as those occurring in many cancers, are deficient in p68 function (Haines, G. K., et al, 1993 *Virchows Arch B Cell Pathol.* 63:289-95). Cells that lack p68 activity are generally sensitive to viral mediated killing because the p68 kinase is an important effector of the IFN-inducible antiviral state. The antiviral activity of p68 can be antagonized through a direct interaction with a cellular protein identified as p58. When cloned and overexpressed in NIH3T3 cells, p58 causes the cells to exhibit a transformed phenotype and anchorage-independent growth (Barber G N et al., 1994 Proc Natl Acad Sci USA 91:4278-4282), and a number of human leukemia cell lines have been shown to overexpress the p58 protein (Korth M J, et al., 1996 Gene 170:181-188). Sensitivity to viral killing in undifferentiated cells can be reversed through the induction of a more differentiated phenotype (Kalvakolanu, D V R and Sen, G. C. 1993 *Proc Natl Acad Sci USA* 90:3167-3171).

Definitions

Cells competent in an interferon-mediated antiviral response. As used herein, the term "cells competent in an interferon-mediated antiviral response" are cells which respond to low levels (e.g., 10 units per ml) of exogenous interferon by significantly reducing (at least 10-fold, more advantageously at least 100-fold, more advantageously at least 1000-fold, and most advantageously at least 10,000-fold) the replication of an interferon-sensitive virus as compared to in the absence of interferon. The degree of virus replication is determined by measuring the amount of virus (e.g., infectious virus, viral antigen, viral nucleic acid). CCD922 normal fibroblasts are cells competent in an interferon-mediated antiviral response.

Cells deficient in an interferon-mediated antiviral response. As used herein, the term "cells deficient in an interferon-mediated antiviral response" are cells which fail to meet the criteria listed above for a cell competent in an interferon-mediated antiviral response, that is, they fail to respond to low levels (e.g., 10 units per ml) of exogenous interferon by significantly reducing the replication of an interferon-sensitive virus as compared to in the absence of interferon. KB oral carcinoma cells are cells deficient in an interferon-mediated antiviral response.

Clonal. Use of the term "clonal" virus is defined hereafter as virus derived from a single infectious virus particle and for which individual molecular clones have significant nucleic acid sequence homology. For example, the sequence homology is such that at least eight individual molecular clones from the population of virions have sequence homology greater than 95%, more advantageously greater than 97%, more advantageously greater than 99%, and most advantageously 100% over 300 contiguous nucleotides.

Cytocidal. As used herein, the term "cytocidal" virus refers to a virus that infects cells resulting in their death.

Desensitizing Dose. As used herein, the phrase, "desensitizing dose" refers to the amount of virus required to lessen the side effects of subsequent doses of the virus.

Differential Cytotoxicity Assay. As used herein, the phrase "differential cytotoxicity assay" for screening tumor cells or tissue using a virus refers to the (a) virus infection of the tumor cells and one or more control cells or tissue; (b) a determination of cell survivability or death for each sample (for example, by the use of a dye indicator of cell viability as in detailed in Example 1) after one or more days of infection; and (c) based on the results, an estimation of the sensitivity (for example, by IC50 determination as detailed in Example 1) of the sample to the virus compared to the control(s).

Infecting a Neoplasm. As used herein, the term "infecting a neoplasm" refers to the entry of viral nucleic acid into the neoplastic cells or tissues.

Interferon-sensitive. As used herein, the phrase "interferon-sensitive" virus (e.g., NDV) means a virus that replicates significantly less (at least 10-fold less, advantageously at least 100-fold less, more advantageously at least 1000-fold less, and most advantageously at least 10,000-fold less), in the presence of interferon compared to in the absence of interferon. This is determined by measuring the amount of virus (e.g., infectious virus, viral antigen, viral nucleic acid) obtained from cells competent in an interferon-mediated antiviral response in the presence or absence of low levels of exogenous interferon (e.g., 10 units per ml).

Neoplasm and Neoplastic Disease. As used herein, "neoplasm" means new growth of tissue, including tumors, benign growths (e.g., condylomas, papillomas) and malignant growths (e.g., cancer). As used herein, "neoplastic disease" refers to disease manifested by the presence of a neoplasm.

Replication Competent. As used herein, the term "replication-competent" virus refers to a virus that produces infectious progeny in neoplastic cells.

Substantially Free of Contaminating Egg Proteins. The term "substantially free of contaminating egg proteins" refers to a level of virus purity in which ovalbumin is not detectable in a Western blot as performed by one skilled in the art by (1) using $1.7 \times 10^9$ PFU of virus per well (3.3 cm in width) run on an SDS-PAGE (sodium dodecyl sulfate-polyacrylamide gel electrophoresis) gel (1 mm thick); (2) transfering the viral proteins from the gel to a nitrocellulose membrane; and (3) immunostaining for ovalbumin with the use of a rabbit anti-ovalbumin [Rabbit IgG fraction at a 1:200 dilution of a 4 mg/ml antibody concentration (from Cappel, Inc.) or equivalent polyclonal antibody].

Therapeutically effective amount. As used herein, the term "therapeutically effective amount" when referring to the treatment of neoplastic disease refers to a quantity of virus which produces the desired effect, e.g., cessation of neoplastic growth, tumor regression, improved clinical conditions, or increased survival.

Compounds of the Invention

A diverse group of viruses are used to selectively kill neoplastic cells. Natural or engineered viruses can function as an antineoplastic agent. These viruses i) infect neoplastic cells resulting in their death; ii) are replication-competent in the neoplastic cells; and iii) are limited in killing of normal cells by the antiviral effects of interferon.

In an advantageous embodiment of the invention, the viruses possessing the above three characteristics [(i) they infect neoplastic cells resulting in their death; (ii) they are replication-competent in the neoplastic cells; and (iii) they are limited in killing of normal cells by the antiviral effects of interferon] also induce interferon.

In another advantageous embodiment of the invention, the viruses possessing the above three characteristics also cause regression of human neoplasms; and/or are not neutralized in the target human population because of the presence of pre-existing immunity.

In another advantageous embodiment, the viruses possessing the above three characteristics are cytocidal to tumor cells.

A Paramyxovirus (as used herein "Paramyxovirus" refers to a member of the Paramyxoviridae) can be used according to the present invention to treat a neoplasm including a large tumor or a host having a high tumor burden. The Paramyxoviridae family comprises three genera: (1) paramyxoviruses; (2) measles-like viruses (morbilli viruses); and (3) respiratory syncytial viruses (pneuemoviruses). These viruses contain an RNA genome. Use of Paramyxoviridae viruses which are cytocidal, especially paramyxoviruses, e.g., Newcastle disease virus ("NDV") and other avian paramyxoviruses such as avian paramyxovirus type 2, is an advantageous method of practicing the invention. Attenuated strains of these viruses are especially useful for treatment of neoplasms in accordance with the present invention.

NDV is an especially advantageous virus according to the present invention. NDV is categorized into three distinct classes according to its effects on chickens and chicken embryos. "Low virulence" strains are referred to as lentogenic and take 90 to 150 hours to kill chicken embryos at the minimum lethal dose (MLD); "moderate virulence" strains are referred to as mesogenic and take 60 to 90 hours to kill chicken embryos at the MLD; "high virulence" strains are referred to as velogenic and take 40 to 60 hours to kill chicken embryos at the MLD. See, e.g., Hanson and Brandly, 1955 (Science, 122:156-157), and Dardiri et al., 1961 (Am. J. Vet. Res., 918-920). All three classes are useful, advantageously, mesogenic strains of NDV such as strain MK107, strain NJ Roakin, and strain Connecticut-70726. (see Examples 21-23). See, e.g., Schloer and Hanson, 1968 (J. Virol., 2:4047) for a listing of other mesogenic strains.

For certain purposes, it is desirable to obtain a clonal virus to ensure or increase the genetic homogeneity of a particular virus strain and to remove defective interfering particles. Removal of defective interfering particles by cloning allows for increased purity in the final product as assessed by the number of total virus particles per infectious particle (e.g., the number of particles per PFU).

Clonal virus can be produced according to any method available to the skilled worker. For example, plaque purification is routinely utilized to obtain clonal virus. See, e.g., Maassab et al., In: Plotkin and Mortimer, eds. *Vaccines. Philadelphia:* W.B. Saunders Co., 1994, pages 78-801. Triple plaque purification is especially desirable, where a plaque is selected at each round of purification having the desired characteristics, such as a preferred size, shape, appearance, or representative of the parental strain. Another means of generating clonal virus is by recombinant DNA techniques applicable by one skilled in the art. Another means of obtaining a clonal virus applies the technique of limiting dilution (e.g., by adding dilutions of the virus sample to give an average of one or less infectious virus particles per well containing a monolayer of a susceptible cell).

In an advantageous embodiment of the invention, purified virus is used to treat neoplastic diseases. An advantageous method for purification of egg derived viruses are as follows (virus is not pelleted at any step in these methods):

Purification Method A
  a) generating a clonal virus (e.g., plaque purification)
  b) inoculating eggs with the clonal virus
  c) incubating the eggs
  d) chilling the eggs
  e) harvesting the allantoic fluid from the eggs
  f) removing cell debris from the allantoic fluid
  h) ultracentrifugation of the allantoic fluid without pelleting (e.g., using a discontinous sucrose gradient)

In another embodiment of the invention, additional steps, added after the removal of the cell debris (from the allantoic fluid) and before ultracentrifugation, consist of:
  freezing then thawing the allantoic fluid
  removing contaminating material from the virus suspension (e.g., by means of centrifugation)

In another embodiment of the invention, ultracentrifugation is accomplished by means of a continuous flow ultracentrifuge.

One embodiment of the invention relates to a method of purifying a replication-competent RNA virus comprising the steps of:
  a) generating a clonal virus, and b) purifying said clonal virus by ultracentrifugation without pelleting.

Another embodiment of the invention involves a method of purifying a paramyxovirus (e.g., NDV) comprising purifying the virus by ultracentrifugation without pelleting. Optionally, the purifying step additionally comprises prior to the ultracentrifugation:
  a) plaque purifying to generate a clonal virus,
  b) inoculating eggs with the clonal virus,
  c) incubating the eggs,
  d) chilling the eggs, e) harvesting allantoic fluid from the eggs and,
f) removing cell debris from the allantoic fluid.

Another embodiment of the invention involves a method of purifying a replication-competent clonal virus from eggs or cell culture comprising the step of ultracentrifugation without a step in which the virus is pelleted.

Another embodiment of the invention involves a method of the purifying a paramyxovirus (e.g., NDV) comprising purifying the virus by sequential tangential flow filtration (TFF). Optionally, the virus can be additionally purified by gel permeation chromatography, where each of these steps occurs in the presence of a stabilizing buffer (Example 15):
a) plaque purifying to generate a clonal virus,
b) inoculating eggs with the clonal virus,
c) incubating the eggs,
d) chilling the eggs,
e) harvesting allantoic fluid from the eggs and dilution of allantoic fluid with buffer,
f) removing cell debris from the allantoic fluid by TFF,
g) purification of the virus by TFF, and
h) purification of the virus by gel permeation chromatography.

Optionally, the virus obtained from the gel permeation step can be concentrated using TFF.

Another embodiment of the invention involves a method of purifying a replication-competent clonal virus from eggs or cell culture comprising the step purifying the virus by sequential tangential flow filtration (TFF), optionally followed by gel permeation chromatography, optionally followed by TFF to concentrate the virus.

Clonal Virus
Use of these methods permits purification of a clonal virus [including Paramyxovirus (e.g., NDV)] to at least $2\times10^9$ PFU/mg protein, advantageously to at least $3\times10^9$ PFU/mg protein, more advantageously to at least $5\times10^9$ PFU/mg protein, more advantageously to at least $1.0\times10^{10}$ PFU/mg protein, more advantageously to at least $2.0\times10^{10}$ PFU/mg protein, more advantageously to at least $3\times10^{10}$ PFU/mg protein, more advantageously to at least $4\times10^{10}$ PFU/mg protein, more advantageously to at least $5\times10^{10}$ PFU/mg protein, and most advantageously at least $6\times10^{10}$ PFU/mg.

Use of these methods permits purification of a clonal virus [including Paramyxovirus (e.g., NDV)] to level in which the number of virus particles per PFU is less than 10, more advantageously less than 5, more advantageously less than 3, more advantageously less than 2, and most advantageously less than 1.2. (Lower numbers of virus particles per PFU indicate a higher degree of purity.)

RNA Viruses
In another embodiment, these methods permit purification (to the levels cited above for clonal viruses) of an RNA virus [including (a) a cytocidal RNA virus; (b) a single-stranded RNA non-segmented, nonenveloped virus; (c) a single-stranded RNA segmented, enveloped virus; (d) a double-stranded RNA segmented, nonenveloped virus; (e) and a single-stranded RNA non-segmented, enveloped virus (e.g., Paramyxovirus (e.g., NDV) and e.g., Retroviruses].

DNA Viruses
In another embodiment, these methods permit purification (to the levels cited above for clonal viruses) of an interferon-sensitive cytocidal virus selected from the group consisting of (a) enveloped, double-stranded DNA viruses (including poxviruses); (b) nonenveloped, single-stranded DNA viruses; and (c) nonenveloped, double-stranded DNA viruses.

Egg Derived Viruses
In another embodiment, these methods permit purification of egg derived viruses to a level substantially free of contaminating egg proteins. It is preferred to limit the amount of egg proteins in virus preparations for human therapeutic use since major egg proteins like ovalbumin are allergens.

Viruses useful in the treatment of neoplastic diseases including cancer are shown in Table 1. These viruses are optionally screened for naturally occurring variations (certain strains or isolates) that result in altered IFN production relative to the parental strain.

In another embodiment of this invention, candidate viruses, whether naturally occurring or engineered, are tested for the ability to provide therapeutic utility in the treatment of neoplasms. In one embodiment, the amount of candidate virus required to kill 50% of cells deficient in an interferon-mediated antiviral response, e.g., KB head and neck carcinoma cells, is compared to the amount of virus required to kill 50% of a similar number of cells competent in an interferon-mediated antiviral response, for example normal skin fibroblasts. The amount of killing is quantified by any number of means including trypan blue exclusion or MTT assay (see Example 1). A significant reduction (e.g., at least 5-fold) in the amount of virus required to kill cells deficient in an interferon-mediated antiviral response relative to the amount needed to kill cells competent in an interferon-mediated antiviral response indicates that the virus

TABLE 1

Naturally Occurring Viruses for Use in Cancer Therapy

| Virus Class | Virus Family | Virus Example |
|---|---|---|
| RNA, negative stranded | Paramyxoviridae | Newcastle Disease Virus<br>Avian Paramyxovirus Type 2<br>Mumps<br>Human Parainfluenza |
|  | Rhabdoviridae | Vesicular Stomatitis Virus |
| RNA, positive stranded | Togaviridae | Sindbis Virus |
|  | Flaviviridae | Yellow Fever Virus (attenuated) |
|  | Picornaviridae | Rhinovirus<br>Bovine Enterovirus<br>Echovirus |
|  | Coronaviridae | Avian Infectious Bronchitis Virus<br>Human Coronaviruses | being tested exhibits activity required for therapeutic utility in the treatment of neoplasms. Other NDV viruses and Sindbis virus are such natural occurring viruses that display tumor-selective killing (see Examples 21-23, and 25).

An understanding of the factors involved in the establishment of an antiviral state allows for the creation of a screening assay for tumors that are likely to respond to viral therapy. In principle, patient derived tumor tissue obtained from biopsy is screened for the expression of p68 kinase, p58, or other factors involved in the regulation of an antiviral state or cellular differentiation. Other factors include, but are not limited to, interferon response factor-1 (IRF-1), interferon stimulatory gene factor-3 (ISGF-3), c-Myc, c-Myb, and IFN receptors. In the case of c-Myc, c-Myb or p58, high level expression indicates that the tumor tissue or cells are treatment candidates for virus therapy. In the case of p68, IRF-1, ISGF-3, and IFN receptors, low level expression indicates that the tumor tissue or cells are treatment candidates for virus therapy.

In another embodiment of this invention, primary tumor tissue or cells obtained from patient biopsies are expanded in culture and tested for sensitivity to killing by a suitable viral therapy. In one embodiment, the amount of virus required to kill 50% of the tumor tissue culture is compared to the amount required to kill 50% of a culture of normal cells as described above for the screening of candidate viruses. An increase of ten-fold or greater in the sensitivity of the tumor cells relative to normal cells to killing by the viral agent indicates that the tumor cells are specifically sensitive to the cytocidal effects of the viral treatment. In a further embodiment of the invention, the ability of the targeted tumor cells to respond to endogenously or exogenously supplied IFN is determined by conducting the above screen in the presence of IFN (alpha or beta form, using e.g., 10 units per ml, see Example 27).

An understanding of the cellular receptors required for virus attachment or entry allows additional screening for tumors that have high receptor expression and hence enhanced sensitivity to the interferon-sensitive virus. This is an additional level screening for patients that are likely to respond to virus therapy. Advantageously for therapy with an interferon-sensitive virus, the patient's tumor is both resistant to interferon and has high expression of the cellular receptor for the virus. In principle, patient derived serum, tumor cells, tissues, or tissue sections are screened by immunoassay or immunostain for the amount of virus receptor present in the serum or on the tumor cells or tumor tissue. For example, Sindbis virus utilizes the high affinity laminin receptor to infect mammalian cells (Wang et al., 1992, J Virol., 66, 4992-5001). This same receptor is known to be expressed in higher amounts in many diverse types of metastatic cancer. The PANC-1 renal cancer cell line, and the colon adenocarcinoma cell line SW620 are known to express a high level of high affinity laminin receptor mRNA (Campo et al, 1992, Am J Pathol 141:107301983; Yow et al., (1988) Proc. Natl Acad Sci, 85, 6394-6398) and are highly sensitive to Sindbis virus (Example 25). In contrast, the rectum adenocarcinoma cell line SW1423 is known to express very low levels of high affinity lamin receptor mRNA (Yow et al., (1988) Proc. Natl Acad Sci, 85, 6394-6398), and is more than 4 orders of magnitude more resistant to killing by PPSINDBIS-Ar339 than SW620 cells.

Existing strains of NDV, or other viruses including RNA and DNA viruses, are screened or engineered for altered IFN responses (e.g., advantageously increased IFN responses) in normal cells. In addition to the ability to elicit a strong IFN response, other viral characteristics are screened for or engineered into the virus. Viruses with altered receptor specificity (e.g., Sindbis virus PPSINDBIS-Ar339, see Example 25), or low neurovirulence are included in the subject invention (e.g., NDV virus PPNJROAKIN, see Example 24). Advantageously, viruses of the invention have the capacity to spread through direct cell to cell contact.

The invention described herein includes a broad group of viruses (see Table 1) that are useful for treatment of neoplasms in a manner analogous to the indication for NDV. In addition, viruses that naturally would not be candidates for use, due to the presence of a mechanism(s) to inactivate the IFN response in normal cells, are optionally engineered to circumvent the above restrictions. If left unmodified, viruses with mechanisms to inactivate the interferon response would be more toxic to normal cells than viruses with such mechanism removed. The subject invention provides (1) the development of a vector that can be easily manipulated; and (2) the creation of a set of therapeutic viruses. Manipulations include the addition of an IFN gene to permit the viral expression of a transgene expressing IFN, or other activators of the IFN response pathway. Additional permutations include the engineered expression of pro-drug activating enzymes such as the Herpesvirus thymidine kinase or cytosine deaminase (Blaese R M et al., 1994. Eur. J. Cancer 30A: 1190-1193) and the expression of suitable marker antigen to allow targeting of tumor cells by the immune system. An additional permutation include the engineered expression of receptor ligands to target cells with those receptors [e.g., expression of receptors to other viruses to target cells infected with those viruses (see Mebastsion et al., 1997, Cell 90:841-847; and Schnell M J et al., 1997, Cell 90:849-857].

Several Newcastle Disease virus strains demonstrate selective killing of tumor cells. In a differential cytotoxicity assay using a second strain of mesogenic Newcastle Disease virus, tumor cells were found to be 3 orders of magnitude more sensitive than normal cells to killing by the virus (Example 21). Additionally, when a third mesogenic Newcastle Disease virus strain was used in a differential cytotoxicity assay, tumor cells were found to be 80 to 5000-fold more sensitive than normal cells to killing by the virus (Example 22). Both of these mesogenic Newcastle Disease virus strains also caused tumor growth regression following intratumoral administration to athymic mice bearing human tumor xenografts (Example 23).

In separate experiments, the safety of three distinct Newcastle Disease virus strains were studied following intracerebral inoculation in athymic and immune-competent mice. The results of this study showed that all three virus strains were well tolerated in mice with an intact immune system. Intracerebral inoculation into the brains of athymic mice revealed that one of the viruses was tolerated significantly better than the other two (Example 24). These results demonstrate that within a single virus family important differences in viral properties can occur and be can be exploited therapeutically for greater efficacy or increased safety.

Another means by which increased efficacy and lower toxicity following treatment with oncolytic viruses can be achieved is through the use of interferon-sensitive viruses that require specific cell surface receptors that are preferentially expressed on tumor cells. Sindbis virus provides an example of this type of restriction. Sindbis virus infects mammalian cells using the high affinity laminin receptor (Wang et al., (1992) J. Virol. 66, 4992-5001). When normal and tumor cells were infected with Sindbis virus in a differential cytotoxicity assay, cells which both were tumorigenic and expressed the high affinity laminin receptor were found to be more sensitive to killing by this virus than other cells (Example 25). Normal keratinocytes express the high affinity laminin receptor (Hand et al., (1985) Cancer Res., 45, 2713-2719), but were resistant to killing by Sindbis in this assay.

Vesicular Stomatitis Virus (VSV) provides evidence of tumor-selective killing of by oncolytic viruses, i.e., an inherent deficiency in interferon responsiveness in tumor cells renders these cells sensitive to killing by interferon-sensitive replication-competent virsus. When VSV was used to infect non-tumorigenic human WISH cells and tumorigenic HT1080 or KB cells in the presence of exogenous interferon.

Below is a list of viruses that when modified to remove naturally-occurring anti-interferon activities, are useful for viral cancer therapy (see Table 2). Modified viruses (advantageously, but not necessarily, attenuated in addition to the anti-interferon modification, see Table 3) that have had endogenous anti-interferon activities destroyed or reduced, are useful for cancer therapy. This list includes, but is not be limited to, the viruses described below. Because of the similarity between viruses of a common class, the identified mechanisms for each of the specific viruses listed below, are also present in other members of that class of virus as identical or functionally analogous mechanisms. The broader group of viruses is added in parenthesis. Viruses, such as those below, that have a functional loss of anti-interferon activity, through any means, including natural occurring mutations, as well as engineered deletions or point mutations, are useful in the methods of the subject invention.

Viruses that exercise more than one mechanism are optionally modified to contain mutations in one, some, or all of the activities. Mutations for some of the described activities are available in the general scientific community.

Isolates of naturally occurring or engineered virus that are slower growing, compared to the growth rate of wild-type virus, are particularly advantageous because a slower virus growth rate will allow a cell or population of cells competent in an interferon response to establish an efficient antiviral state before viral replication can kill the cell or cell population.

The disabling of viral anti-interferon activities as a specific alteration of viral character that results in the augmentation of the interferon response in an infected cell, but still allows viral replication in neoplastic cells is included in the subject invention.

Table 2 shows existing viruses engineered to remove anti-interferon activity.

Table 3 lists viruses engineered to be attenuated in virulence.

which are smaller in size. In a more advantageous aspect of the invention, tumors greater than 1 cm. are treated, e.g., tumors which are 2 cm or greater, from about 2 cm to about 5 cm, and greater than 5 cm.

The present invention can also be employed to treat hosts having a high tumor burden. As used herein, the phrase "tumor burden" refers to the total amount of tumor within the body expressed as a percentage as body weight. Viral therapy of hosts having a tumor burden, e.g., from about 1% to about 2% of total body weight is surprisingly effective, e.g., producing tumor regression and a reduction in the overall tumor load. This is especially unexpected since a tumor burden of approximately 2% of the total body weight (e.g., a 1 kg tumor in a 60 kg human) is approximately the maximum cancer mass compatible with life. See, e.g., Cotran et al., In *Robbins Pathological Basis of Diseases,* 4th Edition, W B Saunders, 1989, page 252. In the Examples, volumes up to 397 $mm^3$ for a melanoma cancer (e.g., A375) in a mouse host showed complete regression in response to treatment with a Newcastle disease virus (e.g., a triple-plaque purified virus). Assuming that for tissue 1000 $mm^3$ equals 1 gram, a tumor having a volume of 397 $mm^3$ comprises approximately 2% of the total body weight for a 20 gram mouse.

TABLE 2

Extant Viruses Engineered to Remove Anti-IFN Activity

| Virus Class | Virus Family | Virus | Anti-IFN Activity | Reference |
|---|---|---|---|---|
| RNA | Reoviridae | reovirus | σ3 | Imani F and Jacobs B (1988) Proc Natl Acad Sci USA 85: 7887-7891. |
| DNA | Poxviridae | Vaccinia | K3L | Beattie E et al. (1991) Virology 183: 419 |
| | | | E3L | Beattie E et al. (1996) Virus Genes 12: 89-94. |
| | | | B18R | Symons JA et al. (1995) Cell 81: 551-560. |
| | Adenoviridae | various subtypes | $VA_1$ transcripts | Mathews MB and Shenk T (1991) J Virol 64: 5657-5662. |
| | Alphaherpesvirinae | HSV-1 | gamma 34.5 gene product | Chou J et al (1996) Proc Natl Acad Sci USA 92: 10516-10520. |

TABLE 3

Known Attenuating Mutations In Selected Viruses

| Virus Class | Virus Family | Virus | Attenuation | Reference |
|---|---|---|---|---|
| RNA | Reoviridae | reovirus | σ1 | Spriggs DR and Fields BN (1982) Nature 297: 68-70. |
| | | rotavirus | bovine strains (WC3) | Clark HF (1988) J Infect Dis 158: 570-587. |
| DNA | Poxviridae | Vaccinia | vaccinia growth factor | Buller RML et al (1988) Virology 164: 182. |
| | | | thymidine kinase | Buller RML et al (1985) Nature 317: 813-815. |
| | | | thymidylate kinase | Hughes SJ et al (1991) J Biol Chem 266: 20103-20109 |
| | | | DNA ligase | Kerr SM et al (1991) EMBO J 10: 4343-4350. |
| | | | ribonucleotide reductase | Child SJ et al (1990) Virology 174: 625-629. |
| | | | dUTPase | Perkus ME et al (1991) Virology 180: 406-410. |
| | Adenoviridae | various subtypes | Ad-4, Ad-7, Ad-21 | Takafugi ET et al (1979) J Infect Dis 140: 48-53. |
| | Alphaherpesvirinae | HSV-1 | thymidine kinase | Field HJ and Wildy P (1978) J Hyg 81: 267-277. |
| | | | ribonucleotide reductase | Goldstein DJ and Weller sk (1988) Virology 166: 41-51. |
| | | | gamma 34.5 gene product | Chou J et al (1995) Proc Natl Acad Sci USA 92: 10516-10520. |
| | | | b'a'c' inverted repeats | Meignier B et al (1988) J Infect Dis 162: 313-322. |

Treatment of Neoplasms

The present invention relates to viral therapy of neoplasms, especially in animals having cancer. In an advantageous embodiment, the invention relates to the treatment of tumors which are 1 centimeter (cm) or more in size as measured in the greatest dimension. As used herein, "a 1 cm tumor" indicates that at least one dimension of the tumor is 1 cm in length. Such tumors are more sensitive than expected to viral therapy, often at least as sensitive to virus, if not more sensitive, than tumors As shown in Examples 4 to 9 below, tumor regression was achieved with tumors at least 1 cm in size, while untreated, control animals began dying from tumor burden within several weeks. Thus, such diseased animals were successfully treated despite being within two weeks of death. Thus, in accordance with the present invention, an animal which is near terminal from its tumor burden can be treated effectively with viral therapy. Consequently, the present invention can be used to treat patients who have not responded to conventional therapy, e.g., chemotherapy such as methotrexate, 5-fluorouracil, and radiation therapy.

The efficacy of NDV for the treatment of cancer following administration through the intraperitoneal route has also been examined. Using an ascites prevention model of ovarian cancer, intraperitoneal injection of NDV in mice harboring ES-2 human ovarian tumors resulted in increased survival compared to mice treated with saline (Example 16). When ES-2 cells were used in an ovarian cancer tumor model with treatment initiated once ascites formed, ascites fluid production was markedly decreased in virus-treated animals compared to saline controls (Example 17).

In another embodiment of the invention, the administration of virus results in 1) the relief of tumor related symptoms, such as but not limited to deceased rate of ascites fluid production, relief of pain, and relief of obstructive disease, and 2) the prolongation of life.

Twenty-three patients have received the plaque purified NDV isolate by the intravenous route (Example 20). Treatment responses include the regression of a palpable tumor, the stabilization of disease in 47% of patients and a reduction in pain medication.

Administration and Formulation

In one embodiment of the invention, tumor cells or tissue are screened in vitro to determine those patients with tumors sensitive to the virus. Tumor cells removed from the patient (by methods such as fine needle aspiration for solid tumors or by paracentesis for ovarian ascites tumors) are grown in vitro and incubated with virus. In this embodiment of the invention, patients are selected for therapy if the virus has a high activity against their tumor cells.

In an advantageous embodiment of the invention, the amount of virus administered results in regression of the tumor or tumors. As used herein, the term "regression" means that the tumor shrinks, e.g., in size, mass, or volume. Shrinkage in tumor size is demonstrated by various methods, including physical examination, chest film or other x-ray, sonography, CT scan, MRI, or a radionucleotide scanning procedure.

Various types of neoplasms including cancers are treatable in accordance with the invention. The viruses of the present invention are useful to treat a variety of cancers, including but not limited to lung carcinoma, breast carcinoma, prostate carcinoma, colon adenocarcinoma, cervical carcinoma, endometrial carcinoma, ovarian carcinoma, bladder carcinoma, Wilm's tumor, fibrosarcoma, osteosarcoma, melanoma, synovial sarcoma, neuroblastoma, lymphoma, leukemia, brain cancer including glioblastoma, neuroendocrine carcinoma, renal carcinoma, head and neck carcinoma, stomach carcinoma, esophageal carcinoma, vulvular carcinoma, sarcoma, skin cancer, thyroid pancreatic cancer, and mesothelioma. The viruses of the present invention are also useful to treat a variety of benign tumors, including but not limited to condylomas, papillomas, meningiomas, and adenomas.

A therapeutically effective amount of virus is administered to a host having a neoplasm. It is understood by those skilled in the art that the dose of virus administered will vary depending on the virus selected, type of neoplasm, the extent of neoplastic cell growth or metastasis, the biological site or body compartment of the neoplasm(s), the strain of virus, the route of administration, the schedule of administration, the mode of administration, and the identity of any other drugs or treatment being administered to the mammal, such as radiation, chemotherapy, or surgical treatment. These parameters are defined through maximum tolerated dose determination in animal models and scaling to human dosage as a function of relative body surface area or body mass. It is also understood that under certain circumstances, more than one dose of the virus is given. The optimal interval between such multiple doses of the virus can be determined empirically and is within the skill of the art. NDV is generally administered from about $3 \times 10^6$ to about $5 \times 10^{12}$ PFU of virus. For local administration (e.g., directly into a tumor), total amounts of from about $3 \times 10^6$ to about $5 \times 10^{10}$ PFU of virus are typically used. For systemic administration, amounts of from about $1 \times 10^8$ to about $4 \times 10^{11}$ PFU of virus per square meter of body surface area are used. For intravenous administration, dosing schedules of once per week, two times per week and three times per week are used. A virus in accordance with the present invention, optionally with a chemotherapeutic agent, can be administered by various routes, e.g., enteral, parenteral, oral, nasal, rectal, intrathecal, intervenous (e.g., using a catheter), subcutaneous, intratumor (e.g., directly into its tissue or into vessels which perfuse it), peritumoral, local, sublingual, buccal, topical, intramuscular, by inhalation, percutaneous, vaginal, intra-arterial, intra-cranial, intradermal, epidural, systemically, topical, intraperitoneal, intrapleural, etc. For lung tumors, a bronchial route (e.g., bronchial administration) can be used. Endoscopic injections of gastrointestinal tumors, as well as suppository treatments of rectal tumors are also used where appropriate.

Murine toxicity studies with NDV have indicated that the acute toxicity following intravenous virus administration is likely to be caused by cytokine mediated reactions. Cytokine responses to repeated stimuli are known to be desensitized, or down-regulated, following the initial induction event (Takahashi et al., (1991) Cancer Res. 51, 2366-2372). Mice intravenously injected with a desensitizing dose of virus were able to tolerate approximately 10-fold more virus on a second dose than mice receiving vehicle alone for the first injection (Example 18).

The rate of virus administration by the intravenous route can significantly affect toxicity. Two groups of athymic mice were intravenously treated with identical doses of NDV which was administered either slowly (0.2 ml over 4 minutes) or rapidly (0.2 ml over 30 seconds). Comparison of the maximal weight lose in each group revealed 50% less weight loss in the group receiving slow injection versus a rapid injection (Example 19).

In one cohort of a clinical trial, patients received three injections of the plaque purified NDV isolate over the course of one week (Example 20). Under these conditions, a desensitizing effect of the initial dose lessened the toxicity associated with the second and third doses. These data parallel those obtained with the animal studies shown in Example 18. One concern related to the use of oncolytic viruses in the treatment of cancer is the potential inhibitory effect the humoral immune response can exert on the therapy. In the clinical study, patients displaying stable disease after 1 month are eligible for a second course of treatment which then is administered in the presence of neutralizing antibodies to NDV. Nevertheless, infectious virus could be found in patient urine seven days after dosing for the second course, providing evidence that administration of high doses of virus can overcome the effect of neutralizing antibodies and establish an infection within the patient.

In an advantageous embodiment of the invention, a desensitizing dose is given before higher subsequent doses. For desensitization, virus doses of $1 \times 10^8$ to $2.4 \times 10^{10}$ PFU/m$^2$ are used. After desensitization, additional virus doses of $3 \times 10^8$ to $4 \times 10^{12}$ PFU/m$^2$ are used. The time frame between doses, including the time frame between desensitizing dose and the next dose, is 1 to 14 days, advantageously 1 to 7 days. The desensitizing dose can be administered by various routes, e.g., intravenous, enteral, parenteral, oral, nasal, rectal, intrathecal, intervenous, subcutaneous, intratumor, peritumoral, local, sublingual, buccal, topical, intramuscular, by inhalation, percutaenous, vaginal, intra-arterial, intracranial, intradermal, epidural, sytemically, topical, intraperitoneal, intrapleural, endoscopic, intrabronchial, etc. The subsequent doses can be administered by the same route as the desensitizing dose or by another route, e.g., intravenous, enteral, parenteral, oral, nasal, rectal, intrathecal, intervenous, subcutaneous, intratumor, peritumoral, local, sublingual, buccal, topical, intramuscular, by inhalation, percutaenous, vaginal, intra-arterial, intracranial, intradermal, epidural, sytemically, topical, intraperitoneal, intrapleural, endoscopic, intrabronchial, etc.

Optionally, more than one route of administration can be used in either a sequential or concurrent mode. Routes for either concurrent or sequential administration include but are not limited to intravenous, enteral, parenteral, oral, nasal, rectal, intrathecal, intervenous, subcutaneous, intratumor, peritumoral, local, sublingual, buccal, topical, intramuscular, by inhalation, percutaenous, vaginal, intra-arterial, intracranial, intradermal, epidural, sytemically, topical, intraperitoneal, intrapleural, endoscopic, intrabronchial, etc. An example would be the administration of a intravenous desensitizing dose followed by an intraperitoneal dose.

In another advantageous embodiment of the invention, the virus is administered by slow infusion including using an intravenous pump or slow injection over the course of 4 minutes to 24 hours.

A virus, and optionally one or more chemotherapeutic agents, is administered by a single injection, by multiple injections, or continuously. The virus is administered before, at the same time, or after the administration of chemotherapeutic agents (such as but not limited to: busulfan, cyclophosphamide, methotrexate, cytarabine, bleomycin, cisplatin, doxorubicin, melphalan, mercaptopurine, vinblastine, 5-fluorouracil, taxol, and retinoic acid). Viral therapy in accordance with the present invention is optionally combined with other treatments, including, surgery, radiation, chemotherapy (see, e.g., *Current Medical Diagnosis and Treatment*, Ed. Tierney et al., Appleton & Lange, 1997, especially pages 78-94), and biological therapy. The virus is administered before, at the same time, or after the administration of biological agents such as (1) other oncolytic agents [such as but not limited to: adenoviruses with one of its genes under transcriptional control of a prostate cell specific response element (see Rodriques, R. et al, 1997, *Cancer Res*, 57:2559-2563; adenoviruses which do not encode a Elb polypeptide capable of binding p53 (see Bischoff, J. R., et al, 1996, *Science* 274: 373-376); a herpes simplex virus that is incapable of expressing a functional gamma 34.5 gene product (see Mineta, T. et al, 1995, *Nature Medicine*, 1:938-943)]; (2) cytokines (such as but not limited to: colony stimulating factors such as GM-CSF; tumor necrosis factor, and interleukins such as IL-1, IL-2, IL-6 and IL-10); (3) viral vectors [such as but not limited to adenovirus encoding p53 (see Zhang, W W et al, 1994, *Cancer Gene Therapy*, 1:5-13)]; and (4) cancer vaccines.

In one embodiment of the invention, therapy consists of the serial treatment with antigenically distinct viruses which are cytotoxic and tumor selective via the IFN mechanism. This embodiment allows viral therapy over an extended period without immunological interference.

Another embodiment involves the treatment of patients with IFN (e.g. αIFN, βIFN or γIFN) prior to, concurrent with, or following administration of NDV (or other virus). The IFN is selected from the group class I (alpha, beta and omega) and class II (gamma), and recombinant version and analogs thereof as discussed in, for example, Sreevalsoun, T., 1995 (In: *Biologic Therapy of Cancer*, second edition, edited by V. T. DeVita, Jr., S. Hellman, and S. A. Rosenberg, J. B. Lippincott Company, Philadelphia, pp347-364). Normal cells respond to the IFN pre-treatment with an augmented IFN response to viral infection affording even greater safety to these cells. Tumor cells deficient in the IFN signaling pathway remain sensitive to killing by the virus. This allows even higher doses of viral therapy to be used. The IFN is administered in accordance with standard clinical guidelines for doses and regimens known to be effective for treating viral infections. In another embodiment of the invention, other drugs, known to affect the IFN response pathway are also optionally used to increase the sensitivity of tumor cells, or increase the resistance of normal cells to the cytocidal effects of viral infection. This class of drugs includes, but is not limited to tyrosine kinase inhibitors, cimetidine, and mitochondrial inhibitors. Hypoxia and hyperthermia are also known to modulate interferon responsiveness.

In another embodiment of the invention, immunosuppressants such as cyclosporin A, azathiaprime, and leflunomide, various corticosteroid preparations, and anti-CD-40 ligand antibodies (Foy, T. M., et al., 1993, J. Exp. Med. 178:1567-1575) are administered with the virus. Alternatively, an immunostimulatory compound, e.g., lipopeptides, can be administered with the virus.

An independent mechanism by which the amount of interferon produced in response to viral infection is increased through the use of nucleosides (Machida, H., 1979. Microbiol. Immunol. 23:643-650), nucleoside precursors, or drugs that increase the cellular concentration of one or more nucleosides, are optionally used as an adjunct to viral therapy.

Certain purine nucleoside analogs, e.g., 2-chlorodeoxyadenosine and 2'-deoxycoformycin, reduce interferon production in vivo. Such compounds are used to further effect differences in interferon sensitivities of tumor cells versus normal cells and are optionally used as an adjunct to viral therapy.

In one aspect, an effective amount of virus can be subdivided into smaller dose units and injected at the same time into different locations of the same tumor. For continuous administration, the desired agent(s) is administered via an implanted minipump or it is impregnated into a desired polymer and then transplanted into a desired location (e.g., directly into the tumor) for slow or delayed release.

A virus of the present invention is formulated as a pharmaceutical preparation by bringing it into a suitable dose form, together with at least one excipient or auxiliary, and, if desired, with one or more further active compounds. The preparations are utilized in both human and veterinary medicine. Suitable excipients include, e.g., organic and inorganic substances which are appropriate for enteral or parenteral administration, e.g., water, saline, tissue culture media, buffers, lysine, citrate, glycerol triacetate and other fatty acid glycerides, gelatin, soya lecithin, carbohydrates such as, mannitol, sucrose, lactose or starch, magnesium stearate, talc, cellulose or protein carriers, or a combination of the preceding compounds, such as mannitol/lysine, or mannitol/lysine/sucrose. The preparations are sterilized and/or contain additives, such as preservatives or stabilizers. For parenteral administration, e.g., systemic or local injection, a virus preparation is formulated, e.g., as an aqueous suspension or emulsion.

The invention also relates to a method of treating a disease in a mammal, in which the diseased cells have defects in an interferon-mediated antiviral response, comprising administering to the mammal a therapeutically effective amount of an interferon-sensitive, replication-competent, clonal virus. For example, cells infected with many viruses like hepatitis B that disable the interferon response are susceptible to the viruses of this invention. There is evidence that human immunodeficiency virus (HIV) disables the interferon response. The interferon-sensitive viruses of this invention are useful in treating such chronic virus infections such as those due to hepatitis B, hepatitis C, HIV, Epstein-Barr virus, human papilloma virus, and herpes virus.

Unless indicated otherwise herein, details and conditions of viral therapy of this invention are in accordance with U.S. application Ser. No. 08/260,536 whose disclosure is incorporated herein by reference in its entirety. The entire disclosure of all applications, patents and publications, cited above and in the figures are hereby incorporated by reference.

The following examples are illustrative, but not limiting of the methods and compositions of the present invention. Other suitable modifications and adaptations of a variety of conditions and parameters normally encountered in clinical therapy which are obvious to those skilled in the art are within the spirit and scope of this invention.

EXAMPLE 1

PPMK107, (a Triple Plaque Purified Isolate of the NDV Strain MK107) Demonstrates a Selective Cytotoxic Activity Toward many Human Cancer Cells Compared to Normal Human Cell Human tumor cells and normal cells were grown to approximately 80% confluence in 24 well tissue culture dishes. Growth medium was removed and PPMK107 was added in 10 fold dilutions ranging from $10^6$ plaque forming units (PFU)/well to $10^{-1}$ PFU/well. Controls wells with no virus added were included on each plate. Virus was adsorbed for 90 minutes on a rocking platform at 37° C. At the end of the incubation period, the viral dilutions were removed and replaced by 1 ml of growth medium. Plates were then incubated for 5 days at 37° C. in 5% CO2, then assessed qualitatively for the amount of cytopathic effect (CPE). Cytotoxicity was quantified by using a calorimetric MTT (2-[4,5-dimethylthiazol-2-yl]-2,5-diphenyl tetrazolium bromide) assay (Cell Titer 96, catalog #G4000, Promega Corporation, Madison Wis. 53711) monitored at 570 nm, that detects mitochondrial enzyme activity (Mosman, T., 1983, J. Immunol. Methods 65:55). The viability in the virus treated wells was expressed as a percent of the activity in untreated control wells. The data was plotted graphically as PFU/well vs. viability as a percent of control. The IC50 was calculated as the amount of virus in PFU/well causing a 50% reduction in the amount of viable cells.

The results are given in Tables 4, 5 and 6. PPMMK107 demonstrated a high degree of cytotoxic activity against a diverse set of human cancer cells with 30 out of 39 malignant lines having an IC50 value less than 1000 compared to the relative insensitivity of normal human cell types. The majority of human cancer cells had IC50 values that were 2 to 3 orders of magnitude lower than most normal human cell types.

TABLE 4

Summary of Cytotoxicity Assay Results

| TUMOR TYPE | CELL LINE | $IC_{50}$ (PFU/well) |
|---|---|---|
| FIBROSARCOMA | HT1080 | 2 |
| MELANOMA | SKMEL2 | 8 |
| | SKMEL3 | 2 |
| | SKMEL5 | 4 |
| | A375 | 37 |
| | MALME-3M | 778 |
| | HT144 | 28 |
| BREAST CARCINOMA | SKBR3 | 10 |
| | MDA-MB-468 | 44 |
| | ZR75-1 | 78 |
| OVARIAN CARCINOMA | SW626 | 4 |
| | PA-1 | 4 |
| | ES-2 | 13 |
| | SKOV-3 | 24 |
| | OVCAR3 | 34 |
| LUNG CARCINOMA (Large Cell, Low Passage) | H-1299 | 26 |
| GLIOBLASTOMA | U87MG | 25 |
| | U373MG | 765 |
| | U138 | 38 |
| | A172 | 207 |
| BLADDER CARCINOMA | HT1197 | 3 |
| | UM-UC-3 | 54 |
| | HT1376 | 422 |
| NEUROBLASTOMA | IMR32 | 41 |
| CERVICAL CARCINOMA | HeLa | 4 |
| PROSTATE CARCINOMA | DU-145 | 31 |
| | PC3 | $3.1 \times 10^3$ |
| COLON CARCINOMA | SW620 | 55 |
| | HT29 | $>1.0 \times 10^6$ |
| HEAD-AND-NECK CARCINOMA | KB | 4 |
| | A253 | $2.7 \times 10^3$ |
| | FaDu | $2.9 \times 10^3$ |
| | Hep-2 | $1.5 \times 10^4$ |
| NEUROEPITHELIOMA | SK-N-MC | 20 |
| SMALL CELL CA, LUNG | DMS-114 | 48 |
| | DMS-153 | $1.1 \times 10^5$ |
| | NCI-H345 | $1.2 \times 10^6$ |
| SMALL CELL CA, PROSTATE | NCI-H660 | $1.0 \times 10^5$ |
| LEUKEMIA (AML) | K562 | $5.4 \times 10^4$ |

TABLE 5

Summary of Cytotoxicity Assay Results Using Normal Human Cells

| CELL TYPE | CELL | $IC_{50}$ (PFU/well) |
|---|---|---|
| Keratinocytes | NHEK | $9.0 \times 10^6$ |
| Fibroblasts | CCD-922 | $1.4 \times 10^5$ |
| | NHDF | $8.1 \times 10^3$ |
| Endothelial Cells | HPAEC | $5.2 \times 10^4$ |
| Renal Cells | RPTEC | $2.7 \times 10^4$ |
| Melanocytes | NHEM | $5.1 \times 10^4$ |
| Astrocytes | NHA | $3.8 \times 10^3$ |

TABLE 6

Summary of Cytotoxicity Assay Results Using Rapidly Proliferating Normal Human Cells

| CELL TYPE | RATE OF PROLIFERATION | | $IC_{50}$ (PFU/well) |
|---|---|---|---|
| | IN VIVO | IN VITRO | |
| Bone Marrow Cells CD34+ Enriched to 50% | Moderate to High | High | $6.2 \times 10^3$ |
| Breast Epithelial Cells | Very Low[1] | High[1] | 30 |

[1] Human breast epithial cells tested (HMEC) had a high rate of proliferation after stimulation with bovine pituitary extract and human epidermal growth factor. In marked contrast, normal breast epithelial cells almost always have a very low degree of proliferation in adult women with cancer.

EXAMPLE 2

Use of PPMK107 for the Intratumoral Treatment of Human Tumor Xenografts (<10 mm and >5 mm) in Athymic Mice Athymic mice were injected intradermally with 10 million human tumor cells. After tumors reached a size range from between 5 and 10 mm, a single injection of PPMK107 (at a dose of $3\times10^8$ PFU) or saline was given. Almost all tumor types exhibited a rate of complete or partial regression of 50% to 100% (see Table 7) in mice treated with PPMK107. The one exception is the case of the U87MG experiment (experiment I): Although only one of 9 tumors treated with PPMK107 completely regressed, two more virus-treated tumors showed regression of 32% and 20% and two more virus-treated tumors had slower growth than all 8 tumors treated with saline control. Tumor regression was virtually absent in the saline control treated tumors: In all of these experiments (A through I listed in Table 7) only one of 73 control tumors showed regression. These results indicate that diverse tumor types showed responses to intratumoral PPMK107 treatment.

To examine virus replication within the tumor, immunohistochemical staining for viral antigen (using a monoclonal antibody against the NDV P protein) was performed using the subcutaneous HT1080 fibrosarcoma model. Within 30 minutes of intratumoral injection of $3\times10^8$ PFU of PPMK107, the tumor tissue was negative for viral antigen. However, by day 2 post treatment, intense immunostaining for viral antigen was seen within the tumor, indicating virus replication within the tumor. Importantly, virus replication was specific for the tumor tissue since the neighboring connective tissue and skin was negative for viral antigen.

EXAMPLE 3

Use of PPMK107 for the Intravenous Treatment of Human Tumor Xenografts (<8.5 mm and >5.5 mm) in Athymic Mice Athymic mice were injected intradermally with 10 million human HT1080 fibrosarcoma cells. After tumors reached a size range from between 5 and 8 mm, a intravenous injection(s) of PPMK107 or saline were made. As shown in Table 8, at the highest virus dose level ($1\times10^9$ PFU) complete tumor regression was seen in all seven mice. Single injections of $3\times10^8$ and $6\times10^7$ resulted in regression rates of over 90%. While a single IV injection of $3\times10^8$ gave only a 55% rate of tumor regression, three IV injections at this dose level yielded a 100% rate of response. Mice treated with IV saline exhibited no evidence of tumor regression. These results indicate that subcutaneous HT1080 tumors are very responsive to IV treatment with PPMK107.

TABLE 8

PPMK107 intravenous treatment of subcutaneous human HT1080 fibrosarcoma xenografts (<8.5 mm and >5.5 mm) in athymic mice

| Dose | Schedule | N | Complete Regression | Complete + partial Regression | % Regression |
|---|---|---|---|---|---|
| 1.00E+09 | One Injection | 7 | 7 | 7 | 100% |
| 3.00E+08 | One Injection | 10 | 9 | 10 | 100% |
| 6.00E+07 | One Injection | 11 | 10 | 10 | 91% |
| 2.00E+07 | One Injection | 11 | 5 | 6 | 55% |
| 2.00E+07 | Three Injections Every Other Day | 7 | 5 | 7 | 100% |
| Saline | One Injection | 10 | 0 | 0 | 0% |
| Saline | Three Injections Every Other Day | 6 | 0 | 0 | 0% |

EXAMPLE 4

First Experiment Using PPMK107 for Intratumoral Treatment of Large A375 Melanoma Xenografts in Athymic Mice Athymic mice were injected intradermally with 10 million A375 human melanoma cells. Ten days later, tumors of various sizes were treated with a single injection PPMK107 (doses of $3\times10^8$, $9\times10^8$, and $1.5\times10^9$ PFU) or saline. For those tumor with a single largest dimension of 10 to 11 mm, all nine completely regressed in response to intratumoral treatment with these doses of PPMK107, while of those tumors with a single largest dimension of 8 to 9.5 mm, twelve out of 24 completely regressed in response to virus therapy (P<0.008; Table 9, section A). No tumor regression was seen in any mouse treated with saline.

These same tumors when sorted by tumor volume also indicated a high percentage of complete regression in those of larger tumor volume. In response to these doses PPMK107, complete regression occurred in 14 out of 17 tumors with volumes >300 mm$^3$ (range of 304 to 397 mm$^3$) and in 7 out of 16 tumors with volumes <300 mm$^3$ (range of 144 to 295; P <0.023; Table 9, section B).

These results indicate that tumors at least 1 cm in length or 300 mm$^3$ in volume were at least as sensitive, if not more sensitive, to intratumoral PPMK107 treatment than smaller tumors.

TABLE 7

PPMK107 intratumoral treatment of subcutaneous human tumor xenografts (<10 mm and >5 mm) in athymic mice

| Tumor | Tumor Type | Expt # | Dose | N | Complete Regression | Complete + partial Regression |
|---|---|---|---|---|---|---|
| HT1080 | Fibrosarcoma | A | 3.00E+08 | 12 | 11 | 11 |
|  |  | B | 3.00E+08 | 9 | 8 | 8 |
|  |  | C | 3.00E+08 | 8 | 8 | 8 |
| PA-1 | Ovarian Carcinoma | D | 3.00E+08 | 9 | 9 | 9 |
| KB | Oral Carcinoma | E | 3.00E+08 | 12 | 7 | 10 |
| SKMEL5 | Melanoma | F | 3.00E+08 | 8 | 5 | 7 |
| A375 | Melanoma | G | 3.00E+08 | 8 | 5 | 7 |
|  |  | H | 3.00E+08 | 8 | 1 | 4 |
| U87MG | Glioblastoma | I | 3.00E+08 | 9 | 1 | 1 |

EXAMPLE 5

Second Experiment Using PPMK107 for Intratumoral Treatment of Large A375 Melanoma Xenografts in Athymic Mice Tumors were established as in Example 4 ten days after tumor cell inoculation. Treatment consisted of various doses of PPMK107 ($3 \times 10^6$ PFU, $3 \times 10^7$, $3 \times 10^8$, and $1.5 \times 10^9$) or saline. For tumors 10 to 11.5 mm in single largest dimension, complete or partial (at least 50%) regression occurred in all 28 tumors treated with PPMK107 using these doses in contrast to no regression in any of the saline-treated mice (Table 10, section A).

When these same tumors were sorted by tumor volume, all 26 tumors greater than 300 mm³ (range: 309 to 525 mm³) regressed completely or partially (at least 50%) in response to PPMK107 in contrast to none of the saline treated mice (Table 10, section B).

These results confirm that tumors at least 1 cm in length or 300 mm³ in volume are sensitive to intratumoral PPMK107 treatment.

TABLE 9

Intratumoral PPMK107 Treatment of Intradermal A375 Melanoma Xenografts

A. Tumors Sorted Based on the Single Largest Dimension

| Treatment | Dosage | Tumor Dimension: 8 to 9.5 mm | | | Tumor Dimension: 10 to 11 mm | | |
|---|---|---|---|---|---|---|---|
| | | N | Complete Regression | % | N | Complete Regression | % |
| PPMK107 | $1.5 \times 10^9$ | 8 | 2 | 25% | 3 | 3 | 100% |
| PPMK107 | $9.0 \times 10^8$ | 8 | 7 | 88% | 3 | 3 | 100% |
| PPMK107 | $3.0 \times 10^8$ | 8 | 3 | 38% | 3 | 3 | 100% |
| Total | | 24 | 12 | 50% | 9 | 9 | 100% a |
| Saline | | 6 | 0 | 0% | 3 | 0 | 0% |

B. Tumors Sorted Based on the Tumor Volume

| Treatment | Dosage | Tumor Volume: <300 mm³ | | | Tumor Volume: >300 mm³ | | |
|---|---|---|---|---|---|---|---|
| | | N | Complete Regression | % | N | Complete Regression | % |
| PPMK107 | $1.5 \times 10^9$ | 6 | 2 | 33% | 5 | 3 | 60% |
| PPMK107 | $9.0 \times 10^8$ | 4 | 3 | 75% | 7 | 7 | 100% |
| PPMK107 | $3.0 \times 10^8$ | 6 | 2 | 33% | 5 | 4 | 80% |
| Total | | 16 | 7 | 44% | 17 | 14 | 82% b |
| Saline | | 8 | 0 | 0% | 1 | 0 | 0% | a $P < 0.008$ for complete regression in the PPMK107 10-11 mm group vs. the PPMK107 8-9.5 mm treated group
b $P < 0.023$ for complete regression in the PPMK107-treated >300 mm³ group vs. the PPMK107-treated <300 mm³ group

TABLE 10

Intratumoral PPMK107 Treatment of Intradermal A375 Melanoma Xenografts.

| Treatment | Dose | N | Complete | % | Complete + Partial | % |
|---|---|---|---|---|---|---|
| A. Tumors 10 to 11.5 mm (Sorted Based on the Single Largest Dimension) | | | | | | |
| | $1.5 \times 10^9$ | 7 | 7 | 100% | 7 | 100% |
| | $3.0 \times 10^8$ | 7 | 6 | 86% | 7 | 100% |
| | $3.0 \times 10^7$ | 7 | 5 | 71% | 7 | 100% |
| | $3.0 \times 10^6$ | 7 | 5 | 71% | 7 | 100% |
| All PPMK107 Groups | | 28 | 23 | 82% | 28 | 100% |
| Saline | | 6 | 0 | 0% | 0 | 0% |
| B. Tumors >300 mm³ (Sorted Based on the Tumor Volume) | | | | | | |
| | $1.5 \times 10^9$ | 7 | 7 | 100% | 7 | 100% |
| | $3.0 \times 10^8$ | 7 | 6 | 86% | 7 | 100% |
| | $3.0 \times 10^7$ | 6 | 4 | 67% | 6 | 100% |
| | $3.0 \times 10^6$ | 6 | 4 | 67% | 6 | 100% |
| All PPMK107 Groups | | 26 | 21 | 81% | 26 | 100% |
| Saline | | 5 | 0 | 0% | 0 | 0% |

EXAMPLE 6

Third Experiment Using PPMK107 for Intratumoral Treatment of Large A375 Melanoma Xenografts in Athymic Mice Tumors were established as in Example 4 nineteen days after tumor cell inoculation. Intratumoral treatment consisted of various doses of PPMK107 ($3\times10^8$, $3\times10^6$, $3\times10^5$, $3\times10^4$, $3\times10^3$, $3\times10^2$ PFU) or saline. For tumors 12.5 to 14 mm in single largest dimension (volume range: 632 to 787 mm$^3$; average volume 698 mm$^3$), tumor regressions of at least 50% occurred in two out of three mice treated with $3\times10^8$ PFU in contrast to no regression in both saline-treated mice (Table 11). Using the same dose of PPMK107 ($3\times10^8$ PFU) to treat tumors with a single largest dimension of 10 to 12 mm (volume range: 320 to 600 mm$^3$; average volume: 411 mm$^3$), seven of 8 mice exhibited regression of at least 25% (P<0.001 for regression of at least 25% compared to the saline treated mice which exhibited no regressions, Table 11). Regressions of at least 25% for tumors of length 10 to 12 mm tumors were also seen in mice treated with $3\times10^6$ PFU, $3\times10^5$ PFU, $3\times10^4$ PFU, and $3\times10^3$ PFU, but not for mice treated with $3\times10^2$ PFU or saline (Table 11).

These results confirm that tumors at least 1 cm in length or 300 mm$^3$ in volume are sensitive to intratumoral PPMK107 treatment.

EXAMPLE 7

Fourth Experiment Using PPMK107 for Intratumoral Treatment of Large A375 Melanoma Xenografts in Athymic Mice Tumors of largest dimension 10 to 12 mm were established as in Example 4 thirteen days after tumor cell inoculation. Intratumoral treatment consisted of a single injection of $3\times10^8$ PFU of PPMK107 or saline. Volumes of those tumors treated with PPMK107 ranged from 295 to 600 mm$^3$ (average tumor volume of 437 mm$^3$). Groups of mice in each treatment group were euthanized on days 0, 2, 3, 4, 7, and 14 for tumor histology. For those mice observed for a minimum of 4 days, eleven out to 12 mice treated with PPMK107 exhibited regression of at least 25% compared to none of 8 in the saline group (P<0.0001, Table 12). At 2 days after PPMK107 treatment, two tumors already exhibited signs of regression but the degree of regression was less than 25%.

TABLE 11

3rd Experiment Using PPMK107 for the Intratumoral Treatment of A375 Melanoma Xenografts (at least 10 mm in size)

| Treatment | N | Volume Range | Avg Volume | Regressions Complete | Partial[a] | >25% & <50%[b] | Total # of Regressions[c] | % Regressions[c] | |
|---|---|---|---|---|---|---|---|---|---|
| | Size: 12.5 to 14 mm | | | | | | | | |
| 3.0E+08 | 3 | 632 to 787 | 698 | 1 | 1 | 0 | 2 | 67% | |
| Saline | 2 | 717 to 860 | 788 | 0 | 0 | 0 | 0 | 0% | |
| | Size: 10 to 12 mm | | | | | | | | |
| 3.0E+08 | 8 | 320 to 600 | 411 | 0 | 3 | 4 | 7 | 88% | d |
| 3.0E+06 | 8 | 425 to 662 | 502 | 0 | 0 | 2 | 2 | 25% | |
| 3.0E+05 | 8 | 245 to 600 | 421 | 0 | 0 | 1 | 1 | 13% | |
| 3.0E+04 | 8 | 336 to 600 | 477 | 0 | 0 | 1 | 1 | 13% | |
| 3.0E+03 | 8 | 281 to 542 | 349 | 2 | 0 | 0 | 2 | 25% | |
| 3.0E+02 | 8 | 281 to 662 | 372 | 0 | 0 | 0 | 0 | 0% | |
| Saline | 8 | 379 to 666 | 518 | 0 | 0 | 0 | 0 | 0% | |

[a]Partial Regression is defined as regression less than 100% and equal to or greater than 50%.
[b]"Regression >25% & <50%" is defined as tumor regression greater than 25% and less than 50%.
[c]Includes all tumor regression that is greater than 25%.
d P < 0.001 for Regression greater than 25% in the 3E+08 group vs the saline group.

TABLE 12

4th Experiment Using PPMK107 for the intratumoral Treatment of A375 Melanoma Xenografts (at least 10 mm in size)

| | Tumor Size: 10 to 12 mm | | | | | | | |
|---|---|---|---|---|---|---|---|---|
| Treatment | Day Euthanized Post Treatment | N | Regressions Complete | Partial[a] | >25% & <50%[b] | Total # of Regressions[c] | % Regressions[c] | |
| 3.0E+08 | 14 Days | 3 | 0 | 2 | 1 | 3 | 100% | |
| 3.0E+08 | 7 Days | 3 | 0 | 2 | 1 | 3 | 100% | |
| 3.0E+08 | 4 Days | 3 | 0 | 2 | 1 | 3 | 100% | |
| 3.0E+08 | 3 Days | 3 | 0 | 0 | 2 | 3 | 67% | |
| 3.0E+08 | All PPMK107 Groups | 12 | 0 | 6 | 5 | 11 | 92% | d, e |
| Saline | 14 Days | 2 | 0 | 0 | 0 | 0 | 0% | |
| Saline | 7 Days | 2 | 0 | 0 | 0 | 0 | 0% | |

TABLE 12-continued

4th Experiment Using PPMK107 for the intratumoral Treatment of A375 Melanoma Xenografts (at least 10 mm in size)

Tumor Size: 10 to 12 mm

| Treatment | Day Euthanized Post Treatment | N | Complete | Partial[a] | >25% & <50%[b] | Total # of Regressions[c] | % Regressions[c] |
|---|---|---|---|---|---|---|---|
| Saline | 4 Days | 2 | 0 | 0 | 0 | 0 | 0% |
| Saline | 3 Days | 2 | 0 | 0 | 0 | 0 | 0% |
| Saline | All Saline Groups | 8 | 0 | 0 | 0 | 0 | 0% |

[a] Partial Regression is defined as regression less than 100% and equal to or greater than 50%.
[b] "Regression >25% & <50%" is defined as tumor regression greater than 25% and less than 50%.
[c] Includes Regression that is at least 25%.
d $P < 0.03$ for Complete or Partial Regression in the PPMK107 group of 12 mice vs the saline group of 8 mice.
e $P < 0.0001$ far Regression at least 25% in the PPMK107 group of 12 mice vs the saline group of 8 mice.

EXAMPLE 8

Fifth Experiment Using PPMK107 for Intratumoral Treatment of Large A375 Melanoma Xenografts in Athymic Mice Tumors of largest dimension 10 to 12 mm were established as in Example 4 twenty days after tumor cell inoculation. Intratumoral treatment consisted of a single injection of $3 \times 10^8$ PFU of PPMK107 or saline. Volumes of those tumors treated with PPMK107 ranged from 361 to 756 mm$^3$ (average tumor volume of 551 mm$^3$). Nine out of 10 mice treated with PPMK107 exhibited a regression of at least 25% compared to none of 10 in the saline group (P<0.0001, Table 13).

EXAMPLE 9

First Experiment Using PPMK107 for Intravenous Treatment of Large HT1080 Fibrosarcoma Xenografts Athymic mice were injected subcutaneously with 10 million HT1080 human fibrosarcoma cells. Six days later, tumors were treated with a single injection PPMK107 (at a dose of $1.5 \times 10^9$ PFU) or saline. For those tumors 10 to 11 mm in single largest dimension, five out of six tumors completely or partially regressed in response to a single intravenous injection of PPMK107 compared to none of the saline treated tumors (Table 14, P<0.025). These results indicate that tumors at least 1 cm in length are sensitive to intravenous PPMK107 treatment.

TABLE 13

5th Experiment Using PV701 for the Intratumoral Treatment of A375 Melanoma Xenografts (at least 10 mm in size)

Size: 10 to 12 mm

| Treatment | N | Complete | Partial[a] | >25% & <50%[b] | Total # of Regressions[c] | % Regressions[c] | |
|---|---|---|---|---|---|---|---|
| 3.0E+08 | 10 | 0 | 4 | 5 | 9 | 90% | d, e |
| Saline | 10 | 0 | 0 | 0 | 0 | 0% | |

[a] Partial Regression is defined as regression less than 100% and equal to or greater than 50%.
[b] "Regression >25% & <50%" is defined as tumor regression greater than 25% and less than 50%.
[c] Includes all tumor regression that is at least 25%.
d $P < 0.05$ for Complete or Partial Regression in the PV701 group of vs the saline group.
e $P < 0.0001$ for all tumor regression at least 25% in the PV701 group vs the saline group.

TABLE 14

Intravenous Treatment of Subcutaneous HT1080 Human Fibrosarcoma Xenografts in Athymic Mice

| Treatment | Dose | Size: 10 to 11 mm | | Regressions | | | |
|---|---|---|---|---|---|---|---|
| | | N | Complete | % | Complete + Partial | % | |
| PPMK107 | 1.5E+09 | 6 | 4 | 67% | 5 | 83% | a |
| Saline | | 4 | 0 | 0 | 0 | 0 | | a $P < 0.025$ (by Fisher's exact test) for complete or partial regression (at least 50% regression) in the PPMK107 treated group compared to the saline Group

EXAMPLE 10

Specific Clearing of PPMK107 Infection from Normal but not Tumor Cells

In order to examine the mechanism of tumor-specific killing by NDV strain PPMK107, representative tumor cells were chosen based on the following criteria: a) ability to form tumors as xenografts in athymic mice; b) the tumor xenografts are specifically killed in vivo following administration of PPMK107; c) the tumors cells exhibit killing by PPMK107 in vitro at virus concentrations that are several logs below the concentration to kill resistant, normal cells; and d) tumor cells must be easily distinguished from the normal cells when present as a co-culture. Xenograft tumors comprised of KB head and neck carcinoma cells exhibit 83% complete or partial regression in response to a single intratumoral injection of PPMK107, are more than four logs more sensitive to killing by PPMK107 in vitro than are normal primary skin fibroblasts (CCD922-sk), and are easily distinguished from CCD922-sk cells when present as a co-culture.

Accordingly, co-cultures of KB and CCD922-sk cells were infected at a multiplicity of infection (m.o.i., the ratio of virus added per cell) of 0.0005 and the course of the infection followed for 5 days by immunohistochemical staining for a viral antigen (NDV P protein). Infection of normal cells peaked at 2 days with little or no apparent cell death as determined by visual inspection of the cell monolayer. On the third day post-infection the amount of viral expression in the normal cells decreased significantly, while infection of the tumor cells was clearly apparent. The amount of viral antigen virtually disappeared in the normal cells on days 4 and 5, while the infection in the tumor cells progressed rapidly through the tumor cell population resulting in destruction of the majority of the tumor cells present in the co-culture.

Thus, normal cells were infected and easily cleared the infection in a manner consistent with the anti-viral effects of IFN. The tumor cells were unable to establish an anti-viral state in response and were killed by the unabated viral growth, despite the presence of physiologically effective concentrations of IFN secreted into the media by the normal cells.

EXAMPLE 11

Demonstration that Interferon is an Important Component of Viral Clearing in Normal CCD922-sk Cells The hypothesis that interferon was mediating the ability of CCD922-sk cells to clear the infection of PPMK107 was tested. Polyclonal neutralizing antibodies to human interferon-α or human interferon-β, used alone or in combination, were added daily to cultures of CCD922-sk cells infected with PPMK107 at an moi of 0.0005 and the progress of the infection followed for three days. The amount of viral antigen present in the cells increased in proportion to the concentration of neutralizing antibody, with the effect of the anti-interferon-β antibody being more marked than that of the anti-interferon-α antibody; consistent with reports that fibroblasts produce predominantly the beta form of interferon.

The ability to make the normally insensitive cells more susceptible to infection with PPMK107 through the addition of neutralizing antibody to interferon supports the hypothesis that a key difference between the sensitivity of normal and tumor cells to killing by PPMK107 lies in the ability of normal cells, but not tumor cells, to establish an interferon-mediated anti-viral response.

EXAMPLE 12

Demonstration that Interferon-β is an Important Component of Viral Clearing in Other Normal Cells In this experiment, it was determined that another normal cell (NHEK, normal human epithelial cells) known to be quite resistant to killing by PPMK107, was made more sensitive through the addition of polyclonal anti-interferon-β antibody to a culture of infected cells. NHEK (normal human epithelial keratinocyte) cells were infected at an moi of either 0.0005 or 0.05 and had antibody added daily over five days.

In the cultures infected at the low moi (0.0005), antibody dependent augmentation of viral antigen expression was clear at five days post-infection, but was less clear earlier in the experiment. Antibody addition to cultures infected with PPMK107 at an moi of 0.05 resulted in a marked increase in viral antigen at 4 and 5 days post-infection. At 2 and 3 days post-infection the addition of neutralizing antibody resulted in less accumulation of viral antigen (FIG. 1).

The culture supernatants from the high moi samples were also titrated for the amount of infectious virus present by plaque assay on human HT1080 fibrosarcoma tumor cells; the standard assay system in our laboratory. Results from this analysis demonstrated that at five days post-infection there was 19-fold increase in the amount of infectious virus in the antibody-treated cultures relative to mock-treated controls FIG. 1).

These results suggest a general mechanism by which normal cells are protected from killing by PPMK107 through an interferon-related mechanism.

EXAMPLE 13

Comparison of the Effect of Interferon-β on PPMK107 Infection in Tumor and Normal Cells A comparison of the effect of exogenously added interferon-β on the infection of normal (CCD922-sk) and tumor cells of high (KB) or intermediate (HEp2) sensitivity PPMK107 was performed. Separate cultures of the three cells were treated with interferon-β at 20, 200, or 2000 units/ml 1 day pre- and 2 days post-infection at an moi of 0.0005.

At 3 days post-infection the low level of viral antigen expression present in the normal cells was eliminated at all doses of interferon used. Conversely, the addition of interferon to the highly sensitive KB tumor cells at concentrations of 2 or 200 units/ml decreased relative levels of viral antigen expression 2-fold, with complete suppression at 1000 units/ml interferon. The intermediately sensitive HEp-2 cells responded to the exogenous interferon by clearing viral antigen expression at all of the interferon doses used (FIG. 2).

The pattern of sensitivity in the KB and CCD922-sk cells to the anti-viral effects of exogenously added interferon-β was inversely proportional to the sensitivity of these cells to killing by PPMK107. The ability of the HEp-2 cells to respond to the effects of interferon indicates that these cells are able to efficiently utilize the concentrations of interferon used in this experiment. Similarly, the response of the KB cells to the high doses of interferon suggests that the inability to establish an interferon-mediated anti-viral response does not result from an absolute defect in the interferon pathway, but rather a relative insensitivity compared to normal cells.

EXAMPLE 14

Effect of Low Concentrations of Interferon-β on the Infection of Normal and Tumor Cells by PPMK107

In this experiment normal (CCD922-sk) and tumor (KB) cells were treated with low concentrations of interferon-β (0.2, 2, and 20 units/ml) 1 day before and 2 days post-infection with PPMK107 at an moi of 0.05.

Under these conditions the normal cells experienced a dose-dependent decrease in the amount of viral antigen, while the relative levels of viral antigen in the tumor cells was unaffected by the addition of exogenous interferon (FIG. 3).

EXAMPLE 15

PPMK107 Purification

Method A

PPMK107 was derived from the mesogenic Newcastle disease virus strain Mass-MK107 by triple plaque purification. Approximately 1000 PFUs (plaque forming units) of live PPMK107 were inoculated into the allantoic fluid cavity of each 10 day old embryonated chicken egg. After incubation at 36° C. for 46 hours, the eggs were chilled and then the allantoic fluid was harvested. Cells and cell debris were removed from the allantoic fluid by centrifugation at 1750×g for 30 minutes. The clarified allantoic fluid (superatant containing virus) was then layered over a 20%/55% discontinuous sucrose gradient) and centrifuged at approximately 100,000×g for 30 minutes. The purified virus was harvested from the 20%/55% interface and dialyzed against saline to remove the sucrose.

Method B

In another advantageous embodiment, the clarified allantoic fluid was frozen at −70° C. After thawing, the fluid was maintained at 1 to 4 C overnight and then the contaminating material was removed from the virus suspension by means of centrifugation (1750×g for 30 minutes). This material was further processed using the discontinuous sucrose gradient on the ultracentrifuge as above.

Method C

In another advantageous embodiment, ultracentrifugation on the discontinuous sucrose gradient was accomplished by means of a continuous flow ultracentrifuge.

Method D

In another advantageous embodiment, harvested allantoic fluid is diluted with a buffer containing 5% mannitol and 1.0% 1-lysine, pH 8.0 (ML buffer) and is clarified and exchanged with ML buffer by tangential flow filtration (TFF) through filters with a nominal pore size of 0.45µ. The permeate containing the clarified virus in ML buffer is collected and virus is purified by TFF through filters with a nominal cut-off of 300,000 daltons in ML buffer. The concentrated, purified virus in ML buffer is collected as the retentate from this step and is again diluted with ML buffer before being applied to a Sephacryl S500 (Pharmacia) gel permeation column equilibrated with ML buffer. Fractions containing purified virus are collected, pooled and can be reconcentrated by TFF through filters with a nominal cut-off of 300,000 daltons with ML buffer.

Results

Clonal Virus

After generation of PPMK107 by plaque purification, eight individual molecular clones from the population of virions were found to have an identical sequence (e.g., a homology of 100%) of over 300 contiguous nucleotides within the fusion protein gene of NDV. PPMK107 is a clonal virus with a high degree of genetic homogeneity.

PFU/mg protein

One quantitative means of measuring purity is by determination of a PFU/mg protein. Higher values indicate a greater level of purity. Using Method A, PFU/mg values of at least $4.8\times10^{10}$ were achieved (see Table 15). Using Method C, PFU/mg protein values of at least $2.0\times10^{10}$ were achieved. For a mesogenic strain of NDV, a literature value for this measurement of purity has not been found. The best estimate for a mesogenic strain of NDV is the virus preparation (NDV MassMK107, lot RU2, prepared as in Faaberg K S and Peeples, M E, 1988, J Virol 62:586; and Bratt, M A and Rubin, H. 1967, Virology 33:598-608). This RU2 lot was found to have a PFU/mg of $1.3\times10^9$ PFU/mg of protein. The purity values achieved by Method A are approximately 40 times better than what the Peeples method achieved (see Table 15).

Particle per PFU Ratio

Another quantitative means of measuring purity is by determination of a ratio of particles per PFU. Lower values indicate a greater level of purity. Particle counts were done by electron microscopy using standard methods. Using either Method A or Method B, particles per PFU values near one were achieved (Table 15).

TABLE 15

Virus Purity

| Virus Preparation Method | Virus | Lot # | PFU per mg protein | Particle per PFU |
|---|---|---|---|---|
| Preferred Method A | PPMK107 | L2 | $4.8\times10^{10}$ | 0.80 |
| | | L4 | $6.9\times10^{10}$ | NT[a] |
| | | L5 | $6.6\times10^{10}$ | NT |
| | | L6 | $7.7\times10^{10}$ | 0.55 |
| | | L7 | $6.1\times10^{10}$ | NT |
| Preferred Method C | PPMK107 | D004 | $2.0\times10^{10}$ | 0.32 |
| | | D005 | $4.5\times10^{10}$ | 0.52 |
| | | D010 | $4.4\times10^{10}$ | NT |
| Preferred Method D | PPMK107 | RD2 | $5.6\times10^{10}$ | NT |
| | | RD3 | $5.0\times10^{10}$ | NT |

[a]NT, Not Tested

Virus preparations using Methods A and C also permited purification of NDV to a level substantially free of contaminating egg proteins. For the PPMK107 lot 7 preparation using Method A, ovalbumin, was not detectable in a Western blot using (1) $1.7\times10^9$ PFU of purified virus per well (3.3 cm in width) -run on an SDS-PAGE (sodium dodecyl sulfate-polyacrylamide gel electrophoresis) gel (1 mm thick); (2) a nitrocellulose membrane for transfer; and (3) rabbit anti-ovalbumin (Cappel rabbit IgG fraction at a 1:200 dilution of a 4 mg/ml antibody concentration). For PPMK107 preparations using Method D and analyzed by SDS-PAGE followed by silver staining, no band corresponding to ovalbumin was observed.

EXAMPLE 16

Use of PPMK107 To Prevent Deaths from ES-2 Ovarian Carcinoma Ascites in Athymic Mice In this experiment, all of the athymic mice (female, NCR nu/nu, 8 weeks old) were given an intraperitoneal injection of $10^6$ ES-2 cells. Seven days later before ascites had developed, they were treated intraperitoneally with saline or PPMK107 (at $1\times10^9$ PFU). As shown in FIG. 4, there was a markedly improved survival in the animals treated with PPMK107 compared to saline. The majority of the mice in the saline treated group had developed ascites by seven days post-treatment and by day 38, all of these animals had died. In marked contrast, 92% of the mice treated with PPMK107 were still alive by day 38 and 25% of these animals were long term survivors (>120 day survival).

EXAMPLE 17

PPMK107 Treatment of ES-2 Ovarian Carcinoma in Athymic Mice When Ascites is Present In this experiment, all of the athymic mice (female, NCR nu/nu, 8 weeks old) were given an intraperitoneal injection of $10^6$ ES-2 cells. Fourteen days later when the majority of mice had developed ascites, the mice without ascites were excluded and the mice with ascites were randomized into 7 intraperitoneal treatment groups (PPMK107—one treatment on day 0; PPMK107—two treatments for the first week; PPMK107—one treatment each week; PPMK107—two treatments each week; saline-one treatment on day 0; saline-two treatments for the first week; saline-two treatments each week). A dose of $1\times10^9$ PFU/mouse was used for each virus treatment. All of the mice before the first treatment and any additional treatments were drained of the ascites fluid. Day 0 refers to the day of first treatment.

The degree of ascites for each mouse was quantified and noted as follows:

| Ascites Score | Degree of Ascites |
|---|---|
| 1.0 | Animal appears normal—little or no ascites present |
| 2.0 | Abdomen slightly distended; animal is capable of normal functions |
| 3.0 | Abdomen distended; animal is slow-moving, hunched with a staggered gait. |
| 4.0 | Abdomen completely distended; animal moribund |
| 5.0 | Death after ascites development |

As shown in Table 16, all of the saline-treated animals had more advanced ascites than the PPMK107-treated animals on both days 7 and 10. On day 7 post initial treatment, each the saline group had average ascites scores above 3.5 while all of the PPMK107-treated groups had average ascites scores at 3.0 or below. Similarly on day 10 post initial treatment, each the saline group had average ascites scores above 4.5 while all of the PPMK107-treated groups had average ascites scores at 4.1 or below. These results indicate that ascites fluid production was markedly decreased in virus-treated animals compared to saline controls.

TABLE 16

PPMK107 Treatment of ES-2 Ovarian Carcinoma in Athymic Mice When Ascites is Present.

| Treatment | # of Mice | Average Ascites Score, Day 7 | Average Ascites Score, Day 10 |
|---|---|---|---|
| Saline × 1 | 12 | 4.3 | 4.7 |
| Saline × 2 | 12 | 3.7 | 4.6 |
| Saline × 2 each wk | 12 | 4.3 | 4.8 |
| PPMK107 × 1 | 17 | 3.0 | 4.1 |
| PPMK107 × 2 | 17 | 2.3 | 3.6 |
| PPMK107 × 1 each wk | 17 | 2.6 | 2.6 |
| PPMK107 × 2 each wk | 17 | 2.2 | 3.6 |

EXAMPLE 18

Use of a Desensitizing Dose of PPMK107 to Reduce the Lethality of a Subsequent Dose of PPMK107

C57BL/6 mice (seven weeks old) were injected intravenously on day 0 with either saline or a desensitizing dose of PPMK107 ($3\times10^8$ PFU/mouse). Two days later each set of mice were further subdivided into groups for intravenous dosing with saline or PPMK107 (at doses of $1\times10^9$, $2.5\times10^9$, $5\times10^9$, and $1\times10^{10}$ PFU/mouse). As shown in Table 17, when saline was used to pretreat the mice, deaths were recorded in the mice subsequently dosed with $2.5\times10^9$, $5\times10^9$, and $1\times10^{10}$ PFU. The doses of $5\times10^9$ and $1\times10^{10}$ PFU were 100% lethal to the mice pretreated with saline. In contrast, no deaths were seen in any group of mice given a desensitizing dose of PPMK107 on day 0 followed by PPMK107 injection two days later at dose levels up to $1\times10^{10}$ PFU. These data indicate that PPMK107 can be used to prevent the lethality of subsequent dosing with this same agent. Furthermore, the maximal tolerated dose of PPMK107 can be raised by an approximate order of magnitude when using this virus as a desensitizing agent.

TABLE 17

Use of a Desensitizing Dose of PPMK107 to Reduce the Lethality of a Subsequent Dose of PPMK107.

| Group | Injection on Day 0 | Dose on Day 2 | # of Mice | # of Deaths | % Lethality |
|---|---|---|---|---|---|
| 1 | Saline | Saline | 8 | 0 | 0 |
| 2 | Saline | PPMK107, 1.0E+09 | 8 | 0 | 0 |
| 3 | Saline | PPMK107, 2.5E+09 | 8 | 3 | 38 |
| 4 | Saline | PPMK107, 5.0E+09 | 8 | 8 | 100 |
| 5 | Saline | PPMK107, 1.0E+10 | 8 | 8 | 100 |
| 6 | PPMK107, 3E+08 | Saline | 8 | 0 | 0 |
| 7 | PPMK107, 3E+08 | PPMK107, 1.0E+09 | 8 | 0 | 0 |
| 8 | PPMK107, 3E+08 | PPMK107, 2.5E+09 | 8 | 0 | 0 |
| 9 | PPMK107, 3E+08 | PPMK107, 5.0E+09 | 8 | 0 | 0 |
| 10 | PPMK107, 3E+08 | PPMK107, 1.0E+10 | 8 | 0 | 0 |

EXAMPLE 19

Slower Intravenous Injection Rate Reduces the Toxicity of PPMK107

Twenty two athymic mice (8 weeks old) were anesthetized with a combination of ketamine/xylazine and placed into a restrainer to help inhibit their movement during the injection process to allow for either a slow or rapid injection of PPMK107. For the slow injection group, 0.2 mL of $4\times10^9$ PFU of PPMK107 in saline was injected intravenously over a 4 minute period with 0.01 mL given every 10 to 15 seconds.

The rapid injection group received the same dose and volume but over a 30 second period. As shown in Table 18, the animals receiving their dose of PPMK107 over 4 minutes had half as much maximal weight loss (recorded on day 2 after dosing) as the animals receiving the same IV dose over 30 seconds. These results indicate that PPMK107 has less toxicity and is safer for intravenous administration when injected at such slower rates.

TABLE 18

Slower IV Injection of PPMK107 Results in Reduced Toxicity.

| Group | Length of Time That Dose was Administered | # of Mice | Maximal Percent Weight Loss |
|---|---|---|---|
| Rapid Injection of 4E+09 | 30 seconds | 11 | 12% |

TABLE 18-continued

Slower IV Injection of PPMK107 Results in Reduced Toxicity.

| Group | Length of Time That Dose was Administered | # of Mice | Maximal Percent Weight Loss |
|---|---|---|---|
| Slow Injection of 4E+09 | 4 minutes | 11 | 6% |

EXAMPLE 20

Use of PPMK107 in the Treatment of Patients with Advanced Cancer

PPMK107 has been tested in a phase I clinical trial in the U.S.A. by the intravenous route. Twenty-three patients with advanced solid tumors, no longer amenable to established therapies, have been treated with PPMK107. Seventeen of these patients have received a single dose for the initial treatment course. Six other patients are receiving three doses per week for one week for the initial treatment course. The sizes of each patient's tumors were followed once per month. Patients with at least stable disease (less than 25% increase and less than 50% decrease in the sum of the products of all measurable tumors in the absence of any new lesions) were eligible for additional treatment courses each month.

Regression of a Palpable Tumor

A 68 year old female with colon carcinoma had a palpable abdominal tumor among her widespread metastases. After a single IV treatment with PPMK107, this patient experienced a 91% regression of this single abdominal wall tumor over the course of two weeks (Table 19). Measurements of the tumor one day after dosing (3.75×3 cm) were similar to the baseline measurements of 4×3 cm. However, by day 7 post dosing, the tumor had decreased in size to 2×2 cm and continued to decrease in size to 1.5×1.5 cm by day 14 after PPMK107 dosing. Previous to PPMK107 treatment, this tumor mass had been rapidly growing with a 1065% increase in tumor volume in the two weeks before PPMK107 dosing. This patient went off study because of increased growth of the tumor elsewhere.

TABLE 19

Size of Palpable Abdominal Wall Tumor in Patient #123 (68 year old Female with Metastatic Colon Carcinoma) After a Single IV PPMK107 Dose of 12 Billion PFU/$m^2$.

| Date | Time After Dosing | Tumor Dimensions (L × W, $cm^3$) | Tumor Volume (0.5 × L × W × W, $cm^3$) | % Reduction in Tumor Volume |
|---|---|---|---|---|
| Jul. 23, 1998 | Day 0 | 4 × 3 | 18. | — |
| Jul. 24, 1998 | Day 1 | 3.75 × 3 | 16.9 | 6% |
| Jul. 30, 1998 | Day 7 | 2 × 2 | 4.0 | 78% |
| Aug. 6, 1998 | Day 14 | 1.5 × 1.5 | 1.7 | 91% |

Stabilization of Cancer

Eight other patients, all of whom previously had tumor progression with conventional cancer therapies, experienced benefit in the form of stabilization of their advanced cancer after PPMK107 dosing. These patients with stable disease represent those with diverse types of cancer including renal cancer, pancreatic cancer, breast cancer and lung cancer. After three months of PPMK107 treatment, a 67 year old man with advanced and widely metastatic renal cancer currently had stable disease with no indications of any new growth and no indication of an increase in tumor size. There has been a higher rate for stable disease benefit with higher doses of PPMK107: Two out of 6 patients with stable disease (33% of patients) at the first two single dose levels (5.9 and 12 billion PFU per $m^2$) and 4 out of 5 patients (80% of patients) with stable disease at the highest single dose level (24 billion PFU per $m^2$ (Table 20).

TABLE 20

Treatment of Patients with Advanced Cancer with PPMK107

| Dose Level (Billion PFU per $m^2$) | # of Patients Treated at this Dose Level | # of Patients with Stable Disease | % of Patients with Stable Disease | Types of Cancer with Stable Disease for at Least One Month & Length of Stable Disease |
|---|---|---|---|---|
| 5.9 | 6 | 2 | 33% | Renal Cancer-Ongoing 3 months Lung Cancer-Ongoing 2 months |
| 12 | 6 | 2 | 33% | Pancreatic Cancer-Ongoing 2 months Ovarian Cancer-Ongoing 1 month |
| 24 | 5 | 4 | 80% | Breast Cancer-Ongoing 1 month Breast Cancer-Ongoing 1 month Lung Cancer-Ongoing 1 month Pancreatic Cancer-Ongoing 1 month |
| Total | 17 | 8 | 47% | Noted Above. |

Reduction in Pain Medication

One patient at the single dose 5.9 billion PFU/$m^2$ dose level benefited from PPMK107 treatment in the form of symptomatic relief of cancer pain as denoted by a reduction in narcotic pain medication.

Desensitization

A clear desensitizing effect from the first dose (at 5.9 billion PFU/$m^2$) is seen on subsequent doses (also at 5.9 billion PFU/$m^2$) within the same week. In general, the reported side effects from second and third doses have been much less. For example, the first 4 patients in this multidose treatment regimen (three doses per week for one week) had fever after the first dose in spite of receiving prophylactic antipyretic treatment with acetaminophen and ibuprofen. The majority of these patients had no fever after receiving the second and third doses, even in cases in which they did not receive antipyretics. This indicates that administration of the first dose in the three times per week schedule reduces the toxicity for the second and third doses.

Dosing Through Neutralizing Antibodies in Serum

Using the dose range in this phase I study ($\geq$5.9 billion PFU/$m^2$), there is also clear indication that one can effectively deliver virus to patients even if they have generated neutralizing antibodies. A 72 year old woman with pancreatic cancer at the 12 billion PFU/$m^2$ single dose level has had stable disease for 2 months since beginning PPMK107 treatment. A second course (consisting of a single IV dose of PPMK107) was administered one month after the first dose when the patient had produced neutralizing antibodies in her serum. Seven days after this second course, her urine was positive for PPMK107 at a titer of at least 40 PFU per mL. This result indicates that the neutralizing antibodies to PPMK107 in this patient's serum was not able to completely inhibit the virus with a second treatment course.

EXAMPLE 21

Summary of Cytotoxicity Assay Results with Newcastle Disease Virus PPNJROAKIN Human tumor cells and normal cells were grown to approximately 80% confluence in 24 well tissue culture dishes. Growth medium was removed and PPNJROAKIN, a plaque purified clone of the mesogenic Newcastle disease virus strain New Jersey Roakin-1946, was added in 10 fold dilutions ranging from $10^7$ plaque forming units (PFU)/well to 1 PFU/well. Controls wells with no virus added were included on each plate. Virus was adsorbed for 90 minutes on a rocking platform at 37° C. At the end of the incubation period, the viral dilutions were removed and replaced by 1 ml of growth medium. Plates were then incubated for 5 days at 37° C. in 5% CO2. Cytotoxicity was quantified by using a colorimetric MTT (2-[4,5-dimethylthiazol-2-yl]-2,5-diphenyl tetrazolium bromide) assay (Cell Titer 96, catalog #G4000, Promega Corporation, Madison Wis. 53711) monitored at 570 nm, that detects mitochondrial enzyme activity (Mosman, T., 1983, J. Immunol. Methods 65:55). The viability in the virus treated wells was expressed as a percent of the activity in untreated control wells. The data was plotted graphically as PFU/well vs. viability as a percent of control. The IC50 was calculated as the amount of virus in PFU/well causing a 50% reduction in the amount of viable cells.

TABLE 21

Summary of Cytotoxicity Assay Results with PPNJROAKIN.

| Cell Type | Cell Line | $IC_{50}$ (PFU/well) |
|---|---|---|
| Fibrosarcoma | HT1080 | 13.8 |
| Head and Neck Carcinoma | KB | 2.4 |
| Normal Fibroblast | CCD922sk | $1.2 \times 10^4$ |

These results (Table 21) show that PPNJROAKIN demonstrates tumor-selective killing of at least two different human tumor cells (HT1080 and KB) relative to normal skin fibroblasts. The IC50 values for the two tumor cell lines are between 800 and 5000-fold lower than that for normal cells.

EXAMPLE 22

Summary of Cytotoxicity Assay Results with Newcastle Disease Virus PPCONN70726

Human tumor cells and normal cells were grown to approximately 80% confluence in 24 well -tissue culture dishes. Growth medium was removed and PPCONN70726, a plaque purified clone of the mesogenic Newcastle disease virus strain Connecticut 70726-1946, was added in 10 fold dilutions ranging from $10^7$ plaque forming units (PFU)/well to 1 PFU/well. Controls wells with no virus added were included on each plate. Virus was adsorbed for 90 minutes on a rocking platform at 37° C. At the end of the incubation period, the viral dilutions were removed and replaced by 1 ml of growth medium. Plates were then incubated for 5 days at 37° C. in 5% CO2. Cytotoxicity was quantified by using a colorimetric MTT (2-[4,5-dimethylthiazol-2-yl]-2,5-diphenyl tetrazolium bromide) assay (Cell Titer 96, catalog #G4000, Promega Corporation, Madison Wis. 53711) monitored at 570 nm, that detects mitochondrial enzyme activity (Mosman, T., 1983, J. Immunol. Methods 65:55). The viability in the virus treated wells was expressed as a percent of the activity in untreated control wells. The data was plotted graphically as PFU/well vs. viability as a percent of control. The IC50 was calculated as the amount of virus in PFU/well causing a 50% reduction in the amount of viable cells.

TABLE 22

Summary of Cytotoxicity Assay Results with PPCONN70726.

| Cell Type | Cell Line | $IC_{50}$ (PFU/well) |
|---|---|---|
| Head and Neck Carcinoma | KB | 18.1 |
| Glioblastoma | U87MG | 12.7 |
| Glioblastoma | U373MG | 879 |
| Normal Fibroblast | CCD922sk | $7.3 \times 10^4$ |

These results (Table 22) show that PPCONN70726 demonstrates tumor-selective killing of at least three different human tumor cells (KB, U87MG, and U373MG) relative to normal skin fibroblasts. The IC50 values for the two tumor cell lines are between 80 and 5000-fold lower than that for normal cells.

EXAMPLE 23

Intratumoral Treatment of HT1080 Fibrosarcoma Xenografts in Athymic Mice Using PPMK107, PPNJROAKIN, or PPCONN70726

In this experiment, athymic mice (female, NCR nu/nu, 5 to 6 weeks old) received a subcutaneous injection of $10^7$ HT1080 tumor cells. Four days later when tumors reached a size range of 6 to 8.5 mm, mice were treated treated intratumorally with saline, PPMK107 (at $1\times10^8$ PFU), PPNJROAKIN (at $1\times10^8$ PFU), or PPCONN70726 (at $1\times10^8$ PFU). As shown in Table 23, tumor regression was noted in mice treated with these three viruses (PPMK107, PPNJROAKIN, and PPCONN70726). After PPMK107 treatment of 12 mice, four experienced complete tumor regression and six experienced partial regression. After PPNJROAKIN treatment of 12 mice, one mouse experienced complete tumor regression and two experienced partial regression. After PPCONN70726 treatment of 12 mice, three experienced complete tumor regression and two experienced partial regression. No tumor regression was noted in any of the animals treated with saline. These results show that the three mesogenic strains of NDV can cause tumor regression.

TABLE 23

Regression of HT1080 Fibrosarcoma Tumors in Athymic Mice after Treatment with One of Three Viruses (PPMK107, PPNJROAKIN and PPCONN70726) Each at a Dose of $1 \times 10^8$ PFU.

| | | Regression | | |
|---|---|---|---|---|
| Treatment | # of Mice | Partial (PR) | Complete (CR) | PR + CR (%) |
| PPMK107 | 12 | 6 | 4 | 10 (83%) |
| PPNJROAKIN | 12 | 2 | 1 | 3 (25%) |
| PPCONN70726 | 12 | 2 | 3 | 5 (42%) |
| Saline | 11 | 0 | 0 | 0 (0%) |

EXAMPLE 24

Effects of PPMK107, PPNJROAKIN, PPCONN70726 after Intracerebral Injection in Immunodeficient Athymic (nu/nu) and Immunocompetent Heterozygote (nu/+) Mice Fifty-six athymic mice (nu/nu) and 56 immunocompetent heteroxygote (nu/+) mice were given stereotaxic intracerebral injections with either saline, PPMK107, PPNJROAKIN, or PPCONN70726. Eight additional mice of each type were used as untreated controls. Viruses were used at one of two dose levels ($2 \times 10^4$ or $3.5 \times 10^6$ PFU/mouse). As shown in Table 24, all of the heterozygote nu/+ mice treated with each of the three viruses at the two dose levels survived through day 39 with the exception of one mouse at the lower PPCONN70726 dose level that was euthanized for non-neurological symptoms. Athymic nu/nu animals treated with either PPMK107 or PPCONN70726 had significantly less survival than the heterozygotes. This was especially true for the highest PPMK107 or PPCONN70726 virus dose of $3.5 \times 10^6$ PFU/mouse where only 13% (1 of 8) of the athymic animals in each virus group survived through day 39. In contrast, there was 75% survival of the PPNJROAKIN-treated athymic mice at this same dose level ($3.5 \times 10^6$ PFU/mouse). These data indicate that PPNJROAKIN is better tolerated in the brains of athymic mice than the other two virus strains.

TABLE 24

Survival of Mice Following Intracerebral Injection of PPMK107, PPCONN70726, and PPNJROAKIN

| | Intracranial Injection | # of Mice | % Survival at Day 39 |
|---|---|---|---|
| nu/+ | Untreated | 8 | 100 |
| nu/+ | Saline | 8 | 100 |
| nu/+ | PPMK107, 2E+04 | 8 | 100 |
| nu/+ | PPMK107, 3.5E+06 | 8 | 100 |
| nu/+ | PPCONN70726, 2E+04 | 8 | 88* |
| nu/+ | PPCONN70726, 3.5E+06 | 8 | 100 |
| nu/+ | PPNJROAKIN, 2E+04 | 8 | 100 |
| nu/+ | PPNJROAKIN, 3.5E+06 | 8 | 100 |
| nu/nu | Untreated | 8 | 100 |
| nu/nu | Saline | 8 | 100 |
| nu/nu | PPMK107, 2E+04 | 8 | 75 |
| nu/nu | PPMK107, 3.5E+06 | 8 | 13 |
| nu/nu | PPCONN70726, 2E+04 | 8 | 75 |
| nu/nu | PPCONN70726, 3.5E+06 | 8 | 13 |
| nu/nu | PPNJROAKIN, 2E+04 | 8 | 100 |
| nu/nu | PPNJROAKIN, 3.5E+06 | 8 | 75 |

*The one non-surviving mouse in this treatment group was euthanized for non-neurological symptoms.

EXAMPLE 25

Summary of Cytotoxicity Assay Results with Sindbis Virus PPSINDBIS-Ar339

Human tumor cells and normal cells were grown to approximately 80% confluence in 24 well tissue culture dishes. Growth medium was removed and PPSINDBIS-Ar339, a plaque purified clone of Sindbis Ar-339 was added in 10 fold dilutions ranging from $10^7$ plaque forming units (PFU)/well to 1 PFU/well. Controls wells with no virus added were included on each plate. Virus was adsorbed for 90 minutes on a rocking platform at 37° C. At the end of the incubation period, the viral dilutions were removed and replaced by 1 ml of growth medium. Plates were then incubated for 5 days at 37° C. in 5% CO2. Cytotoxicity was quantified by using a colorimetric MTT (2-[4,5-dimethylthiazol-2-yl]-2,5-diphenyl tetrazolium bromide) assay (Cell Titer 96, catalog #G4000, Promega Corporation, Madison Wis. 53711) monitored at 570 nm, that detects mitochondrial enzyme activity (Mosman, T., 1983, J. Immunol. Methods 65:55). The viability in the virus treated wells was expressed as a percent of the activity in untreated control wells. The data was plotted graphically as PFU/well vs. viability as a percent of control. The IC50 was calculated as the amount of virus in PFU/well causing a 50% reduction in the amount of viable cells.

TABLE 25

Summary of Cytotoxicity Assay Results with PPSINDBIS-Ar339

| Cell Type | Cell Line | $IC_{50}$ (PFU/well) |
|---|---|---|
| Pancreatic Carcinoma | Panc-1* | 69 |
| Colorectal Carcinoma | SW620* | 13 |
| Colorectal Carcinoma | SW1463 | $1.8 \times 10^5$ |
| Non-small cell Lung carcinoma | A427 | $>1 \times 10^6$ |
| Non-small cell Lung carcinoma | A549 | $5.2 \times 10^4$ |
| Renal carcinoma | A498 | $2.4 \times 10^4$ |
| Renal carcinoma | Caki-1 | $3.4 \times 10^4$ |
| Fibrosarcoma | HT1080 | $7.4 \times 10^5$ |
| Normal Keratinocyte | NHEK | $2.0 \times 10^5$ |
| Normal Fibroblast | CCD922sk | $1.6 \times 10^5$ |

*Cells known to overexpress the mRNA for the high affinity laminin receptor.

The cellular receptor for Sindbis virus on mammalian cells is the high affinity laminin receptor, that is expressed mainly on cells of epithelial lineage, but is often overexpressed in many metastatic cancer cells like the Panc-1 pancreatic carcinoma line, and the SW620 colon adenonocarcinoma cell line (Campo et al., (1992) Am. J. Pathol. 141, 1073-1083; Yow et al., (1988) Proc. Natl Acad Sci, 85, 6394-6398). In contrast, the rectum adenocarcinoma cell line SW1423 is known to express very low levels of high affinity laminin receptor mRNA (Yow et al., (1988) Proc. Natl Acad Sci, 85, 6394-6398), and is more than 4 order of magnitude more resistant to killing by PPSINDBIS-Ar339 than SW620 cells. These results (Table 25) demonstrate that cells that are tumorigenic and express high levels of the high affinity laminin receptor are more sensitive to killing by Sindbis Clone PPSINDBIS-Ar339 than other tumor or normal cells.

EXAMPLE 26

VSV Killing of Tumorigenic and Non-Tumorigenic Cells in the Presence of Interferon In 96 well plates, tumorigenic KB and HT1080 cells ($3 \times 10^4$ cells per well) and non-tumorigenic WISH cells ($2.5 \times 10^4$ cells per well) were seeded in the presence of serially diluted interferon-a ranging from 2800 to 22 Units/ml and allowed to incubate for 24 hours at 37° C. The cells were then infected with vesicular stomatitis virus (VSV, Indiana strain) at an moi of 10. Controls were included for cells without interferon, and cells without interferon or virus. The cells were incubated at 37° for 24 hours. Cytotoxicity was quantified by using a colorimetric MTT (2-[4,5-dimethylthiazol-2-yl]-2,5-diphenyl tetrazolium bromide) assay (Cell Titer 96, catalog #G4000, Promega Corporation, Madison Wis. 53711) monitored at 570 nm, that detects mitochondrial enzyme activity (Mosman, T., 1983, J. Immunol. Methods 65:55). The viability in the virus treated wells was expressed as a percent of the activity in control wells not receiving virus.

TABLE 26

Comparison of the Cell Killing Activity of VSV in Cells Treated with Exogenous Interferon.

| | Percent Viable Cells | | |
|---|---|---|---|
| | WISH | HT1080 | KB |
| 100 U/ml IFN | 50 | 6 | 0 |
| 1000 U/ml IFN | 95 | 20 | 12 |

These results (Table 26) demonstrate that VSV is able to selectively kill tumor cells deficient in interferon responsiveness (see Example 27). WISH cells (human amnion cells) are a well established cell line for the use in interferon bioassays because of their ability to respond efficiently to interferons.

EXAMPLE 27

Interferon Responsiveness in Cells Sensitive or Resistant to Killing by PPMK107

Individual cell lines were grown to near confluence in 96 well microtiter plates and treated with between 5 and 5000 U/ml of IFNαA for 24 hours. The cultures were then infected with PPMK107 at an moi of 1.0 and cultured for an additional 24 hours. Following chemical fixation, the amount of viral expression was quantified by immunohistochemistry using a soluble indicator dye. The amount of virus growth is represented as the percent of P antigen expressed relative to control cells untreated with interferon (FIG. 5). In this assay, interferon responsive cells manifest at least a 50% decrease in the viral antigen in response to interferon. Cells in FIG. 5 that are sensitive to PPMK107 are indicated by the solid lines; cells less sensitive are indicated by the dashed lines.

The results of this experiment show a strong correlation between the resistance of the cell line to the antiviral effects of exogenous interferon and the relative sensitivity of the cell to killing by PPMK107 (indicated by the IC50 value shown in parentheses next to the cell line name in the graph legend, see FIG. 5). For example, following pretreatment with 5 U/ml of interferon, 6 of 7 (86%) cell lines nonresponsive to interferon are sensitive to killing by PPMK107; when pretreated with 500 U/ml of interferon, all (4 of 4) of the nonresponsive cell lines are sensitive to killing by PPMK107.

The data above also present an example of a screening assay to identify candidate cells that are likely to be sensitive to killing by PPMK107 or other interferon-sensitive viruses. For example, infected cells expressing significant (e.g., more than 50% of controls) viral antigen following pretreatment with exogenous interferon would be considered interferon deficient and thereby sensitive to viral oncolysis.

The foregoing is intended as illustrative of the present invention but not limiting. Numerous variations and modifications may be effected without departing from the true spirit and scope of the invention.

What is claimed is:

1. A method of infecting a cell of a neoplasm in a mammal with a virus, the method comprising administering an interferon-sensitive, replication-competent vaccinia virus to the mammal, wherein the virus comprises one or more mutations in one or more genes selected from the group consisting of K3L, E3L, and B18R, wherein the one or more mutations increases the interferon sensitivity of the virus.

2. The method of claim 1, wherein the virus comprises one or more mutations in two or more genes selected from the group consisting of K3L, E3L, and B18R.

3. The method of claim 1, wherein the vaccinia virus replicates at least 100-fold less in the presence of interferon compared to in the absence of interferon.

4. The method of claim 1, wherein the vaccinia virus replicates at least 1000-fold less in the presence of interferon compared to in the absence of interferon.

5. The method of claim 1, wherein said administering is systemic.

6. The method of claim 1, wherein said administering is intravenous.

7. The method of claim 1, wherein said administering is intratumoral.

8. The method of claim 1, wherein the virus is administered as more than one dose.

9. The method of claim 8, wherein the first dose is a desensitizing dose.

10. The method of claim 8, wherein the first dose is administered intravenously.

11. The method of claim 8, wherein a dose is administered intraperitoneally subsequent to the first dose.

12. The method of claim 8, wherein a dose is administered intravenously subsequent to the first dose.

13. The method of claim 1, wherein a dose is administered intra-arterially subsequent to the first dose.

14. The method of claim 1, resulting in reducing pain in the mammal.

15. The method of claim 1, resulting in regression of the neoplasm.

16. The method of claim 8, wherein multiple courses of virus are administered.

17. The method of claim 1, wherein the virus is a clonal virus.

18. The method as in claim 17, wherein the clonal virus is obtained by plaque purification or obtained by limiting dilutions.

19. The method of claim 1, wherein the neoplasm is a cancer.

20. The method of claim 19, wherein the cancer is selected from the group consisting of lung, colon, prostate, breast, ascites and brain cancer.

21. The method of claim 1, wherein the neoplasm is a solid tumor.

22. The method of claim 1, wherein the neoplasm is a glioblastoma.

23. The method of claim 1, wherein the virus contains a heterologous gene encoding a pro-drug activating enzyme.

24. The method of claim 1, wherein the virus contains a heterologous gene encoding an interferon to permit the viral expression of the heterologous gene.

25. The method of claim 1, wherein at least one dose of the virus is administered over the course of at least 4 minutes.

26. The method of claim 1, further comprising administering IFN, before, during or after administration of the virus.

27. The method of claim 26, wherein the interferon is selected from the group consisting of an α-IFN, a β-IFN, a ω-IFN, a γ-IFN, and a synthetic consensus form of IFN.

28. The method of claim 1, further comprising administering before, during or after administration of the virus a compound selected from the group consisting of a purine nucleoside analog, a tyrosine kinase inhibitor, a cimetidine, a mitochondrial inhibitor, a chemotherapeutic agent, a cytokine, an immunosuppressant and a second virus.

29. The method of claim 28, wherein the cytokine is a GM-CSF, a TNF or an IL-2.

30. The method of claim 28, wherein the immunosuppressant is a corticosteroid.

31. The method of claim 1, wherein the mammal is a human.

32. The method of claim 1, wherein the neoplasm is from 2 centimeters (cm) to 5 cm.

33. The method of claim 1, wherein the neoplasm is at least 5 cm.

34. The method of claim 1, wherein the neoplasm is at least 2 cm.

35. The method of claim 1, wherein the neoplasm is at least 1 cm.

36. The method of claim 1, wherein the neoplasm is at least 300 mm$^3$ in volume.

37. The method of claim 1, wherein the neoplasm is from about 1% to about 2% of the total body weight of the mammal.

38. The method of claim 1, wherein the neoplasm does not respond to a chemotherapy.

39. The method of claim 1, comprising a step of screening a cell of the neoplasm for a protein, or mRNA encoding a protein, selected from the group consisting of p68 protein kinase, C-Myc, C-Myb, ISGF-3, IRF-I, IFN receptor, and p58.

40. The method of claim 1, comprising subjecting a sample from the mammal to an immunoassay to detect the amount of receptor for the virus that is present, and if the receptor is present, administering the virus to the mammal.

41. The method of claim 1, wherein the virus further comprises one or more attenuating mutations in at least two genes selected from the group consisting of vaccinia growth factor, thymidine kinase, thymidylate kinase, DNA ligase, ribonucleotide reductase and dUTPase.

42. The method of claim 1, wherein the virus further comprises one or more attenuating mutations in the vaccinia growth factor and the thymidine kinase gene.

43. The method of claim 1, wherein the virus comprises one or more mutations in the K3L gene.

44. The method of claim 43, wherein the virus further comprises one or more attenuating mutations in a thymidine kinase gene.

45. The method of claim 43, wherein the virus further comprises one or more attenuating mutations in a vaccinia growth factor gene.

46. The method of claim 43, wherein the virus further comprises one or more attenuating mutations in a thymidylate kinase gene.

47. The method of claim 43, wherein the virus further comprises one or more attenuating mutations in a DNA ligase gene.

48. The method of claim 43, wherein the virus further comprises one or more attenuating mutations in a ribonucleotide reductase gene.

49. The method of claim 43, wherein the virus further comprises one or more attenuating mutations in a dUTPase gene.

50. The method of claim 1, wherein the virus comprises one or more mutations in the E3L gene.

51. The method of claim 50, wherein the virus further comprises one or more attenuating mutations in a thymidine kinase gene.

52. The method of claim 50, wherein the virus further comprises one or more attenuating mutations in a vaccinia growth factor gene.

53. The method of claim 50, wherein the virus further comprises one or more attenuating mutations in a thymidylate kinase gene.

54. The method of claim 50, wherein the virus further comprises one or more attenuating mutations in a DNA ligase gene.

55. The method of claim 50, wherein the virus further comprises one or more attenuating mutations in a ribonucleotide reductase gene.

56. The method of claim 50, wherein the virus further comprises one or more attenuating mutations in a dUTPase gene.

57. The method of claim 1, wherein the virus comprises one or more mutations in the B18R gene.

58. The method of claim 57, wherein the virus further comprises one or more attenuating mutations in a thymidine kinase gene.

59. The method of claim 57, wherein the virus further comprises one or more attenuating mutations in a vaccinia growth factor gene.

60. The method of claim 57, wherein the virus further comprises one or more attenuating mutations in a thymidylate kinase gene.

61. The method of claim 57, wherein the virus further comprises one or more attenuating mutations in a DNA ligase gene.

62. The method of claim 57, wherein the virus further comprises one or more attenuating mutations in a ribonucleotide reductase gene.

63. The method of claim 57, wherein the virus further comprises one or more attenuating mutations in a dUTPase gene.

* * * * *